United States Patent
Andersen et al.

(10) Patent No.: US 6,613,903 B2
(45) Date of Patent: *Sep. 2, 2003

(54) MODULATORS OF PROTEIN TYROSINE PHOSPHATASES (PTPASES)

(75) Inventors: Henrik Sune Andersen, Lyngby (DK); Thomas Kruse Hansen, Herlev (DK); Jesper Lau, Farum (DK); Niels Peter Hundahl Moller, Kobenhavn O (DK); Ole Hvilsted Olsen, Bronshoj (DK); Frank Urban Axe, Escondido, CA (US); Farid Bakir, San Diego, CA (US); Yu Ge, San Diego, CA (US); Daniel Dale Holsworth, San Diego, CA (US); Luke Milburn Judge, Seattle, WA (US); Michael James Newman, San Diego, CA (US); Roy Teruyuki Uyeda, San Diego, CA (US); Barry Zvi Shapira, Acton, CA (US)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 09/901,367

(22) Filed: Jul. 9, 2001

(65) Prior Publication Data

US 2002/0151561 A1 Oct. 17, 2002

Related U.S. Application Data

(60) Provisional application No. 60/235,726, filed on Sep. 27, 2000.

(30) Foreign Application Priority Data

Jul. 7, 2000 (DK) ........................ 2000 01068

(51) Int. Cl.$^7$ .................. C07D 471/02; A61K 31/4436

(52) U.S. Cl. ....................... 546/114; 514/301

(58) Field of Search .......................... 546/114

(56) References Cited

U.S. PATENT DOCUMENTS 6,410,556 B1 * 6/2002 Andersen et al. ........... 514/301

FOREIGN PATENT DOCUMENTS

| WO | WO 97/08934 | 3/1997 |
|---|---|---|
| WO | WO 97/15529 | 5/1997 |
| WO | WO 97/39748 | 10/1997 |
| WO | WO 97/40017 | 10/1997 |
| WO | WO 98/27065 | 6/1998 |
| WO | WO 99/15529 | 4/1999 |
| WO | WO 99/46236 | 9/1999 |
| WO | 9946237 * | 9/1999 |
| WO | WO 99/46237 | 9/1999 |
| WO | WO 99/46244 | 9/1999 |
| WO | WO 99/46267 | 9/1999 |
| WO | WO 99/46268 | 9/1999 |
| WO | WO 01/17516 | 3/2001 |
| WO | WO 01/19830 A1 | 3/2001 |
| WO | WO 01/19831 A1 | 3/2001 |

OTHER PUBLICATIONS

Matozaki et al., Cell Signal., vol. 8, pp. 13–19 (1996).
Burke, Jr. et al., Biopolymers (Peptide Science), vol. 47, pp. 225–241 (1998).
Tonks et al., Cell, vol. 87, pp. 365–368 (1996).
Tony Hunter, Phil. Trans. R. Soc. Lond. B, vol. 353, pp. 583–605.
Elchebly et al., Science, vol. 283, pp. 1544–1548 (1999).
Clemens et al., Molecular Microbiology, vol. 5, pp. 2617–2620 (1991).
Evans et al., Exp. Opin. Invest. Drugs, vol. 8, pp. 139–160 (1999).
Frangioni et al., The EMBO Journal, vol. 12, pp. 4843–4856 (1993).
Wrobel et al., J. Med. Chem., vol. 42, pp. 3199–3202 (199).
Fischer et al., Science, vol. 253, pp. 401–406 (1991).
Neel et al., Current Opinion in Cell Biology, vol. 9, pp. 193–204 (1997).
Chan et al., Annu. Rev. Immunol., vol. 12, pp. 555–592 (1994).
Zhong–Yin Zhang, Current Topics in Cellular Regulation, vol. 35, pp. 21–68 (1997).
Zhong–Yin Zhang, Critical Reviews in Biochemistry and Molecular Biology, vol. 33, pp. 1–52 (1998).

* cited by examiner

Primary Examiner—Alan L. Rotman
Assistant Examiner—Binta Robinson
(74) Attorney, Agent, or Firm—Rosemarie R. Wilk-Orescan; Reza Green

(57) ABSTRACT

The present invention provides novel thienopyridines, novel compositions, methods of their use, and methods of their manufacture, where such compounds of Formula 1 are pharmacologically useful inhibitors of Protein Tyrosine Phosphatases (PTPase's) including PTP1B, T cell PTP, Formula 1

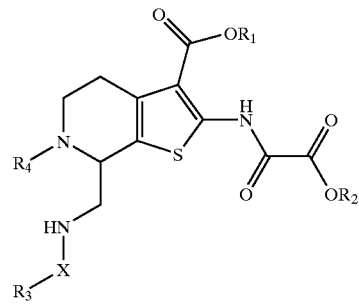

wherein X, $R_1$, $R_2$, $R_3$, and $R_4$ are defined more fully in the description. The compounds are useful in the treatment of type 1 diabetes, type 2 diabetes, impaired glucose tolerance, insulin resistance, obesity, and other diseases.

21 Claims, No Drawings

MODULATORS OF PROTEIN TYROSINE PHOSPHATASES (PTPASES)

CROSS REFERENCE TO RELATED APPLICATIONS

This application claims priority under 35 U.S.C. 119 of Danish application no. PA 2000 01068 filed on Jul. 7, 2000, and U.S. provisional application No. 60/235,726 filed on Sep. 27, 2000, the contents of which are fully incorporated herein by reference.

FIELD OF THE INVENTION

The present invention relates to novel thienopyridines, to methods for their preparation, to compositions comprising the compounds, to the use of these compounds as medicaments and their use in therapy, where such compounds of Formula 1 are pharmacologically useful inhibitors or modulators of Protein Tyrosine Phosphatases (PTPases) including PTP1B and T cell PTP, Formula 1

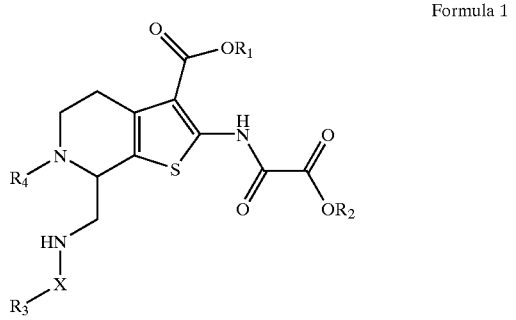

wherein X, $R_1$, $R_2$, $R_3$, and $R_4$ are defined more fully below.

It has been found that PTPases play a major role in the modulation and regulation of fundamental cellular signaling mechanisms involved in metabolism, growth, proliferation and differentiation (Fischer et al, *Science* 253:401–6 (1991); Tonks and Neel, Cell 87: 365–368 (1996); Neel and Tonks, *Current Opinion in Cell Biology* 9: 193–204 (1997); Hunter, Phil. Trans. R. Soc. Lond. B 353: 583–605 (1998); Zhang, *Critical Reviews in Biochemistry and Molecular Biology* 33:1–52 (1998)). There is increasing evidence which suggests that inhibition of these PTPases may help treat or manage certain types of diseases such as type 1 and type 2 diabetes, obesity, autoimmune diseases, acute and chronic inflammation, osteoporosis and various forms of cancer. In addition, certain infectious diseases may also be treated or managed by administration PTPase inhibitors (Clemens et al., *Molecular Microbiology* 5: 2617–2620 (1991)).

BACKGROUND OF THE INVENTION

Protein phosphorylation is now well recognized as an important mechanism utilized by cells to transduce and regulate signals during different stages of cellular function (Hunter, vide supra; Chan et al., *Annu. Rev. Immunol.* 12: 555–592 (1994); Zhang, *Curr. Top. Cell. Reg.* 35: 21–68 (1997); Matozaki and Kasuga, *Cell. Signal.* 8: 113–19 (1996); Fischer et al, vide supra). The level of tyrosine phosphorylation is balanced by the opposing action of protein tyrosine kinases and protein tyrosine phosphatases (PTPases). There are at least two major classes of phosphatases: (1) those that dephosphorylate proteins (or peptides) that contain a phosphate group(s) on a serine or threonine moiety (termed Ser/Thr phosphatases) and (2) those that remove a phosphate group(s) from the amino acid tyrosine (termed protein tyrosine phosphatases or PTPases or PTPs). The PTPases are a family of enzymes that can be classified into two groups: a) intracellular or nontransmembrane PTPases and b) receptor-type or transmembrane PTPases. In addition, dual-specificity phosphatases and low molecular weight phosphatases can also dephosphorylate phosphotyrosyl proteins (WO97/39748, WO97/40017, WO99/15529, WO97/08934, WO98/27065, WO99/46236, WO99/46244, WO99/46267, WO99/46268, WO99/46237).

It has been found that PTPases play a major role in the above modulation and regulation of fundamental cellular signaling mechanisms involved in metabolism, growth, proliferation and differentiation (Fischer et al, *Science* 253:401–6 (1991); Tonks and Neel, Cell 87: 365–368 (1996); Neel and Tonks, *Current Opinion in Cell Biology* 9: 193–204 (1997); Hunter, *Phil. Trans. R. Soc. Lond. B* 353: 583–605 (1998); Zhang, *Critical Reviews in Biochemistry and Molecular Biology* 33:1–52 (1998)). Reports from many laboratories have shown that PTPases can act both as positive and negative regulators of signal transduction processes. PTPases have been implicated in a variety of human diseases, including type land type 2 diabetes, obesity, autoimmune diseases, acute and chronic inflammation, osteoporosis, proliferative disorders including various forms of cancer, growth disorders, and defective platelet aggregation (WO97/39748, WO97/40017, WO99115529, WO97/08934, WO98/27065, WO99/46236, WO99/46244, WO99/46267, WO99/46268, WO99/46237). Accordingly, there is increasing evidence which suggests that inhibition of these PTPases may help treat or manage said diseases (Hunter, vide supra; Neel and Tonks, vide supra; Frangione et al., *EMBO J.* 12: 4843–4856; Zhang, *Curr. Top. Cell. Reg.* 35: 21–68 (1997); Zhang, vide supra; Evans and Jallan, *Exp. Opinion. Invest. Drugs* 8: 139–160 (1999); Burke and Zhang, *Biopolymers (Peptide Science)* 47: 225–241 (1998); Elchebly et al., *Science* 283: 1544–1548 (1999); Wrobel et al., *J. Med. Chem.* 42: 3199–3202 (1999)). In addition, certain infectious diseases may also be treated or managed by administration PTPase inhibitors (Clemens et al., *Molecular Microbiology* 5: 2617–2620 (1991)).

Both selective PTPase inhibitors and inhibitors that bind to several PTPases (non-selective inhibitors) can be used therapeutically to partially or completely restore PTPase-mediated perturbed signal transduction processes and thus for management, treatment or prevention of the above diseases.

WO 99/46267 discloses compounds which are pharmacologically useful inhibitors of PTPases. However, the present invention which represents a novel selection under WO 99/46267, discloses a class of compounds which surprisingly are more potent against protein tyrosine phosphatases (e.g. PTP1 B) than those disclosed in WO 99/46267.

DESCRIPTION OF THE INVENTION

The present invention relates to compounds of the Formula 1 wherein X, $R_1$, $R_2$, $R_3$, and $R_4$ are defined below;

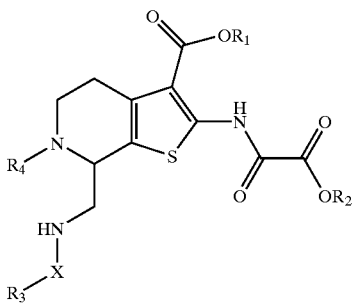

Formula 1 wherein

X is —C(O)— or —S(O)₂—;

R₁ and R₂ are independently hydrogen, C₁–C₆alkyl, aryl-R₅—, R₆—C(O)—O—R₇— or aryl-R₈—C(O)—O—R₉— wherein aryl is phenyl, naphthyl or thiophenyl, which aryl group is optionally substituted with halogen, nitro, trihalomethyl, C₁–C₆alkyl or C₁–C₆alkyloxy;

R₃ is C₁–C₆alkyl, C₂–C₆alkenyl, C₂–C₆alkynyl, aryl, aryl-R₁₀—, aryl-N(R₃₅)—, aryl-R₁₁—N(R₃₆)—, N(R₃₇)(R₃₈)—R₃₉—, C₁–C₆alkyloxy or aryl-R₁₃—O— wherein aryl is phenyl, biphenyl, indenyl, naphthyl, imidazolyl, benzo[b]furanyl, 1,2,3-triazolyl, thiophenyl, pyridyl, quinolyl, isoquinolyl, indolyl or benzimidazolyl, which aryl group is optionally substituted with halogen, nitro, cyano, hydroxy, trihalomethyl, C₁–C₆alkyl, aryl, aryl-R₁₄—, C₁–C₆alkyloxy, aryloxy, aryl-R₁₅—O—, aryl-N(R₁₆)—, R₁₈—C(O)—N(R₁₉)—, aryl-C(O)—N(R₂₁)— or aryl-R₂₃—C(O)—N(R₂₄)— and wherein aryl is phenyl, naphthyl or thiophenyl;

R₄ is hydrogen, R₂₇—O—C(O)—, aryl-R₂₈—O—C(O)—, R₂₉—C(O)—O—R₃₀—OC(O)— or aryl-R₃₁—C(O)—O—R₃₂—O—C(O)— wherein aryl is phenyl, naphthyl or thiophenyl, which aryl group is optionally substituted with halogen, nitro, cyano, trihalomethyl, aryl, aryl-R₃₃—, C₁–C₆alkyloxy or aryl-R34—O— and wherein aryl group is phenyl, naphthyl or thiophenyl;

and wherein R₅, R₇, R₈, R₉, R₁₀, R₁₁, R₁₃, R₁₄, R₁₅, R₂₃, R₂₈, R₃₀, R₃₁, R₃₂, R₃₃, R₃₄, and R₃₉ independently are C₁–C₆alkylene, wherein R₆, R₁₂, R₁₇, R₁₈, R₂₀, R₂₂, R₂₅, R₂₇, R₂₉, R₃₇, and R₃₈ independently are C₁–C₆alkyl and wherein R₁₆, R₁₉, R₂₁, R₂₄, R₃₅ and R₃₆ independently are hydrogen or C₁–C₆alkyl;

or a salt thereof with a pharmaceutically acceptable acid or base, or any optical isomer or mixture of optical isomers, including a racemic mixture, or any tautomeric form.

The compounds of the invention can be further modified to act as prodrugs.

A preferred prodrug is acetoxymethyl esters or acetoxymethyl carbamates of the compounds of the present invention. As a general procedure preparation of an acetoxymethyl ester is given below (C. Schultz et al, *The Journal of Biological Chemistry*, 1993, 268, 6316–6322.):

A carboxylic acid (1 equivalent) is suspended in dry acetonitrile (2 ml per 0.1 mmol). Diisopropyl amine (3.0 equivalents) is added followed by bromomethyl acetate (1.5 equivalents). The mixture is stirred under nitrogen overnight at room temperature. Acetonitrile is removed under reduced pressure to yield an oil which is diluted in ethyl acetate and washed with water (3×). The organic layer is dried over anhydrous magnesium sulfate, filtred and the solvent removal under reduced pressure affording a crude oil. The product is purified by column chromatography on silica gel, using an appropriate solvent system known to those skilled in the art.

Definitions

As used herein, the term "attached" or "–" signifies a stable covalent bond, certain preferred points of attachment points being apparent to those skilled in the art.

The terms "halogen" and "halo" includes fluorine, chlorine, bromine, and iodine.

The term "alkyl" includes C₁–C₆ straight chain saturated, C₁–C₆ branched chain saturated and C₃–C₆ cyclic saturated hydrocarbon groups. For example, this definition shall include but is not limited to methyl (Me), ethyl (Et), propyl (Pr), butyl (Bu), pentyl, hexyl, isopropyl (i-Pr), isobutyl (i-Bu), tert-butyl (t-Bu), sec-butyl (s-Bu), cyclopropyl, cyclobutyl, cyclopentyl, cyclohexyl and the like.

The term "alkenyl" includes C₂–C₆ unsaturated aliphatic hydrocarbon groups and C₂–C₆ branched unsaturated aliphatic hydrocarbon groups having the specified number of carbon atoms and at lest one double bond. For example, this definition shall include but is not limited to ethenyl, propenyl, butenyl, pentenyl, hexenyl, isopentenyl, neopentenyl, cyclobutenyl, cyclopentenyl, cyclohexenyl, and the like.

The term "alkynyl" includes C₂–C₆ straight chain unsaturated aliphatic, C₂–C₆ branched unsaturated and cyclic C₆ unsaturated aliphatic hydrocarbon groups having the specified number of carbon atoms and at least one triple bond. For example, this definition shall include but is not limited to acetynyl, propynyl, butynyl, pentynyl, hexynyl, cyclohexynyl and the like.

The term "alkyloxy" (e.g. methoxy, ethoxy, propyloxy, allyloxy, cyclohexyloxy) represents an "alkyl" group as defined in claim 1 having the indicated number of carbon atoms attached through an oxygen bridge.

The term "aryloxy" (e.g. phenoxy, naphthyloxy and the like) represents an aryl group as defined below attached through an oxygen bridge.

The term "aryl" represents an unsubstituted, mono-, di- or trisubstituted monocyclic, polycyclic, biaryl or heterocyclic aromatic group(s) covalently attached at any ring position capable of forming a stable covalent bond, certain preferred points of attachment being apparent to those skilled in the art (e.g., 3-indolyl, 4(5)-imidazolyl).

The definition of aryl includes phenyl, biphenyl, indenyl, naphthyl (1-naphthyl, 2-naphthyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), thiophenyl (2-thiophenyl, 3-thiophenyl, 4-thiophenyl, 5-thiophenyl), pyridyl (2-pyridyl, 3-pyridyl, 4-pyridyl, 5-pyridyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), indolyl (1-indolyl, 2-indolyl, 3-indolyl, 4-indolyl, 5-indolyl, 6-indolyl, 7-indolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl).

It is a well known problem in drug discovery that compounds, such as enzyme inhibitors, may be very potent and selective in biochemical assays, yet be inactive in vivo. This lack of so-called bioavailability may be ascribed to a number of different factors such as lack of or poor absorption in the gut, first pass metabolism in the liver, poor uptake in cells. Although the factors determining bioavailability are not completely understood, there are many examples in the scientific literature—well known to those skilled in the art—of how to modify compounds, which are potent and selective in biochemical assays but show low or no activity in vivo, into drugs that are biologically active. By the term 'original compound' is understood a compound of Formula I wherein $R_1$ and $R_2$ are both hydrogen. It is within the scope of the invention to modify the original compounds of the invention by attaching chemical groups that will improve the bioavailability of said compounds in such a way that the uptake in cells or mammals is facilitated. Examples of said modifications, which are not intended in any way to limit the scope of the invention, include changing of one or more of the carboxy groups at the $R_1$ and $R_2$ position to esters (for instance methyl esters, ethyl esters, acetoxymethyl esters or other acyloxymethyl esters). Original compounds of the invention modified by attaching chemical groups are termed 'modified compounds'. Other examples of modified compounds, which are not intended in any way to limit the scope of the invention, are compounds that have been cyclized at specific positions—so called 'cyclic compounds'—which upon uptake in cells or mammals become hydrolysed at the same specific position(s) in the molecule to yield the compounds of the invention, the original compounds, which are then said to be 'non-cyclic'. For the avoidance of doubt, it is understood that the latter original compounds in most cases will contain other cyclic or heterocyclic structures that will not be hydrolysed after uptake in cells or mammals. Generally, said modified compounds may not show behaviour in biochemical assays similar to that of the original compound, i.e. the corresponding compounds of the invention without the attached chemical groups or said modifications. Said modified compounds may even be inactive in biochemical assays. However, after uptake in cells or mammals these attached chemical groups of the modified compounds may in turn be removed spontaneously or by endogenous enzymes or enzyme systems to yield compounds of the invention, original compounds. 'Uptake' is defined as any process that will lead to a substantial concentration of the compound inside cells or in mammals. After uptake in cells or mammals and after removal of said attached chemical group or hydrolysis of said cyclic compound, the compounds may have the same structure as the original compounds and thereby regain their activity and hence become active in cells and/or in vivo after uptake. Thus, the term 'a functional group which can be converted to hydrogen in vivo' is intended to include any group which upon administering the present compounds to the subjects in need thereof can be converted to hydrogen e.g. enzymatically or by the acidic environment in the stomach.

The compounds of the present invention have asymmetric centers and may occur as racemates, racemic mixtures, and as individual enantiomers or diastereoisomers, with all isomeric forms being included in the present invention as well as mixtures thereof.

Pharmaceutically acceptable salts of the compounds of Formula 1, where a basic or acidic group is present in the structure, are also included within the scope of this invention. When an acidic substituent is present, such as —COOH, 5-tetrazolyl or —P(O)(OH)$_2$, there can be formed the ammonium, morpholinium, sodium, potassium, barium, calcium salt, and the like, for use as the dosage form. When a basic group is present, such as amino or a basic heteroaryl radical, such as pyridyl, an acidic salt, such as hydrochloride, hydrobromide, phosphate, sulfate, trifluoroacetate, trichloroacetate, acetate, oxalate, maleate, pyruvate, malonate, succinate, citrate, tartarate, fumarate, mandelate, benzoate, cinnamate, methanesulfonate, ethane sulfonate, picrate and the like, and include acids related to the pharmaceutically acceptable salts listed in Journal of Pharmaceutical Science, 66, 2 (1977) and incorporated herein by reference, can be used as the dosage form.

Also, in the case of the —COOH or —P(O)(OH)$_2$ being present, pharmaceutically acceptable esters can be employed, e.g., methyl, tert-butyl, pivaloyloxymethyl, and the like, and those esters known in the art for modifying solubility or hydrolysis characteristics for use as sustained release or prodrug formulations. In addition, some of the compounds of the present invention may form solvates with water or common organic solvents. Such solvates are encompassed within the scope of the invention.

The term "therapeutically effective amount" shall mean that amount of drug or pharmaceutical agent that will elicit the biological or medical response of a tissue, system, animal, or human that is being sought by a researcher, veterinarian, medical doctor or other.

PREFERRED EMBODIMENTS OF THE INVENTION

In a preferred embodiment, the present invention is concerned with compounds of Formula 1

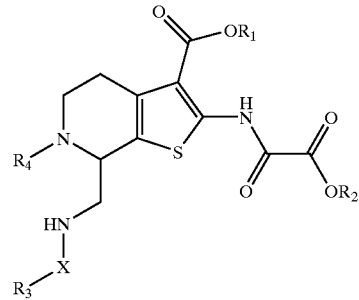

Formula 1 wherein

X is —C(O)— or —S(O)$_2$—;

$R_1$ and $R_2$ are independently hydrogen or a functional group that can be converted to hydrogen in vivo;

$R_3$ is $C_1$–$C_6$alkyl, $C_2$–$C_6$alkenyl, $C_2$–$C_6$alkynyl, aryl, aryl-$R_{10}$—, aryl-N($R_{35}$)—, aryl-$R_{11}$—N($R_{36}$)—, N($R_{37}$)($R_{38}$)—$R_{39}$—, $C_1$–$C_6$alkyloxy or aryl-$R_{13}$—O— wherein aryl is phenyl, biphenyl, indenyl, naphthyl, imidazolyl, 1,2,3-triazolyl, thiophenyl, pyridyl, quinolyl, isoquinolyl, benzofuranyl, indolyl or benzimidazolyl, which aryl group is optionally substituted with halogen, nitro, cyano, hydroxy, trihalomethyl, $C_1$–$C_6$alkyl, $R_{42}$—, $R_{42}$—$R_{14}$—, $C_1$–$C_6$alkyloxy, $R_{42}$—O—, $R_{42}$-S(O)$_2$—, $R_{42}$—$R_{15}$—O—, $R_{42}$—N($R_{16}$)—, $R_{18}$—C(O)—N($R_{19}$)—, $R_{40}$—C(O)—O—$R_{41}$—O—C(O)—, $R_{42}$—C(O)—N($R_{21}$)— or $R_{42}$—$R_{23}$—C(O)—N($R_{24}$)—; $R_4$ is hydrogen, $R_{27}$—O—C(O)—, aryl-$R_{28}$—O—C(O)—, $R_{29}$—C(O)—O—$R_{30}$—O—C(O)— or aryl-$R_{31}$—C(O)—O—$R_{32}$—O—C(O)— wherein aryl is phenyl, naphthyl or thiophenyl, which aryl group is optionally substituted with halogen, nitro, cyano, trihalomethyl, $R_{43}$—, $R_{43}$—$R_{33}$—, $C_1$–$C_6$alkyloxy or $R_{43}$—$R_{34}$—O—;

and wherein $R_5$, $R_7$, $R_8$, $R_9$, $R_{10}$, $R_{11}$, $R_{13}$, $R_{14}$, $R_{15}$, $R_{23}$, $R_{28}$, $R_{30}$, $R_{31}$, $R_{32}$, $R_{33}$, $R_{34}$, $R_{39}$, and $R_{41}$ independently are $C_1$–$C_6$alkylene, wherein $R_6$, $R_{12}$, $R_{17}$, $R_{18}$, $R_{20}$, $R_{22}$, $R_{25}$, $R_{27}$, $R_{29}$, and $R_{40}$ independently are $C_1$–$C_6$alkyl and wherein $R_{16}$, $R_{19}$, $R_{21}$, $R_{24}$, $R_{35}$, $R_{36}$, $R_{37}$ and $R_{38}$ independently are hydrogen or $C_1$–$C_6$alkyl, wherein $R_{42}$ and $R_{43}$ are independently phenyl, naphthyl or thiophenyl;

or a salt thereof with a pharmaceutically acceptable acid or base, or any optical isomer or mixture of optical isomers, including a racemic mixture, or any tautomeric form.

In another embodiment $R_1$ and $R_2$ are independently hydrogen, $C_1$–$C_6$alkyl, aryl-$R_5$—, $R_6$—C(O)—O—$R_7$— or aryl-$R_8$-C(O)—O—$R_9$— wherein aryl is phenyl, naphthyl or thiophenyl, which aryl group is optionally substituted with halogen, nitro, trihalomethyl, $C_1$–$C_6$alkyl or $C_1$–$C_6$alkyloxy;

In another embodiment X is C(O).

In another embodiment X is S(O)$_2$.

In another embodiment $R_1$ and $R_2$ are independently hydrogen, $C_1$–$C_6$alkyl, aryl-$R_5$—, or $R_6$—C(O)—O—$R_7$—, wherein aryl is phenyl, naphthyl or thiophenyl, which aryl group is optionally substituted with halogen, nitro, trihalomethyl, $C_1$–$C_6$alkyl or $C_1$–$C_6$alkyloxy.

In another embodiment $R_1$ and $R_2$ are independently hydrogen or $C_1$–$C_6$alkyl.

In another embodiment $R_1$ and $R_2$ are hydrogen.

In another embodiment $R_3$ is $C_1$–$C_6$alkyl, $C_2$–$C_6$alkenyl, $C_2$–$C_6$alkynyl, aryl, aryl-$R_{10}$—, aryl-N($R_{35}$)—, N($R_{37}$)($R_{38}$)—$R_{39}$—, or $C_1$–$C_6$alkyloxy wherein aryl is phenyl, biphenyl, indenyl, naphthyl, imidazolyl, 1,2,3-triazolyl, thiophenyl, pyridyl, quinolyl, isoquinolyl, indolyl or benzimidazolyl, which aryl group is optionally substituted with halogen, nitro, cyano, hydroxy, trihalomethyl, $C_1$–$C_6$alkyl, $R_{42}$—, $R_{42}$—$R_{14}$—, $C_1$–$C_6$alkyloxy, $R_{42}$—O—, $R_{42}$—S(O)$_2$—, $R_{42}$—$R_{15}$—O—, $R_{42}$—N($R_{16}$)—, $R_{18}$—C(O)—N($R_{19}$)—, $R_{40}$—C(O)—O—$R_{41}$—O—C(O)—, $R_{42}$—C(O)—N($R_{21}$)— or $R_{42}$—$R_{23}$—C(O)—N($R_{24}$)—.

In another embodiment $R_3$ is $C_1$–$C_6$alkyl, aryl, aryl-$R_{10}$—, aryl-N($R_{35}$)—, or N($R_{37}$)($R_{38}$)—$R_{39}$—, wherein aryl is phenyl, biphenyl, indenyl, naphthyl, imidazolyl, 1,2,3-triazolyl, thiophenyl, pyridyl, quinolyl, isoquinolyl, indolyl or benzimidazolyl, which aryl group is optionally substituted with halogen, nitro, cyano, hydroxy, trihalomethyl, $C_1$–$C_6$alkyl, $R_{42}$—, $R_{42}$—$R_{14}$—, $C_1$–$C_6$alkyloxy, $R_{42}$—O—, $R_{42}$—S(O)$_2$—, $R_{42}$—$R_{15}$—O—, $R_{42}$—N($R_{16}$)—, $R_{18}$—C(O)—N($R_{19}$)—, $R_{40}$—C(O)—$R_{41}$—O—C(O)—, $R_{42}$—C(O)—N($R_{21}$)— or $R_{42}$—$R_{23}$—C(O)—N($R_{24}$)—.

In another embodiment $R_3$ is aryl, aryl-$R_{10}$— or aryl-N($R_{35}$)—, wherein aryl is phenyl, biphenyl, indenyl, naphthyl, imidazolyl, 1,2,3-triazolyl, thiophenyl, pyridyl, quinolyl, isoquinolyl, indolyl or benzimidazolyl, which aryl group is optionally substituted with halogen, nitro, cyano, hydroxy, trihalomethyl, $C_1$–$C_6$alkyl, $R_{42}$—, $R_{42}$—$R_{14}$—, $C_1$–$C_6$alkyloxy, $R_{42}$—O—, $R_{42}$—S(O)$_2$—, $R_{42}$—$R_{15}$—O—, $R_{42}$—N($R_{16}$)—, $R_{18}$—C(O)—N($R_{19}$)—, $R_{40}$—C(O)—O—$R_{41}$—O—C(O)—, $R_{42}$—C(O)—N($R_{21}$)— or $R_{42}$—$R_{23}$—C(O)—N($R_{24}$)—.

In another embodiment $R_3$ is aryl, wherein aryl is phenyl, biphenyl, indenyl, naphthyl, imidazolyl, 1,2,3-triazolyl, thiophenyl, pyridyl, quinolyl, isoquinolyl, indolyl or benzimidazolyl, which aryl group is optionally substituted with halogen, nitro, cyano, hydroxy, trihalomethyl, $C_1$–$C_6$alkyl, $R_{42}$—, $R_{42}$—$R_{14}$—, $C_1$–$C_6$alkyloxy, $R_{42}$—O—, $R_{42}$—S(O)$_2$—, $R_{42}$—$R_{15}$—O—, $R_{42}$—N($R_{16}$)—, $R_{18}$—C(O)—N($R_{19}$)—, $R_{40}$—C(O)—O—$R_{41}$—O—C(O)—, $R_{42}$—C(O)—N($R_{21}$)— or $R_{42}$—$R_{23}$—C(O)—N($R_{24}$)—.

In another embodiment the aryl of $R_3$ is phenyl, biphenyl, naphtyl, 1,2,3-triazolyl, indolyl or benzimidazolyl.

In another embodiment the aryl of $R_3$ is phenyl, naphtyl, or indolyl.

In another embodiment the aryl of $R_3$ is phenyl.

In another embodiment the aryl of $R_3$ is substituted by halogen, hydroxy, $C_1$–$C_6$alkyl, $R_{42}$—, $R_{42}$—$R_{14}$—, $C_1$–$C_6$alkyloxy, $R_{42}$—O—, $R_{18}$—C(O)—N($R_{19}$)—, $R_{40}$—C(O)——O—$R_{41}$—O—C(O)—, $R_{42}$—C(O)—N($R_{21}$)— or $R_{42}$—$R_{23}$—C(O)—N($R_{24}$)—.

In another embodiment the aryl of $R_3$ is substituted by hydroxy, $R_{42}$—, $R_{42}$—$R_{14}$—, $C_1$–$C_6$alkyloxy, or $R_{42}$—O—.

In another embodiment $R_{42}$ is phenyl or thiophenyl.

In another embodiment $R_4$ is hydrogen, $R_{27}$—O—C(O)—, or $R_{29}$—C(O)—O—$R_{30}$—O—C(O)— wherein aryl is phenyl, naphthyl or thiophenyl, which aryl group is optionally substituted with halogen, nitro, cyano, trihalomethyl, $R_{43}$—, $R_{43}$—$R_{33}$—, $C_1$–$C_6$alkyloxy or $R_{43}$—$R_{34}$—O—;

In another embodiment $R_4$ is hydrogen.

In another embodiment the aryl of $R_4$ is phenyl.

In another embodiment the aryl of $R_4$ is substituted by halogen, hydroxy, $R_{43}$—, or $C_1$–$C_6$alkyloxy.

In a preferred embodiment, the present invention is concerned with compounds Formula 1

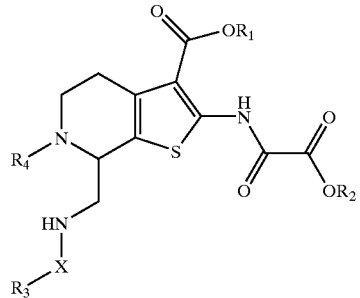

Formula 1 wherein

X is —C(O)—;

$R_1$ and $R_2$ are independently hydrogen, $C_1$–$C_6$alkyl, aryl-$R_5$—, $R_6$—C(O)—O—$R_7$— or aryl-$R_8$—C(O)—O—$R_9$— wherein aryl is phenyl, naphthyl, thiophenyl, which aryl group is optionally substituted with halogen, trihalomethyl, aryl, aryl-$R_{14}$—, $C_1$–$C_6$alkyloxy or aryl-$R_{15}$—O—;

$R_3$ is $C_1$–$C_6$alkyl, $C_2$–$C_6$alkenyl, $C_2$–$C_6$alkynyl, aryl, aryl-$R_{10}$—, aryl-N($R_{35}$)—, aryl-$R_{11}$—N($R_{36}$)—, N($R_{37}$)($R_{38}$)—$R_{39}$—, $C_1$–$C_6$alkyloxy or aryl-$R_{13}$—O— wherein aryl is phenyl, biphenyl, naphthyl, benzo[b]furanyl, 1,2,3-triazolyl, thiophenyl, pyridyl, quinolyl, isoquinolyl, or indolyl, which aryl group is optionally substituted with with halogen, hydroxy, $C_1$–$C_6$alkyl, $R_{42}$—, $R_{42}$—$R_{14}$—, $C_1$–$C_6$alkyloxy, $R_{42}$—O—, $R_{42}$—$R_{15}$—O— $R_4$ is hydrogen, $C_1$–$C_6$alkyl, $R_{29}$—C(O)—O—$R_{30}$—O—C(O)— or aryl-$R_{31}$—C(O)—O—$R_{32}$—O—C(O)— wherein aryl is phenyl or thiophenyl, which aryl group is optionally substituted with halogen, nitro, cyano, trihalomethyl, $R_{43}$—, $R_{43}$—$R_{33}$—, $C_1$–$C_6$alkyloxy or $R_{43}$—$R_{34}$—O—;

or a salt thereof with a pharmaceutically acceptable acid or base, or any optical isomer or mixture of optical isomers, including a racemic mixture, or any tautomeric form.

More preferred compounds of the invention are compounds of Formula 1

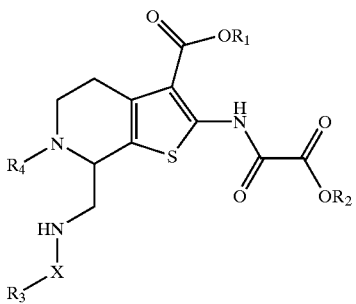

Formula 1 wherein
X is —C(O)—;
$R_1$ and $R_2$ are independently hydrogen or $C_1$–$C_6$alkyl;
$R_3$ is $C_1$–$C_6$alkyl, aryl-$R_{10}$, aryl, aryl-N($R_{35}$)—, or aryl-$R_{13}$—O— wherein aryl is phenyl, biphenyl, naphthyl, benzo[b]furanyl, 1,2,3-triazolyl, thiophenyl, pyridyl, quinolyl, isoquinolyl, or indolyl, which aryl group is optionally substituted with halogen, hydroxy, $C_1$–$C_6$alkyl, $R_{42}$—, $R_{42}$—$R_{14}$—, $C_1$–$C_6$alkyloxy, $R_{42}$—O—, $R_{42}$—$R_{15}$—O—;
$R_4$ is hydrogen, $R_{29}$—C(O)—O—$R_{30}$—O—C(O)— or aryl-$R_{31}$—C(O)—O—$R_{32}$—O—C(O)— wherein aryl is phenyl or thiophenyl, which aryl group is optionally substituted with halogen, nitro, cyano, trihalomethyl, $R_{43}$—, $R_{43}R_{33}$—, $C_1$–$C_6$alkyloxy or $R_{43}$—$R_{34}$—O—;
or a salt thereof with a pharmaceutically acceptable acid or base, or any optical isomer or mixture of optical isomers, including a racemic mixture, or any tautomeric form.

Even more preferred compounds of the invention are compounds of Formula 1

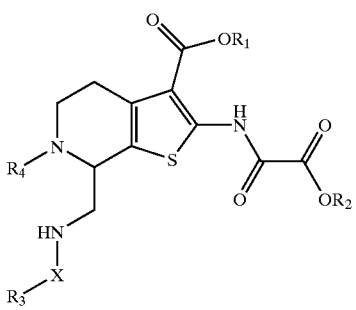

Formula 1 wherein
X is —C(O)—;
$R_1$, $R_2$ and $R_4$ are hydrogen;
$R_3$ is $C_1$–$C_6$alkyl, aryl, aryl-$R_{10}$—, aryl-N($R_{35}$)—, or aryl-$R_{13}$—O— wherein aryl is phenyl, biphenyl, naphthyl, 1,2,3-triazolyl, thiophenyl, pyridyl, quinolyl, isoquinolyl, or indolyl, which aryl group is optionally substituted with halogen, hydroxy, $C_1$–$C_6$alkyl, $R_{42}$—, $R_{42}$–$R_{14}$—, $C_1$–$C_6$alkyloxy, $R_{42}$—O, $R_{42}$—$R_{15}$—O—;
or a salt thereof with a pharmaceutically acceptable acid or base, or any optical isomer or mixture of optical isomers, including a racemic mixture, or any tautomeric form.

The following compounds are preferred:
7-(Benzoylamino-methyl)-2-(oxalyl-amino)-4,5,6,7-tetrahydro-thieno[2,3-c]pyridine-3-carboxylic acid;
7-(((1H-Indole-3-carbonyl)amino)methyl)-2-(oxalyl-amino)-4,5,6,7-tetrahydro-thieno[2,3-c]pyridine-3-carboxylic acid;
7-(((5-Hydroxy-1H-indole-2-carbonyl)amino)methyl)-2-(oxalyl-amino)-4,5,6,7-tetrahydro-thieno[2,3-c]pridine-3-carboxylic acid;
7-(((5-Methyl-2-phenyl-2H-[1,2,3]triazole-4-carbonyl)amino)methyl)-2-(oxalyl-amino)-4,5,6,7-tetrahydro-thieno[2,3-c]pyridine-3-carboxylic acid;
7-((4-Ethoxy-2-hydroxy-benzoylamino)methyl)-2-(oxalyl-amino)-4,5,6,7-tetrahydro-thieno[2,3-c]pyidine-3-carboxylic acid;
7-((4-Benzoylamino-benzoylamino)methyl)-2-(oxalyl-amino)-4,5,6,7-tetrahydro-thieno[2,3-c]pyridine-3-carboxylic acid;
7-(((Biphenyl-4-carbonyl)amino)methyl)-2-(oxalyl-amino)-4,5,6, 7-tetrahydro-thieno[2,3-c]pyridine-3-carboxylic acid;
7-(((5-Methoxy-1H-indole-2-carbonyl)amino)methyl)-2-(oxalyl-amino)-4,5,6,7-tetrahydro-thieno[2,3-c]pyridine-3-carboxylic acid;
7-((3-Biphenyl-4-yl-propionylamino)methyl)-2-(oxalyl-amino)-4,5,6,7-tetrahydro-thieno[2,3-c]-pyridine-3-carboxylic acid;
7-(((1H-Indole-2-carbonyl)amino)methyl)-2-(oxalyl-amino)-4,5,6,7-tetrahydro-thieno[2,3-c]pyridine-3-carboxylic acid;
7-((4-Benzyl-benzoylamino)methyl)-2-(oxalyl-amino)-4,5,6,7-tetrahydro-thieno[2,3-c]pyridine-3-carboxylic acid;
7-(((Naphthalene-1-carbonyl)amino)methyl)-2-(oxalyl-amino)-4,5,6,7-tetrahydro-thieno[2,3-c]pyridine-3-carboxylic acid;
7-((3-Naphthalen-2-yl-propionylamino)methyl)-2-(oxalyl-amino)-4,5,6,7-tetrahydro-thieno[2,3-c]pyridine-3-carboxylic acid;
7-(((2-Hydroxy-naphthalene-1-carbonyl)amino)methyl)-2-(oxalyl-amino)-4,5,6,7-tetrahydro-thieno[2,3-c]pyridine-3-carboxylic acid;
7-(((2-Ethoxy-naphthalene-1-carbonyl)amino)methyl)-2-(oxalyl-amino)-4,5,6,7-tetrahydro-thieno[2,3-c]pyridine-3-carboxylic acid;
7-(S)-((4-Benzenesulfonyl-benzoylamino)methyl)-2-(oxalyl-amino)-4,5,6,7-tetrahydro-thieno[2,3-c]pyridine-3-carboxylic acid;
7-(S)-(((Naphthalene-2-carbonyl)amino)methyl)-2-(oxalyl-amino)-4,5,6,7-tetrahydro-thieno[2, 3-c]pyridine-3-carboxylic acid;
2-(Oxalyl-amino)-7-(S)-((3-phenoxy-benzoylamino)methyl]-4,5,6,7-tetrahydro-thieno[2,3-c]pyridine-3-carboxylic acid;
2-(Oxalyl-amino)-7-(S)-((4-phenyl-butyrylamino)methyl)-4,5,6,7-tetrahydro-thieno[2,3-c]pyridine-3-carboxylic acid;
7-(S)-(((7-Ethoxy-benzofuran-2-carbonyl)amino)methyl)-2-(oxalyl-amino)-4,5,6,7-tetrahydro-thieno[2,3-c]pyridine-3-carboxylic acid;
7-(S)-(((4'-Hydroxy-biphenyl-4-carbonyl)amino)methyl)-2-(oxalyl-amino)-4,5,6,7-tetrahydro-thieno[2,3-c]pyridine-3-carboxylic acid;
7-(S)-((4-Acetylamino-benzenesulfonylamino)methyl)-2-(oxalyl-amino)-4,5,6,7-tetrahydro-thieno[2,3-c]pyridine-3-carboxylic acid;
7-(S)-(((5-Methoxy-benzofuran-2-carbonyl)amino)methyl)-2-(oxalyl-amino)-4,5,6,7-tetrahydro-thieno[2,3-c]pyridine-3-carboxylic acid;
7-(S)-(((3H-Benzoimidazole-5-carbonyl)amino)methyl)-2-(oxalyl-amino)-4,5,6,7-tetrahydro-thieno[2,3-c]pyridine-3-carboxylic acid;
7-(S)-(((5-Hydroxy-1H-indole-2-carbonyl)amino)methyl)-2-(oxalyl-amino)-4,5,6,7-tetrahydro-thieno[2,3-c]pyridine-3-carboxylic acid;
7-(R)-(((5-Hydroxy-1H-indole-2-carbonyl)amino)methyl)-2-(oxalyl-amino)-4,5,6,7-tetrahydro-thieno[2,3-c]pyridine-3-carboxylic acid;

7-(R)-(((1-Benzyl-1H-indole-3-carbonyl)amino)methyl)-2-(oxalyl-amino)-4,5,6,7-tetrahydro-thieno[2,3-c]pyridine-3-carboxylic acid;

2-(Oxalyl-amino)-7-(S)-((4-phenoxy-benzylamino)methyl)-4,5,6,7-tetrahydro-thieno[2,3-c]pyridine-3-carboxylic acid;

2-(Oxalyl-amino)-7-(S)-(3-(4-phenoxy-phenyl)ureidomethyl)-4,5,6,7-tetrahydro-thieno[2,3-c]pyridine-3-carboxylic acid;

7-(((1-Benzyl-1H-indole-3-carbonyl)amino)methyl)-2-(oxalyl-amino)-4,5,6,7-tetrahydro-thieno[2,3-c]pyridine-3-carboxylic acid;

7-(((1-Benzyl-1H-indole-3-carbonyl)amino)methyl)-6-methyl-2-(oxalyl-amino)-4,5,6,7-tetrahydro-thieno[2,3-c]pyridine-3-carboxylic acid;

7-(Acetylamino-methyl)-2-(oxalyl-amino)-4,5,6,7-tetrahydro-thieno[2,3-c]pyridine-3-carboxylic acid;

7-((5-Amino-5-methyl-hexanoylamino)methyl)-2-(oxalyl-amino)-4,5,6,7-tetrahydro-thieno[2,3-c]pyridine-3-carboxylic acid;

7-(S)-(((5-Fluoro-1H-indole-2-carbonyl)amino)methyl)-2-(oxalyl-amino)-4,5,6,7-tetrahydro-thieno[2,3-c]pyridine-3-carboxylic acid;

7-(S)-(((5-Hydroxy-1H-indole-2-carbonyl)amino)methyl)-2-(oxalyl-amino)-4,7-dihydro-5H-thieno[2,3-c]pyridine-3,6-dicarboxylic acid 6-acetoxymethyl ester;

7-(S)-(((5-Acetoxymethoxycarbonyloxy-1H-indole-2-carbonyl)amino)methyl)-2-(oxalyl-amino)-4,7-dihydro-5H-thieno[2,3-c]pyridine-3,6-dicarboxylic acid 6-acetoxymethyl ester;

2-(Oxalyl-amino)-7-(S)-((([1,1';3',1"]terphenyl-4-carbonyl)aminomethyl)-4,5,6,7-tetrahydro-thieno[2,3-c]pyridine-3-carboxylic acid;

7-(S)-(((1H-Indole-2-carbonyl)amino)methyl)-2-(oxalyl-amino)-4,5,6,7-tetrahydro-thieno[2,3-c]pyridine-3-carboxylic acid;

2-(Ethoxyoxalyl-amino)-7-(((5-hydroxy-1H-indole-2-carbonyl)amino)methyl)-4,5,6,7-tetrahydro-thieno[2,3-c]pyridine-3-carboxylic acid;

2-(Ethoxyoxalyl-amino)-7-(((5-hydroxy-1H-indole-2-carbonyl)amino)methyl)-4,5,6,7-tetrahydro-thieno[2,3-c]pyridine-3-carboxylic acid ethyl ester;

2-((2,2-Dimethyl-propoxyoxalyl)amino)-7-(((5-hydroxy-1H-indole-2-carbonyl)-amino)methyl)-4,5,6,7-tetrahydro-thieno[2,3-c]pyridine-3-carboxylic acid ethyl ester;

7-(((5-Hydroxy-1H-indole-2-carbonyl)amino)methyl)-2-(oxalyl-amino)-4,7-dihydro-5H-thieno[2,3-c]pyridine-3-carboxylic acid ethyl ester;

7-(((5-Hydroxy-1H-indole-2-carbonyl)amino)methyl)-2-(oxalyl-amino)-4,7-dihydro-5H-thieno[2,3-c]pyridine-3,6-dicarboxylic acid 6-ethyl ester;

or a pharmaceutically acceptable salt thereof.

In another embodiment $R_1$ is hydrogen.

In another embodiment $R_2$ is hydrogen.

In another embodiment $R_1$ and $R_2$ are hydrogen.

In another embodiment $R_4$ is hydrogen.

In another embodiment $R_1$, $R_2$ and $R_4$ are hydrogen.

In another embodiment $R_4$ is $R_{29}$—C(O)—O—$R_{30}$—O—C(O)—; wherein $R_{29}$ and $R_{30}$ are as defined in claim 1.

In another embodiment $R_4$ is aryl-$R_{31}$—C(O)—O—$R_{32}$—O—C(O)—, wherein $R_{31}$ and $R_{32}$ are as defined in claim 1 and the aryl group is optionally substituted as defined in claim 1.

In another embodiment $R_3$ is aryl as defined in claim 1.

In another embodiment the aryl of $R_3$ group is 2-hydroxyphenyl.

In another embodiment the aryl group of $R_3$ is 4-ethoxy-2-hydroxy-phenyl and X is —C(O)—.

In another embodiment the aryl group of $R_3$ is 4-benzoyl-amino-phenyl and X is —C(O)—.

In another embodiment the aryl group of $R_3$ is 4-biphenyl and X is —C(O)—.

In another embodiment the aryl group of $R_3$ is 3-phenoxy-phenyl and X is —C(O)—.

In another embodiment $R_4$ is $R_{29}$—C(O)—Q—$R_{30}$—O—C(O)—; wherein $R_{29}$ and $R_{30}$ are as defined in claim 1.

In another embodiment the aryl group of $R_3$ 4-benzenesulfonyl-phenyl and X is —C(O)—.

In another embodiment the aryl group of $R_3$ is naphthyl; wherein the naphthyl group is optionally substituted as defined in claim 1.

In another embodiment the aryl group of $R_3$ is 2-hydroxy-naphthyl and X is —C(O)—.

In another embodiment the aryl group of $R_3$ is 2-ethoxy-naphthyl and X is —C(O)—.

In another embodiment the aryl group of $R_3$ is 1H-indolyl; where in the 1H-indolyl group is optionally substituted as defined in claim 1.

In another embodiment the aryl group of $R_3$ is 1H-indol-2-y and X is —C(O)—.

In another embodiment the aryl group of $R_3$ is 5-methoxy-1H-indol-2-yl and X is —C(O)—.

In another embodiment the aryl group of $R_3$ is 5-hydroxy-1H-indol-2-yl and X is —C(O)—.

In another embodiment the aryl group of $R_3$ is benzimidazolyl; wherein the benzimidazolyl group is optionally substituted as defined in claim 1.

In another embodiment the aryl group of $R_3$ is 5-methoxy-benzimidazol-2-yl.

In another embodiment the aryl group of $R_3$ is 7-ethoxy-benzimidazol-2-yl.

In another embodiment the aryl group of $R_3$ is 1,2,3-triazolyl; wherein the 1,2,3-triazolyl group is optionally substituted as defined in claim 1.

In another embodiment the aryl group of $R_3$ is 5-methyl-2-phenyl-2H-[1,2,3]triazolyl and X is —C(O)—.

In another embodiment the aryl group of $R_3$ is 4-acetylamino-phenyl and X is —SO$_2$—.

In another embodiment $R_3$ is aryl-$R_{13}$—O—; wherein $R_{13}$ is as defined in claim 1 and the aryl group is optionally substituted as defined in claim 1.

In another embodiment the aryl group of $R_3$ is phenyl.

In another embodiment $R_3$ is aryl-N($R_{35}$); wherein $R_{35}$ is as defined in claim 1 and the aryl group is optionally substituted as defined in claim 1.

In another embodiment the aryl group of $R_3$ is 4-phenoxyphenyl and X is —C(O)—.

In another embodiment $R_3$ is aryl-$R_{10}$—; wherein the aryl group is optionally substituted as defined in claim 1.

In another embodiment the aryl group of $R_3$ is phenyl and X is —C(O)—.

In another embodiment the aryl group of $R_3$ is biphenyl and X is —C(O)—.

In another embodiment the aryl group of $R_3$ is naphthyl and X is —C(O)—.

In another embodiment the compounds of the invention act as inhibitors of Protein Tyrosine Phosphatases.

Another aspect of the invention is a pharmaceutical composition comprising a compound of the invention or a pharmaceutically acceptable salt thereof with a pharmaceutically acceptable acid or base, or any optical isomer or mixture of optical isomers, including a racemic mixture, or any tautomeric form together with one or more pharmaceutically acceptable carriers or diluents.

Another aspect of the invention is a pharmaceutical composition suitable for treating type 1 diabetes, type 2 diabetes, impaired glucose tolerance, insulin resistance or obesity comprising a compound of the invention or a pharmaceutically acceptable salt thereof with a pharmaceutically acceptable acid or base, or any optical isomer or mixture of optical isomers, including a racemic mixture, or any tautomeric form together with one or more pharmaceutically acceptable carriers or diluents.

Another aspect of the invention is a pharmaceutical composition suitable for treating immune dysfunctions including autoimmunity, diseases with dysfunctions of the coagulation system, allergic diseases, osteoporosis, proliferative disorders including cancer and psoriasis, diseases with decreased or increased synthesis or effects of growth hormone, diseases with decreased or increased synthesis of hormones or cytokines that regulate the release of/or response to growth hormone, diseases of the brain including Alzheimer's disease and schizophrenia, and infectious diseases comprising a compound of the invention or a pharmaceutical acceptable salt thereof with a pharmaceutically acceptable acid or base, or any optical isomer or mixture of optical isomers, including a racemic mixture, or any tautomeric form together with one or more pharmaceutically acceptable carriers or diluents.

Another aspect of the invention is a pharmaceutical composition of the invention in the form of an oral dosage unit or parenteral dosage unit.

Another aspect of the invention is a pharmaceutical composition of the invention wherein said compound is administered as a dose in a range from about 0.05 to 1000 mg, preferably from about 0.1 to 500 mg and especially in the range from 50 to 200 mg per day.

Another aspect of the invention is a compound of the invention or a pharmaceutically acceptable salt thereof with a pharmaceutically acceptable acid or base, or any optical isomer or mixture of optical isomers, including a racemic mixture, or any tautomeric form for therapeutical use.

Another aspect of the invention is a compound of the invention or a pharmaceutically acceptable salt thereof with a pharmaceutically acceptable acid or base, or any optical isomer or mixture of optical isomers, including a racemic mixture, or any tautomeric form for therapeutical use in the treatment or preventing of type 1 diabetes, type 2 diabetes, impaired glucose tolerance, insulin resistance or obesity.

Another aspect of the invention is a compound of the invention or a pharmaceutically acceptable salt thereof with a pharmaceutically acceptable acid or base, or any optical isomer or mixture of optical isomers, including a racemic mixture, or any tautomeric form for therapeutical use in the treatment or preventing of immune dysfunctions including autoimmunity, diseases with dysfunctions of the coagulation system, allergic diseases, osteoporosis, proliferative disorders including cancer and psoriasis, diseases with decreased or increased synthesis or effects of growth hormone, diseases with decreased or increased synthesis of hormones or cytokines that regulate the release of/or response to growth hormone, diseases of the brain including Alzheimer's disease and schizophrenia, and infectious diseases.

Another aspect of the invention is the use of a compound of the invention or a pharmaceutically acceptable salt thereof with a pharmaceutically acceptable acid or base, or any optical isomer or mixture of optical isomers, including a racemic mixture, or any tautomeric form as a medicament.

Another aspect of the invention is the use of a compound of the invention for preparing a medicament.

Another aspect of the invention is the use of a compound of the invention or a pharmaceutically acceptable salt thereof with a pharmaceutically acceptable acid or base, or any optical isomer or mixture of optical isomers, including a racemic mixture, or any tautomeric form for the preparation of a medicament suitable for the treatment or preventing of type 1 diabetes, type 2 diabetes, impaired glucose tolerance, insulin resistance or obesity.

Another aspect of the invention is the use of a compound of the invention or a pharmaceutically acceptable salt thereof with a pharmaceutically acceptable acid or base, or any optical isomer or mixture of optical isomers, including a racemic mixture, or any tautomeric form for the preparation of a medicament suitable for the treatment or preventing of immune dysfunctions including autoimmunity, diseases with dysfunctions of the coagulation system, allergic diseases, osteoporosis, proliferative disorders including cancer and psoriasis, diseases with decreased or increased synthesis or effects of growth hormone, diseases with decreased or increased synthesis of hormones or cytokines that regulate the release of/or response to growth hormone, diseases of the brain including Alzheimer's disease and schizophrenia, and infectious diseases.

Another aspect of the invention is a method of treating type 1 diabetes, type 2 diabetes, impaired glucose tolerance, insulin resistance or obesity comprising administering to a subject in need thereof an effective amount of a compound of the invention to said subject.

Another aspect of the invention is a method of treating immune dysfunctions including autoimmunity, diseases with dysfunctions of the coagulation system, allergic diseases, osteoporosis, proliferative disorders including cancer and psoriasis, diseases with decreased or increased synthesis or effects of growth hormone, diseases with decreased or increased synthesis of hormones or cytokines that regulate the release of/or response to growth hormone, diseases of the brain including Alzheimer's disease and schizophrenia, and infectious diseases comprising administering to a subject in need thereof an effective amount of a compound of the invention to said subject.

Another aspect of the invention is a process for the manufacture of a medicament, particular to be used in the treatment or prevention of type 1 diabetes, type 2 diabetes, impaired glucose tolerance, insulin resistance or obesity which process comprising bringing a compound of the invention or a pharmaceutically acceptable salt thereof into a galenic dosage form.

Another aspect of the invention is a process for the manufacture of a medicament, particular to be used in the treatment or prevention of immune dysfunctions including autoimmunity, diseases with dysfunctions of the coagulation system, allergic diseases, osteoporosis, proliferative disorders including cancer and psoriasis, diseases with decreased or increased synthesis or effects of growth hormone, diseases with decreased or increased synthesis of hormones or cytokines that regulate the release of/or response to growth hormone, diseases of the brain including Alzheimer's disease and schizophrenia, and infectious diseases which process comprising bringing a compound of the invention or a pharmaceutically acceptable salt thereof into a galenic dosage form.

Another aspect of the invention is a method for preparing a compound of Formula 1, characterized in

A)

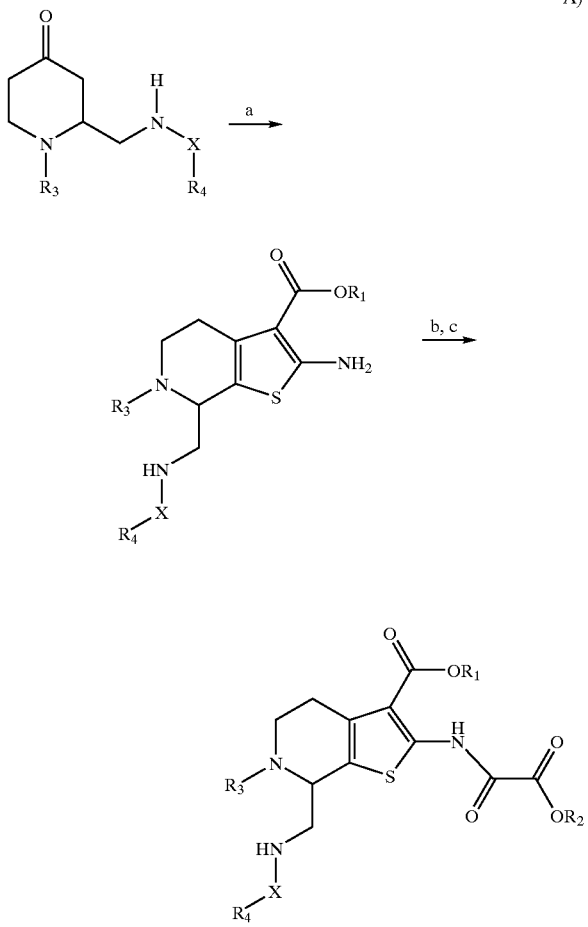

a) NC—CH$_2$—COOR$_1$, sulphur, morpholine or triethylamine, EtOH; b) R$_3$—O—C(O)—C(O)-imidazol-1-yl, THF; c) 25% TFA/CH$_2$Cl$_2$; wherein X, R$_1$, R$_2$, R$_3$, and R$_4$ are defined above.

The reaction step a) in Method A gives a mixture of regioisomers which can be separated by use of column chromatography known to those skilled in the art.

B)

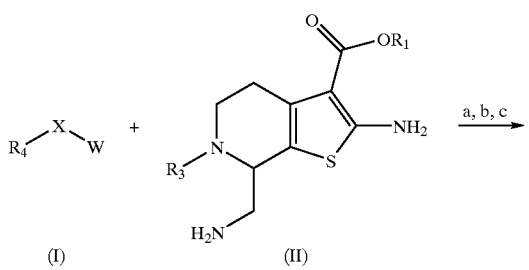

-continued

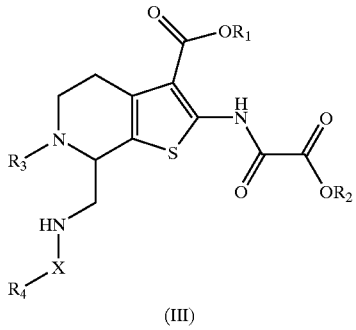

(III)

a) By allowing an activated carboxylic acid or sulfonic acid (I); wherein X is —C(CO)— and W is —OH, —OSO$_2$Me, halogen, R$_4$COO— or X is —SO$_2$— and W is chloride, a substituted 5-aminomethyl-tetrahydro-thieno[2,3-c]pyridine (II) to react under conditions known to those skilled in the art which favour amide or sulfonamide bond formation followed by b) R$_2$—O—C(O)—C(O)-imidazol-1-yl, THF and c) 25% TFA/CH$_2$Cl$_2$; to yield (III) wherein R$_1$, R$_2$, R$_3$, and R$_4$ are defined above.

Pharmacological Methods

The compounds are evaluated for biological activity with a truncated form of PTP1 B (corresponding to the first 321 amino acids), which was expressed in *E. coli* and purified to apparent homogeneity using published procedures well-known to those skilled in the art. The enzyme reactions are carried out using standard conditions essentially as described by Burke et al. (*Biochemistry* 35; 15989–15996 (1996)). The assay conditions are as follows. Appropriate concentrations of the compounds of the invention are added to the reaction mixtures containing different concentrations of the substrate, p-nitrophenyl phosphate (range: 0.16 to 10 mM—final assay concentration). The buffer used was 100 mM sodium acetate pH 5.5, 50 mM sodium chloride, 0.1% (w/v) bovine serum albumin and 5 mM dithiothreitol (total volume 100 ml). The reaction was started by addition of the enzyme and carried out in microtiter plates at 25° C. for 60 minutes. The reactions are stopped by addition of NaOH. The enzyme activity was determined by measurement of the absorbance at 405 nm with appropriate corrections for absorbance at 405 nm of the compounds and p-nitrophenyl phosphate. The data are analyzed using nonlinear regression fit to classical Michaelis Menten enzyme kinetic models. Inhibition is expressed as K$_i$ values in $\mu$M. The results of representative experiments are shown in Table 1.

TABLE 1

Inhibition of classical PTP1B by compounds of the invention

| Example no. | PTP1B K$_i$ values ($\mu$M) |
|---|---|
| 1 | 0.49 |
| 6 | 0.33 |
| 9 | 0.062 |
| 11 | 0.14 |
| 12 | 0.12 |
| 13 | 0.07 |
| 14 | 0.07 |
| 20 | 0.11 |
| 22 | 0.091 |
| 24 | 0.64 |
| 25 | 3.2 |
| 26 | 2.6 |

TABLE 1-continued

Inhibition of classical PTP1B by compounds of the invention

| Example no. | PTP1B $K_i$ values ($\mu$M) |
|---|---|
| 27 | 2.1 |
| 28 | 0.058 |
| 29 | 0.031 |
| 30 | 0.07 |
| 31 | 1.1 |
| 32 | 0.078 |
| 33 | 0.018 |
| 35 | 0.032 |
| 36 | 0.042 |
| 37 | 0.031 |
| 38 | 0.063 |
| 40 | 1.3 |
| 41 | 0.9 |
| 42 | 0.12 |
| 43 | 7.3 |
| 44 | 1.6 |
| 45 | 2 |

The Synthesis of the Compounds

In accordance with one aspect of the invention, the compounds of the invention are prepared as illustrated in the following reaction scheme:

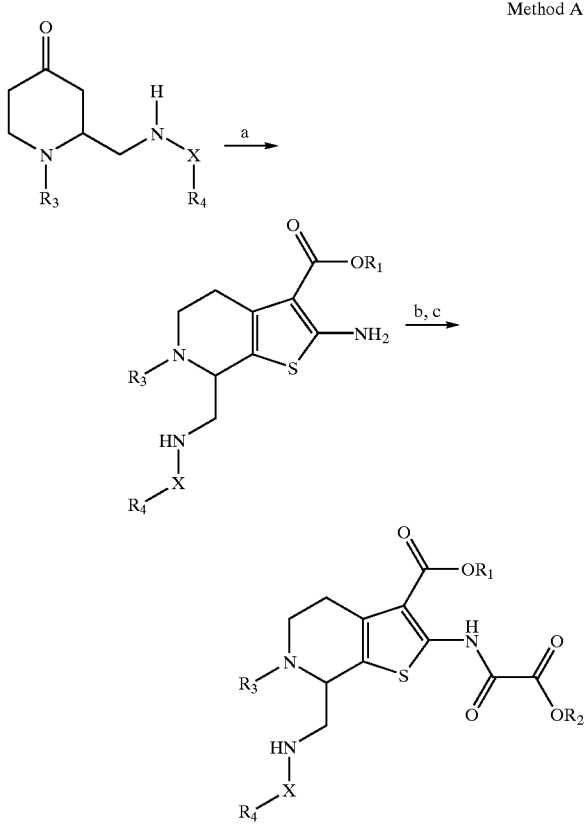

a) NC—CH$_2$—COOR$_1$, sulphur, morpholine or triethylamine, EtOH; b) R$_3$—O—C(O)—C(O)-imidazol-1-yl, THF; c) 25% TFA/CH$_2$Cl$_2$; wherein X, R$_1$, R$_2$, R$_3$, and R$_4$ are defined above.

The reaction step a) in Method A gives a mixture of regioisomers which can be separated by use of column chromatography known to those skilled in the art.

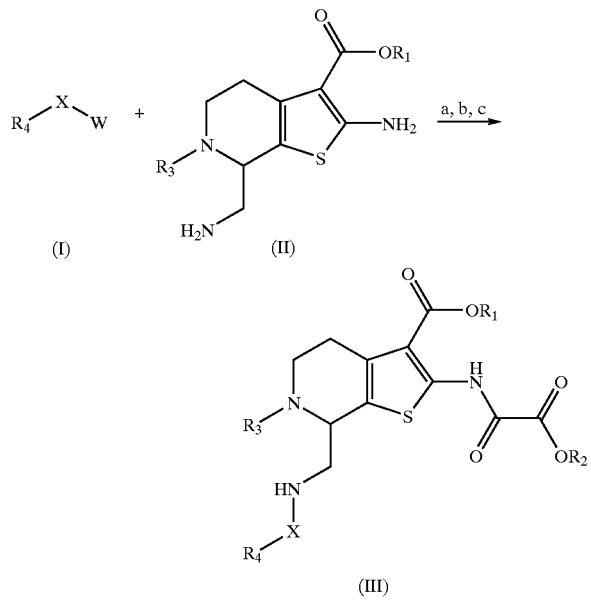

a) By allowing an activated carboxylic acid or sulfonic acid (I); wherein X is —C(CO)— and W is —OH, —OSO$_2$Me, halogen, R$_4$COO— or X is —SO$_2$— and W is chloride, a substituted 5-aminomethyl-tetrahydro-thieno[2,3-c]pyridine (II) to react under conditions known to those skilled in the art which favour amide or sulfon amide bond formation followed by b) R$_2$—O—C(O)—C(O)-imidazol-1-yl, THF and c) 25% TFA/CH$_2$Cl$_2$; to yield (III) wherein R$_1$, R$_2$, R$_3$, and R$_4$ are defined above.

Pharmacological Preparations

For the above indications the dosage will vary depending on the compound of the invention employed, on the mode of administration and on the therapy desired. However, in general, satisfactory results are obtained with a dosage of from about 0.5 mg to about 1000 mg, preferably from about 1 mg to about 500 mg of compounds of the invention, conveniently given from 1 to 5 times daily, optionally in sustained release form. Usually, dosage forms suitable for oral administration comprise from about 0.5 mg to about 1000 mg, preferably from about 1 mg to about 500 mg of the compounds of the invention admixed with a pharmaceutical carrier or diluent.

The compounds of the invention may be administered in a pharmaceutically acceptable acid addition salt form or where possible as a metal or a C$_{1-6}$-alkylammonium salt. Such salt forms exhibit approximately the same order of activity as the free acid forms.

This invention also relates to pharmaceutical compositions comprising a compound of the invention or a pharmaceutically acceptable salt thereof and, usually, such compositions also contain a pharmaceutical carrier or diluent. The compositions containing the compounds of this invention may be prepared by conventional techniques and appear in conventional forms, for example capsules, tablets, solutions or suspensions.

The pharmaceutical carrier employed may be a conventional solid or liquid carrier. Examples of solid carriers are lactose, terra alba, sucrose, talc, gelatine, agar, pectin, acacia, magnesium stearate and stearic acid. Examples of liquid carriers are syrup, peanut oil, olive oil and water.

Similarly, the carrier or diluent may include any time delay material known to the art, such as glyceryl monostearate or glyceryl distearate, alone or mixed with a wax.

If a solid carrier for oral administration is used, the preparation can be tabletted; placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatin capsule or sterile injectable liquid such as an aqueous or non-aqueous liquid suspension or solution.

Generally, the compounds of this invention are dispensed in unit dosage form comprising 10–200 mg of active ingredient in or together with a pharmaceutically acceptable carrier per unit dosage.

The dosage of the compounds according to this invention is 1–500 mg/day, e.g. about 100 mg per dose, when administered to patients, e.g. humans, as a drug.

A typical tablet that may be prepared by conventional tabletting techniques contains

| Core: | |
|---|---|
| Active compound (as free compound or salt thereof) | 100 mg |
| Colloidal silicon dioxide (Areosil ®) | 1.5 mg |
| Cellulose, microcryst. (Avicel ®) | 70 mg |
| Modified cellulose gum (Ac-Di-Sol ®) | 7.5 mg |
| Magnesium stearate | |
| Coating: | |
| HPMC approx. | 9 mg |
| *Mywacett ® 9–40 T approx. | 0.9 mg |

*Acylated monoglyceride used as plasticiser for film coating.

The route of administration may be any route, which effectively transports the active, compound to the appropriate or desired site of action, such as oral or parenteral e.g. rectal, transdermal, subcutaneous, intranasal, intramuscular, topical, intravenous, intraurethral, ophthalmic solution or an ointment, the oral route being preferred.

A number of procedures, well known to those skilled in the art, may be used to verify that the attached chemical groups have been removed or that the cyclic compound has been hydrolyzed after uptake in cells or mammals. An example, which is not intended in any way to limit the scope of the invention, is given in the following. A mammalian cell line, which can be obtained from the American Tissue Type Collection or other similar governmental or commercial sources, is incubated with said modified compound. After incubation at conditions well known to those skilled in the art, the cells are washed appropriately, lysed and the lysate is isolated. Appropriate controls, well known to those skilled in the art, must be included. A number of different procedures, well known to those skilled in the art, may in turn be used to extract and purify said compound from said lysate. Said compound may or may not retain the attached chemical group or said cyclic compound may or may not have been hydrolyzed. Similarly, a number of different procedures—well known to those skilled in the art—may be used to structurally and chemically characterize said purified compound. Since said purified compound has been isolated from said cell lysate and hence has been taken up by said cell line, a comparison of said structurally and chemically characterized compound with that of the original unmodified compound (i.e. without said attached chemical group or said non-cyclic compound) will immediately provide those skilled in the art information on whether the attached chemical group as been removed in the cell or if the cyclic compound has been hydrolyzed. As a further analysis, said purified compound may be subjected to enzyme kinetic analysis as described in detail in the present invention. If the kinetic profile is similar to that of the original compound without said attached chemical group, but different from said modified compound, this confirms that said chemical group has been removed or said cyclic compounds has been hydrolyzed. Similar techniques may be used to analyze compounds of the invention in whole animals and mammals.

EXAMPLES

The process for preparing compounds of Formula 1 and preparations containing them is further illustrated in the following examples, which, however, are not to be construed as limiting.

Hereinafter, TLC is thin layer chromatography, CDCl$_3$ is deuterio chloroform, CD$_3$OD is tetradeuterio methanol and DMSO-d$_6$ is hexadeuterio dimethylsulfoxide. The structures of the compounds are confirmed by either elemental analysis or NMR, where peaks assigned to characteristic protons in the title compounds are presented where appropriate. $^1$H NMR shifts ($\delta_H$) are given in parts per million (ppm) down field from tetramethylsilane as internal reference standard. M.p.: is melting point and is given in ° C. and is not corrected. Column chromatography was carried out using the technique described by W. C. Still et al., *J. Org. Chem.* 43: 2923 (1978) on Merck silica gel 60 (Art. 9385). The RP-HPLC analysis was performed using UV detections at 214, 254, 276, and 301 nm on a Vydac 218TP54 4.6 mm×250 mm 5$\mu$ C-18 silica column (The Seperations Group, Hesperia), which was eluted at 1 ml/min at 42° C.

Three different elution conditions were used:

Method A1: The column was equilibrated with a buffer consisting of 0.1 M ammonium sulfate, which was adjusted to pH 2.5 with 4M sulfuric acid after injection the sample was eluted by a gradient of 0% to 60% acetonitrile in the same buffer during 50 min.

Method B1: The column was equilibrated with 0.1% TFA/water and eluted by a gradient of 0.1% TFA/water to 60% acetonitrile/0.1% TFA/water during 50 min.

Method B6: The column was equilibrated with 0.1% TFA/water and eluted by a gradient of 0.1% TFA/water to 90% acetonitrile/0.1% TFA/water during 50 min. Compounds used as starting material are either known compounds or compounds, which can readily be prepared by methods known per se.

Example 1

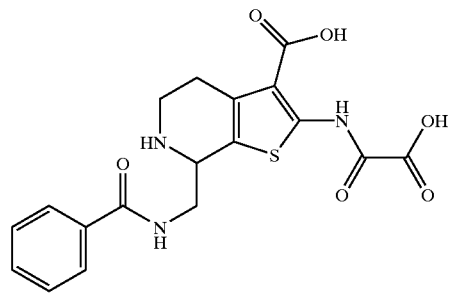

7-(Benzoylamino-methyl)-2-(oxalyl-amino)-4,5,6,7-tetrahydro-thieno[2,3-c] pyridine-3-carboxylic acid Phthalimidoacetaldehyde diethyl acetal (100 g, 0.38 mol) and 1 N hydrochloric acid (600 ml) was mixture was stirred at reflux temperature for 5 min. or until a homogeneous solution is obtained. The reaction mixture was cooled and the precipitate was filtered off and dried in vacuo at 50° C. for 16 hours, which afforded 63.3 g (88%) of phthalimido-acetaldehyde as a solid.

$^1$H-NMR (300 MHz, CDCl$_3$): δ 4.58 (s, 2H), 7.76–7.78 (m, 2H), 7.90–7.92 (m, 2H), 9.67 (s, 1H).

A dry 250 ml round bottom flask was charged with 4Å molecular sieves (15 g), phthalimidoacetyl aldehyde (17.3 g, 91.5 mmol), 150 ml of dry dichloromethane, and 4-methoxybenzylamine (11.94 ml, 0.092 mol). The reaction was stirred at room temperature, under nitrogen for 1 hour. The reaction mixture was filtered and 2-trimethylsilyloxy-1,3-butadiene (20.92 ml, 0.12 moles) was added. This mixture was added slowly to a mixture of aluminum chloride (14.64 g, 0.11 moles) and dichloromethane (100 ml) at −78° C. Once the addition was complete, the mixture was allowed to stir for 18 hours, slowly warming to room temperature. The reaction mixture was cooled to 0° C. and 1N hydrochloric acid (100 ml) was added slowly. Once the addition was complete the reaction mixture was allowed to stir for 2 hours. Water (500 ml) was added and the product extracted with dichloromethane. The aqueous layer was basified with sodium carbonate and extracted with dichloromethane. The combined organic fractions were washed with brine (2×) and dried (MgSO$_4$), filtered and the solvent evaporated in vacuo. The solid residue (35 g) was subjected to flash chromatography using a mixture of hexanes/ethyl acetate (1:1) as eluent, which afforded 11.8 g (Rf=0.4, 60 hexanes/40 ethyl acetate) of 2-(1-(4-methoxy-benzyl)-4-oxo-piperidin-2-ylmethyl)-isoindole-1,3-dione. 4.6 g of 2-(1-(4-methoxy-benzyl)-4-trimethyl-silanyloxy-1,2,3,6-tetrahydro-pyridin-2-ylmethyl)-isoindole-1,3-dione (R$_f$=0.87, 60 hexanes/40 ethyl acetate) was also obtained which was stirred with 1N hydrochloric acid for 2 hours. The solution was basified with sodium carbonate and extracted with dichloromethane. The organic layer was washed with brine and subjected to flash chromatography to yield 1.0 g of 2-(1-(4-methoxy-benzyl)-4-oxo-piperidin-2-ylmethyl)-isoindole-1,3-dione.

$^1$H-NMR (CDCl$_3$): δ 7.83 (m, 2H), 7.74 (m, 2H), 7.02 (d, 2H, J=8.7 Hz), 6.59 (d, 2H, J=8.7), 3.94 (ddd, 2H, J=12 Hz, J=12 Hz, J=4 Hz), 3.81 (d, 2H, J=12.3 Hz), 3.74 (s, 3H), 3.54-3.49 (m, 1H), 3.46-3.40 (m, 1H), 2.95 (dt,1H, J=5.1 Hz, 3.3 Hz), 2.72-2.65 (m, 1H), 2.53 (ddd, 1H, J=15.6 Hz, J=10.2 Hz, J=6 Hz), 2.33-2.31 (m, 1H), 2.28-2.26 (m, 1H). LC-MS: R$_t$=2.08 min, m/z: 379.2 [M+H]$^+$ To a solution of 2-(1-(4-methoxy-benzyl)-4-oxo-piperidin-2-ylmethyl)-isoindole-1,3-dione (20.0 g, 52.9 mmol) in absolute ethanol (350 ml) flushed with nitrogen was added sulfur (1.90 g, 59.2 mmol), tert-butyl cyano acetate (9.7 g, 68.7 mmol), and morpholine (9.2 ml, 105.6 mmol). Stirring was commenced as the reaction was heated to 50° C for 20 hours. A precipitate was filtered off and washed with cold acetonitrile affording 9.5 g (34%) of 2-amino-7-(1,3-dioxo-1,3-dihydro-isoindol-2-ylmethyl)-6-(4-methoxy-benzyl)-4,5,6,7-tetrahydro-thieno[2,3-c]pyridine-3-carboxylic acid tert-butyl ester. The mother liquors was evaporated in vacuo affording an oil which was purification by silica gel chromatography using a mixture of hexanes/ethyl acetate (3:1) as eluent, which afforded 10.5 g (37%) of a 9:1 mixture of 2-amino-7-(1,3-dioxo-1,3-dihydro-isoindol-2-ylmethyl)-6-(4-methoxy-benzyl)-4,5,6,7-tetrahydro-thieno[2,3-c]pyridine-3-carboxylic acid tert-butyl ester (A) and 2-amino-5-(1,3-dioxo-1,3-dihydro-isoindol-2-ylmethyl)-6-(4-methoxy-benzyl)4,5,6,7-tetrahydro-thieno[2,3-c]pyridine-3-carboxylic acid tert-butyl ester (B).

(A): $^1$H-NMR (400 MHz, CDCl$_3$): δ 7.88-7.70 (m, 4H), 6.84 (d, 2H, J=7 Hz), 6.33 (d, 2H, J=9 Hz), 6.02 (s, 2H), 4.65-2.62 (m, 12H), 1.58 (s, 9H).

(B): $^1$H-NMR (400 MHz, CDCl$_3$): δ 7.86 (m, 2H), 7.74 (m, 2H), 7.07 (d, 2H, J=9 Hz), 6.70 (d, 2H, J=9 Hz), 5.94 (s, 2H), 4.07 (d, 1H, J=10 Hz), 3.86-3.73 (m, 6H), 3.68-3.40 (m, 5H), 2.87 (dd, 1H, J=19 Hz, J=5 Hz), 2.65 (dd, 1H, J=19 Hz, J=5 Hz), 1.53 (s, 9H).

In a 500 ml round-bottom flask, a suspension of 2-amino-7-(1,3-dioxo-1,3-dihydro-isoindol-2-ylmethyl)-6-(4-methoxy-benzyl)-4,5,6,7-tetrahydro-thieno[2,3-c]pyridine-3-carboxylic acid tert-butyl ester (5.00 g, 9.4 mmol) in absolute ethanol (200 ml) was flushed with nitrogen. The reaction mixture was stirred at room temperature and hydrazine (1.5 ml, 47.8 mmol) was added. The reaction mixture was heated to 80° C. for 6 hours and then cooled to room temperature. After 14 hours at room temperature, the precipitate was filtered off and washed with absolute ethanol. The mother liquid was concentrated in vacuo and the residue was dissolved in dichloromethane (75 ml) and refiltered to remove an additional precipitate. Concentration of the mother liquid afforded 3.2 g (85%) of 2-amino-7-aminomethyl-6-(4-methoxy-benzyl)-4,5,6,7-tetrahydro-thieno[2,3-c]pyridine-3-carboxylic acid tert-butyl ester as a solid.

$^1$H-NMR (300 MHz, CDCl$_3$): δ 7.27 (d, 2H, J=9 Hz), 6.88 (d, 2H, J=9 Hz), 6.01 (s, 2H), 3.81 (s, 3H), 3.78 (d, 1H, J=14 Hz), 3.62 (d, 1H, J=14 Hz), 3.46 (m, 1H), 3.12-2.70 (m, 5H), 2.60 (m, 1H), 1.55 (s, 9H). 2-Amino-7-aminomethyl-6-(4-methoxy-benzyl)-4,5,6,7-tetrahydro-thieno[2,3-c]pyridine-3-carboxylic acid tert-butyl ester (70% pure, 0.2 g, 0.347 mmol) was dissolved in a mixture of anhydrous dichloromethane (5 ml) and triethylamine (72 μl) and cooled in an ice-bath and stirred under nitrogen. Benzoyl chloride (40 μl, 1.0 eq) was added dropwise and the reaction was stirred for 5 minutes, then warmed to ambient temperature and stirred for an additional 16 hours. The solvent was removed in vacuo and the residue dissolved in ethyl acetate (20 ml) and washed with 0.5 N hydrochloric acid (5 ml), saturated sodium bicarbonate (5 ml), and brine (5 ml). The organic phase was dried (MgSO$_4$), filtered, and concentrated in vacuo, which afforded 0.15 g of crude 7-(benzoylamino-methyl)-2-amino-6-(4-methoxy-benzyl)-4,5,6,7-tetrahydro-thieno[2,3-c]pyridine-3-carboxylic acid tert-butyl ester.

$^1$H-NMR (300 MHz, CDCl$_3$): δ 7.60 (d, 2H, J=7 Hz, 2H), 7.51-7.38 (m, 3H), 7.20 (d, 2H, J=8 Hz), 6.75 (d, 2H, J=8 Hz), 6.64-6.61 (m,1H), 6.02 (s, 2H), 3.84-3.58 (m, 4H), 3.72 (s, 3H), 3.30-3.12 (m, 2H), 2.94-2.76 (m, 2H), 2.68-2.62 (m, 1H), 1.54 (s, 9H).

LC-MS: R$_t$=1.31 min, m/z: 508 [M+H]$^+$

To a solution of crude 7-(benzoylamino-methyl)-2-amino-6-(4-methoxy-benzyl)-4,5,6,7-tetrahydro-thieno[2,3-c]pyridine-3-carboxylic acid tert-butyl ester (0.15 g, 0.30 mmol) in anhydrous dichloromethane (5 ml) was added midazol-1-yl-oxo-acetic acid tert-butyl ester (0.17 g, 0.9 mmol). The reaction was stirred at ambient temperature for 16 hours, concentrated in vacuo and the crude residue purified by silica gel chromatography using a gradient of ethyl acetate/dichloromethane from, 5% to 10% as eluent, which afforded 0.16 g of 7-(benzoylamino-methyl)-2-(tert-butoxyoxalyl-amino)-6-(4-methoxy-benzyl)-4,5,6,7-tetrahydro-thieno[2,3-c]pyridine-3-carboxylic acid tert-butyl ester. The overall yield of the first two steps was 71%.

$^1$H-NMR (300 MHz, CDCl$_3$): δ 12.56 (s, 1H), 7.61 (d, 2H, J=7 Hz), 7.49-7.39 (m, 3H), 7.20 (d, 2H, J=8 Hz), 6.77 (d, 2H, J=8 Hz), 6.60-6.57 (m, 1H), 3.90-3.66 (m, 4H), 3.74 (s, 3H), 3.40-3.32 (m, 1H), 3.25-3.16 (m, 1H), 3.02-2.84 (m, 2H), 2.78-2.71 (m, 1H), 1.60 (s, 18H).

LC-MS: R$_t$=3.65 min, m/z: 636 [M+H]$^+$ 7-(Benzoylamino-methyl)-2-(tert-butoxyoxalyl- amino)-6-(4-methoxy-benzyl)-4,5,6,7-tetrahydro-thieno[2,3-c]pyridine-3-carboxylic acid tert-butyl ester (0.157 g, 0.247 mmol) was dissolved in a mixture of 10% formic acid/methanol (4 ml). 10% Palladium on activated carbon (75 mg) was added and the reaction stirred at ambient temperature for 24 hours. Another 50 mg of catalyst was added and the reaction stirred for an additional 72 hours. The solution was filtered through celite and the filter cake washed with hot methanol. The filtrate was concentrated in vacuo and the residue precipitated from hexanes. The precipitate was filtered off and washed with hexane, which afforded 75 mg (59%) of 7-(benzoylamino-methyl)-2-(tert-butoxyoxalyl-amino)-4,5,6,7-tetrahydro-thieno[2,3-c]pyridine-3-carboxylic acid tert-butyl ester as a solid.

$^1$H-NMR (400 MHz, CDCl$_3$): δ 12.54 (s, 1H), 8.20 (s, 1H), 7.82 (d, 2H, J=7 Hz), 7.77 (bs, 1H), 7.49-7.38 (m, 3H), 4.59-4.55 (m, 1H), 4.12-4.08 (m, 1H), 3.63-3.56 (m, 1H), 3.41-3.37 (m, 1H), 3.12-2.98 (m, 3H), 1.60 (s, 18H).

LC-MS: R$_t$=1.28 min., m/z: 516 [M+H]$^+$ 7-(Benzoylamino-methyl)-2-(tert-butoxyoxalyl-amino)-4,5,6,7-tetrahydro-thieno[2,3-c]pyridine-3-carboxylic acid tert-butyl ester (50 mg, 0.097 mmol) was dissolved in a mixture of 50% trifluoroacetic acid/dichloromethane (3 ml) and stirred at ambient temperature for 16 hours. The trifluoroacetic acid solution was added dropwise to diethyl ether, which precipitated the product. The suspension was stirred for 1 hour and the solid filtered off, which afforded 30 mg (60%) of the title compound as a solid.

$^1$H-NMR (400 MHz, DMSO): δ 12.40 (bs, 1H), 9.54-9.16 (bm, 1H), 8.97 (s, 1H), 7.91 (d, 2H, J=7 Hz), 7.59-7.49 (m, 3H), 4.74 (s, 1H), 3.72 (bs, 2H), 3.55-3.52 (m, 1H), 3.33-3.31 (m, 1H obscured by water), 3.04 (bs, 2H).

LC-MS: R$_t$=0.66 min., m/z: 404 [M+H]$^+$

Example 2

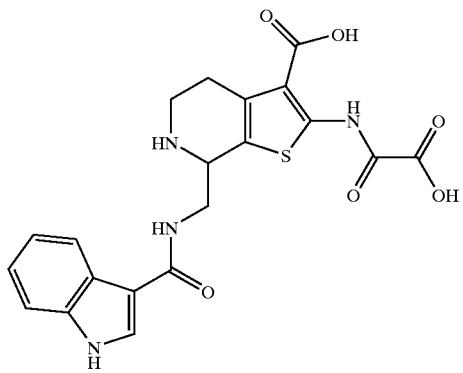

7-(((1H-Indole-3-carbonyl)-amino)-methyl)-2-(oxalyl-amino)-4,5,6,7-tetrahydro-thieno[2,3-c]pyridine-3-carboxylic acid The title compound was prepared in a similar way as in Example 1 using 3-indole-carboxylic acid and 2-amino-7-aminomethyl-6-(4-methoxy-benzyl)-4,5,6,7-tetrahydro-thieno[2,3-c]pyridine-3-carboxylic acid tert-butyl ester as the starting material.

LC-MS: m/z: 442.8 [M+H]$^+$

Example 3(OC 235–399)

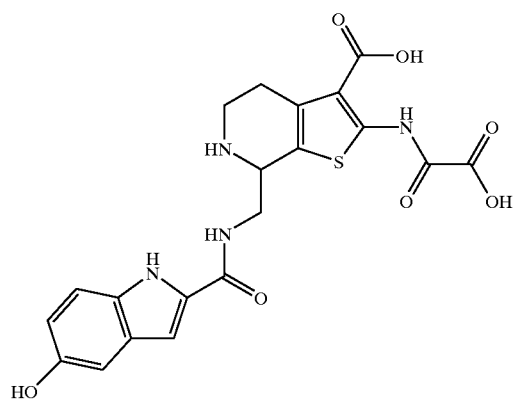

7-(((5-Hydroxy-1H-indole-2-carbonyl)amino)methyl)-2-(oxalyl-amino )4,5,6,7-tetrahydro-thieno[2,3-c]pridine-3-carboxylic acid The title compound was prepared in a similar way as in Example 1 using 5-hydroxy-1H-indole-2-carboxylic acid and 2-amino-7-aminomethyl-6-(4-methoxy-benzyl)-4,5,6,7-tetrahydro-thieno[2,3-c]pyridine-3-carboxylic acid tert-butyl ester as the starting material.

LC-MS: R$_t$=2.99 min; m/z: 459 [M+H]$^+$

Example 4

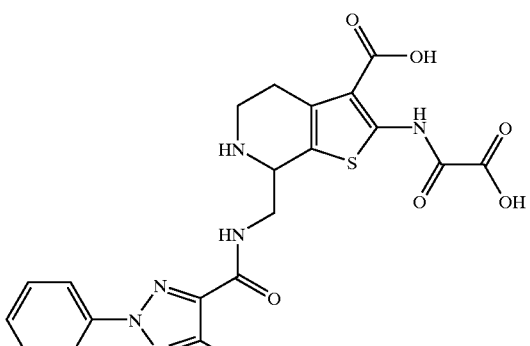

7-(((5-Methyl-2-phenyl-2H-[1,2,3]triazole-4-carbonyl)-amino)-methyl )2-(oxalyl-amino)-4,5,6,7-tetrahydro-thieno[2,3-c]pyridine-3-carboxylic acid The title compound was prepared in a similar way as in Example 1 using 5-methyl-2-phenyl-2H-[1,2,3]triazole-4-carboxylic acid and 2-amino-7-aminomethyl-6-(4-methoxy-benzyl)-4,5,6,7-tetrahydro-thieno[2,3-c]pyridine-3-carboxylic acid tert-butyl ester as the starting material.

LC-MS: m/z: 485.2 [M+H]$^+$

HPLC (B6) R$_t$=18.50 min;

Example 5

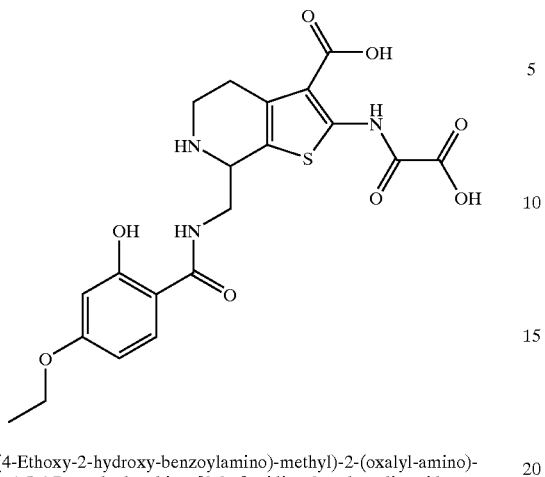

7-((4-Ethoxy-2-hydroxy-benzoylamino)-methyl)-2-(oxalyl-amino)-4,5,6,7-tetrahydro-thieno[2,3-c]pyidine-3-carboxylic acid The title compound was prepared in a similar way as in Example 1 using 4-ethoxy-2-hydroxy-benzoic acid and 2-amino-7-aminomethyl-6-(4-methoxy-benzyl)-4,5,6,7-tetrahydro-thieno[2,3-c]pyridine-3-carboxylic acid tert-butyl ester as the starting material.

LC-MS: m/z: 464 [M+H]$^+$

Calculated for $C_{20}H_{21}N_3O_8S$, $1 \times C_2HF_3O_2$, $1 \times H_2O$;

C, 44.37%; H, 4.06%; N, 7.06%. Found:

C, 44.53%; H, 4.05%; N, 6.66%.

Example 6

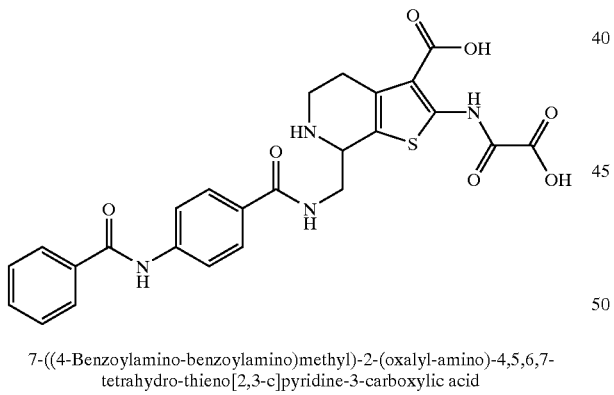

7-((4-Benzoylamino-benzoylamino)methyl)-2-(oxalyl-amino)-4,5,6,7-tetrahydro-thieno[2,3-c]pyridine-3-carboxylic acid The title compound was prepared in a similar way as in Example 1 using 4-benzoylaminobenzoic acid and 2-amino-7-aminomethyl-6-(4-methoxy-benzyl)-4,5,6,7-tetrahydro-thieno[2,3-c]pyridine-3-carboxylic acid tert-butyl ester as the starting material.

LC-MS: m/z: 523 [M+H]$^+$

Calculated for $C_{25}H_{22}N_4O_7S$, $2 \times C_2HF_3O_2$, $2 \times H_2O$;

C, 44.28%; H, 3.59%; N, 7.12%. Found:

C, 44.68%; H, 3.41%; N, 7.06%.

Example 7

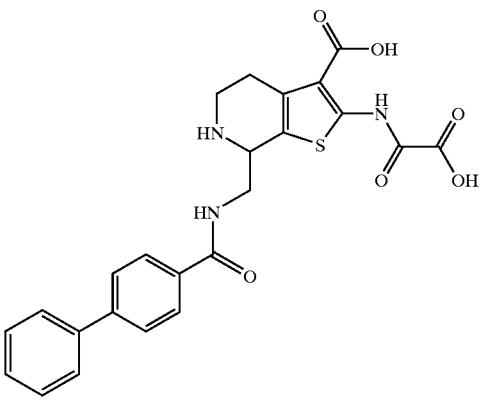

7-(((Biphenyl-4-carbonyl)amino)methyl)-2-(oxalyl-amino)-4,5,6,7-tetrahydro-thieno[2,3-c]pyridine-3-carboxylic acid The title compound was prepared in a similar way as in Example 1 using 4-phenylbenzoic acid and 2-amino-7-aminomethyl-6-(4-methoxy-benzyl)-4,5,6,7-tetrahydro-thieno[2,3-c]pyridine-3-carboxylic acid tert-butyl ester as the starting material.

LC-MS: m/z: 480 [M+H]$^+$

HPLC (B6) $R_t$=20.11 min.

Example 8

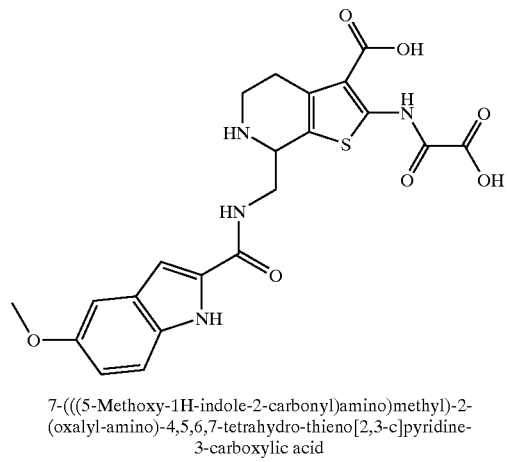

7-(((5-Methoxy-1H-indole-2-carbonyl)amino)methyl)-2-(oxalyl-amino)-4,5,6,7-tetrahydro-thieno[2,3-c]pyridine-3-carboxylic acid The title compound was prepared in a similar way as in Example 1 using 5-methoxyindole-2-carboxylic acid and 2-amino-7-aminomethyl-6-(4-methoxy-benzyl)4,5,6,7-tetrahydro-thieno[2,3-c]pyridine-3-carboxylic acid tert-butyl ester as the starting material.

LC-MS: m/z: 473 [M+H]$^+$

HPLC (B6) $R_t$=15.16 min.

Calculated for $C_{21}H_{20}N_4O_7S$, $1 \times C_2HF_3O_2$, $1 \times H_2O$;

C, 45.70%; H, 3.83%; N, 9.27%. Found:

C, 46.23%; H, 4.23%; N, 8.57%.

Example 9

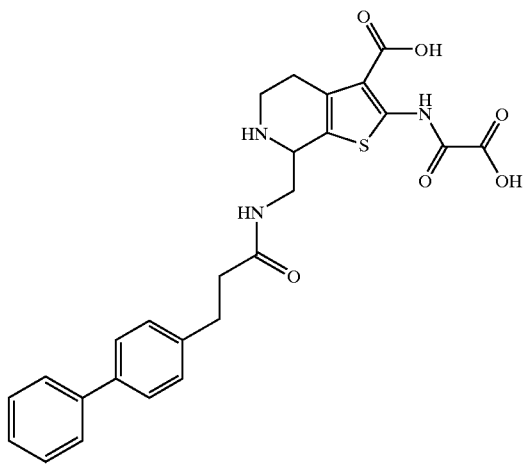

7-((3-Biphenyl-4-yl-propionylamino)methyl)-2-(oxalyl-amino)-4,5,6,7 tetrahydro-thieno[2,3-c]-pyridine-3-carboxylic acid The title compound was prepared in a similar way as in Example 1 using 3-biphenyl-4-yl-acrylic acid and 2-amino-7-aminomethyl-6-(4-methoxy-benzyl)-4,5,6,7-tetrahydro-thieno[2,3-c]pyridine-3-carboxylic acid tert-butyl ester as the starting material.

LC-MS: m/z: 508.2 [M+H]$^+$

HPLC (B6) $R_t$=20.85 min.

Calculated for $C_{26}H_{25}N_3O_6S$, $1 \times C_2HF_3O_2$, $1.5 \times H_2O$;

C, 51.85%; H, 4.51%; N, 6.48%. Found:

C, 52.06%; H, 4.38%; N, 6.24%.

Example 10

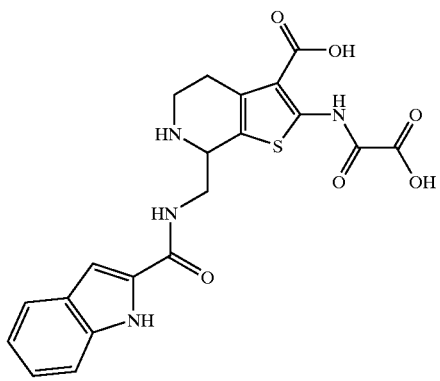

7-(((1H-Indole-2-carbonyl)amino)methyl)-2-(oxalyl-amino)-4,5,6,7-tetrahydro-thieno[2,3-c]pyridine-3-carboxylic acid The title compound was prepared in a similar way as in Example 1 using indole-2-carboxylic acid and 2-amino-7-aminomethyl-6-(4-methoxy-benzyl)-4,5,6,7-tetrahydro-thieno[2,3-c]pyridine-3-carboxylic acid tert-butyl ester as the starting material.

LC-MS: m/z: 443 [M+H]$^+$

HPLC (B6) $R_t$=15.37 min.

Calculated for $C_{20}H_{18}N_4O_6S$, $1.2 \times C_2HF_3O_2$, $0.8 \times H_2O$;

C, 45.32%; H, 3.53%; N, 9.44%. Found:

C, 45.56%; H, 3.86%; N, 9.15%.

Example 11

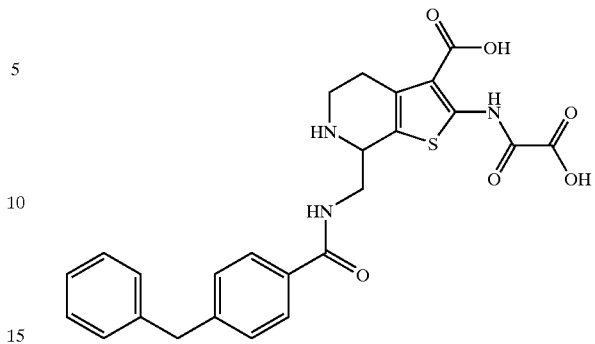

7-((4-Benzyl-benzoylamino)-methyl)-2-(oxalyl-amino)-4,5,6,7-tetrahydro-thieno[2,3-c]pyridine-3-carboxylic acid The title compound was prepared in a similar way as in Example 1 using 4-benzyl benzoic acid and 2-amino-7-aminomethyl-6-(4-methoxy-benzyl)-4,5,6,7-tetrahydro-thieno[2,3-c]pyridine-3-carboxylic acid tert-butyl ester as the starting material.

LC-MS: m/z: 494 [M+H]$^+$

Calculated for $C_{25}H_{23}N_3O_6S$, $2/3 \times C_2HF_3O_2$, $2 \times H_2O$;

C, 52.23%; H, 4.60%; N, 6.94%. Found:

C, 52.45%; H, 4.46%; N, 7.25%.

Example 12

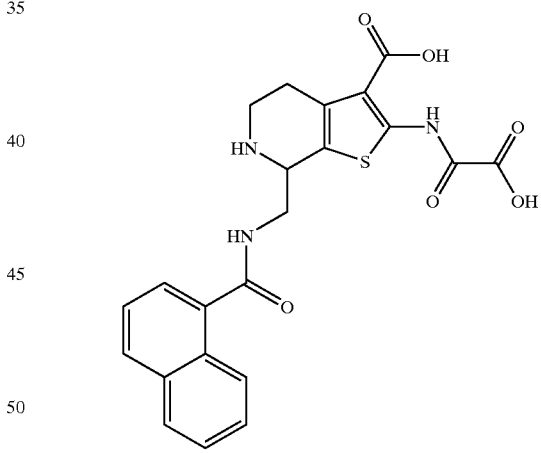

7-(((Naphthalene-1-carbonyl)amino)methyl)-2-(oxalyl-amino)-4,5,6,7-tetrahydro-thieno[2,3-c]pyridine-3-carboxylic acid The title compound was prepared in a similar way as in Example 1 using naphthalene-1-carboxylic acid and 2-amino-7-aminomethyl-6-(4-methoxy-benzyl)-4,5,6,7-tetrahydro-thieno[2,3-c]pyridine-3-carboxylic acid tert-butyl ester as the starting material.

LC-MS: m/z: 454 [M+H]$^+$

Calculated for $C_{22}H_{19}N_3O_6S$, $2/3 \times C_2H F_3O_2$, $1 \times H_2O$;

C, 47.40%; H, 3.42%; N, 6.63%. Found:

C, 47.47%; H, 3.66%; N, 6.46%.

Example 13

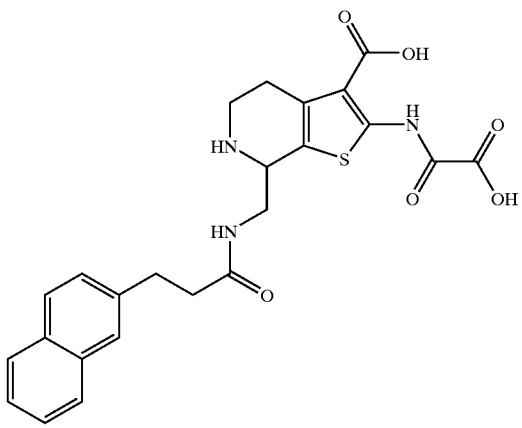

7-((3-Naphthalen-2-yl-propionylamino)-methyl)-2-(oxalyl-amino)-4,5,6,7-tetrahydro-thieno[2,3-c]pyridine-3-caboxylic acid The title compound was prepared in a similar way as in Example 1 using 3-(2-naphthyl)-acrylic acid and 2-amino-7-aminomethyl-6-(4-methoxy-benzyl)-4,5,6,7-tetrahydro-thieno[2,3-c]pyridine-3-carboxylic acid tert-butyl ester as the starting material.

LC-MS: m/z: 482.2 [M+H]$^+$

Calculated for $C_{24}H_{23}N_3O_6S$, $2 \times C_2HF_3O_2$;
C, 47.40%; H, 3.55%; N, 5.92%. Found:
C, 47.36%; H, 3.67%; N, 5.86%.

Example 14

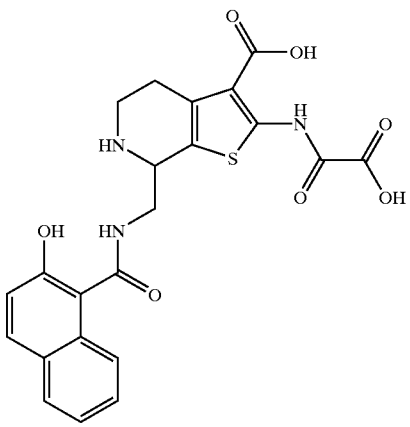

7-(((2-Hydroxy-naphthalene-1-carbonyl)amino)methyl)-2-(oxalyl-amino)-4,5,6,7-tetrahydro-thieno[2,3-c]pyridine-3-caboxylic acid The title compound was prepared in a similar way as in Example 1 using 2-hydroxynaphthalene-1-carboxylic acid and 2-amino-7-aminomethyl-6-(4-methoxy-benzyl)-4,5,6,7-tetrahydro-thieno[2,3-c]pyridine-3-carboxylic acid tert-butyl ester as the starting material.

LC-MS: m/z: 469.8 [M+H]$^+$

Calculated for $C_{22}H_{19}N_3O_7S$, $1 \times C_2HF_3O_2$, $2/3 \times H_2O$;
C, 48.41%; H, 3.61%; N, 7.06%. Found:
C, 48.67%; H, 4.01%; N, 6.80%.

Example 15

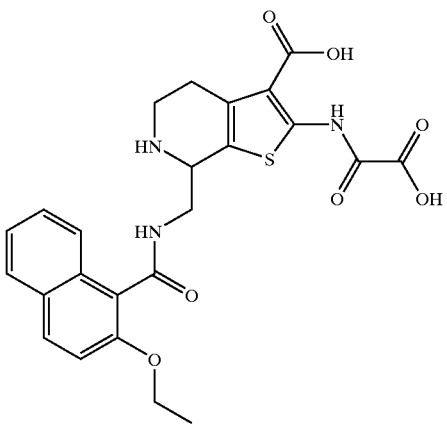

7-(((2-Ethoxy-naphthalene-1-carbonyl)amino)methyl)-2-(oxalyl-amin o)-4,5,6,7-tetrahydro-thieno[2,3-c]pyridine-3-caboxylic acid The title compound was prepared in a similar way as in Example 1 using 2-ethoxy-naphthalene-1-carboxylic acid and 2-amino-7-aminomethyl-6-(4-methoxy-benzyl)-4,5,6,7-tetrahydro-thieno[2,3-c]pyridine-3-carboxylic acid tert-butyl ester as the starting material.

Calculated for $C_{24}H_{23}N_3O_7S$, $C_2HF_3O_2$, $1.5 \times H_2O$
C, 48.90%; H, 4.26%; N, 6.58% Found:
C, 48.77%; H, 4.27%; N, 6.28%

General Chiral Synthesis

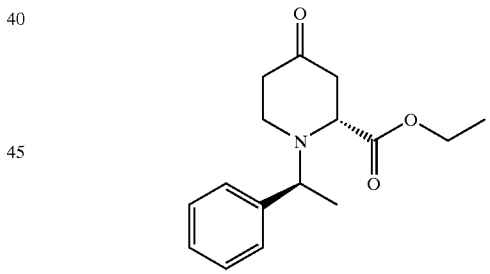

4-Oxo-1-((S)-1phenyl-ethyl)-piperidine-(R)-2-carboxylic acid ethyl ester

Dichloromethane (1 l) and mol sieves 3 Å (113 g) and amine (S)-(−)α-methylbenzylamin (71,7 ml) were mixed in a 2 l three-necked bottle cooled to −5° C. (using a ethanol/water/ice bath). A 50% solution of ethylglyoxylate in toluene (117,6 ml) was added drop wise over 20 min., keeping the temperature between −5° C. and 0° C. The mixture was stirred for 0.5 hour before it was cooled to −30° C. Trifluoroacetic acid (45,2 ml) was added over 3–4 minutes. Boron trifluoride diethyl ether (69,8 ml) was added drop wise over 5 minutes at −55° C. The ice bath was removed and the mixture was allowed to warm up to −45° C. whereupon 2-(trimethylsilyloxy)-1,3-butadiene (100 ml) was added drop wise over 10 minutes. During the addition the mixture was cooled and the temperature kept below −20° C. The above additions are all exothermic hence the cooling bath should have sufficient capacity to remove the heat generated during the rapid addition. The reaction mixture was stirred for 2 hours at −15° C. and 1 hour at 0° C. and then poured on ice/water and stirred for 15 minutes. Solid sodium hydrogen carbonate was added until pH 7–8. The mixture was stirred overnight at room temperature. The layers wee separated and the aqueous phase extracted with dichloromethane. The combined organic phases were filtered through a plug of silica eluting with dichloromethane. The relevant fractions were concentrated in vacuo. The residue was dissolved in hot heptane and cooled. This leaves a yellowish gummy material on the side of the flask and crystals starts forming. The heptane solution was heated again to dissolve crystals, leaving the gummy material on the side of the flask and the mixture was filtered hot. The heptane solution was cooled to room temperature and the precipitate was filtered off and dried in vacuo which afforded 38 g of 4-oxo-1-((S)-1-phenyl-ethyl)piperidine-(R)-2-carboxylic acid ethyl ester as a solid.

The filtrate was put in a refrigerator and a second crop was formed which was less pure and needed recrystallization from heptane to yield another 7,5 g of 4-oxo-1-((S)-1-phenyl-ethyl)-piperidine-(R)-2-carboxylic acid ethyl ester.

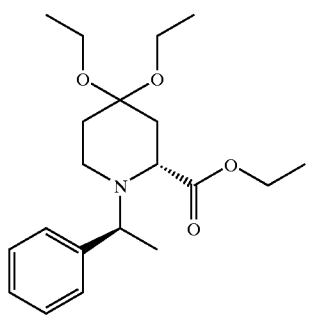

4,4-Diethoxy-1-((S)-1phenyl-ethyl)-piperidine-(R)-2-carboxylic acid ethyl ester

4-Oxo-1-((S)-1-phenyl-ethyl)-piperidine-(R)-2-carboxylic acid ethyl ester (11.0 g, 0.040 mmol) was dissolved in a 1:1 mixture of triethyl orthoformate and ethanol (140 ml) and para-toluene-4-sulphonic acid (15.2 g, 80 mmol) was added and the reaction mixture was stirred for 16 hours. The reaction mixture was neutralized with sodium bicarbonate (to pH 7–8), and extracted with dichloromethane (3×100 ml), dried (MgSO$_4$), filtered and concentrated in vacuo. The residue was purified by column chromatography (SiO$_2$, petrol ether/ethyl acetate 10:1), which afforded 12.0 g (86%) of the title compound as an oil.

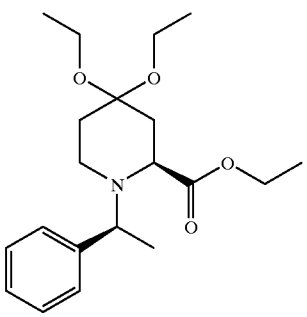

4,4-Diethoxy-1-((S)-1phenyl-ethyl)-piperidine-(S)-2-carboxylic acid ethyl ester

The mother liquor from the above crystallization was concentrated in vacuo. 5.0 g of the resulting material (18.16 mmol) was dissolved in ethanol (100 ml) and triethylorthoformate (26.9 g, 181.6 mmol) and para-toluen-4-sulphonic acid (6.9 g, 36.32 mmol) was added. The reaction was stirred at room temperature for 16 hours before the mixture was poured on aqueous sodium hydrogen carbonate (200 ml) and extracted with ethyl acetate (4×75 ml). The combined extracts were concentrated in vacuo and purified by column chromatography (SiO$_2$, Flash 40, petrol ether-ethyl acetate 10:1). Collection of the first band (R$_f$=0.68) gave 1.14 g (18%) of 4,4-diethoxy-1-((S)-1-phenyl-ethyl)-piperidine-(R)-2-carboxylic acid ethyl ester and collection of the second band (Rf=0.4) gave 3.60 g (57%) of the title compound.

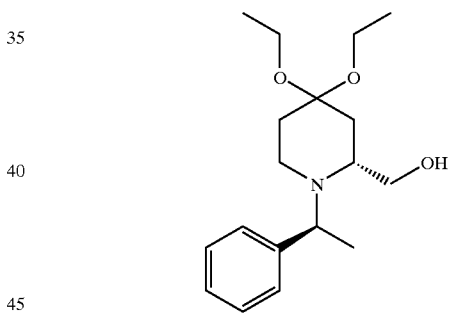

4,4-Diethoxy-1-((S)-1-phenyl-ethyl)-(R)-2-hydroxymethyl-piperidine

To a solution of 4,4-diethoxy-1-((S)-1-phenyl-ethyl)-piperidine-(R)-2-carboxylic acid ethyl ester (36.0 g, 0.103 mol) in dry diethyl ether (150 ml) was added a suspension of lithium aluminum hydride (5.88 g, 0.155 mol) in dry diethyl ether (300 ml) under an atmosphere of nitrogen at such a rate that the solution gently reflux. The reaction mixture was stirred over night before it was cooled to 0° C. and ethyl acetate (30 ml) was added drop wise to destroy excess lithium aluminum hydride. After stirring for another 0.5 hour, water (12 ml) was added drop wise. After stirring for 10–15 min the precipitate was filtered off through celite and the filter cage was washed with plenty of diethyl ether. The filtrate was washed with brine (100 ml), dried (MgSO$_4$), filtered and the solvent evaporated in vacuo, which afforded 30 g (95%) of the title compound as an oil.

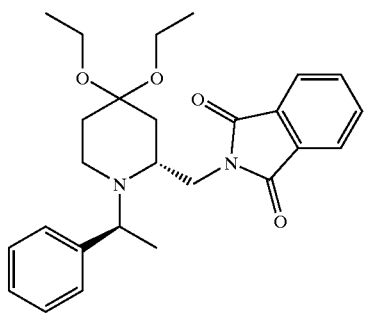

4,4-Diethoxy-1-((S)-1-phenyl-ethyl)-(R)-2-phthalimidomethyl-piperidine

A solution of 4,4-diethoxy-1-((S)1-phenyl-ethyl)-(R)-2-hydroxymethyl-piperidine (65.35 g, 0.213 mmol), triphenylphosphine (61.3 g, 0.234 mol) and phthalimide (34.4 g, 0.234 mol) in tetrahydrofuran (700 ml) cooled to 0° C. was added diethyl azodicarboxylate over the course of 1.5 hour. The reaction mixture was stirred at 0° C. for another 2 hours before the solvent was removed in vacuo. The residue was dissolved in hot heptane-toluene (3:2) (650 ml) before it was cooled on an ice bath. The precipitate consisting of triphenyl phosphine oxide was filtered off and washed with heptane. The filtrate was concentrated in vacuo and the residue subjected to column chromatography using a mixture of toluene-ethyl acetate-heptane (3:1:3) as eluent. The solvent was evaporated In vacuo whereupon a viscous oil was obtained. Upon addition of light petrol ether the product crystallized to give 67.4 g (73%) of the title compound as a solid.

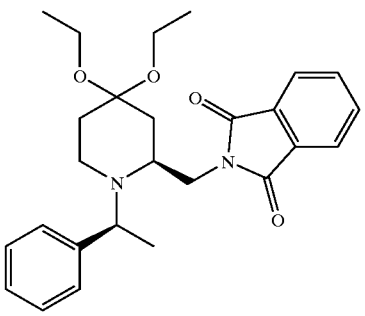

4,4-Diethoxy-1-((S)-1-phenyl-ethyl)-(S)-2-phthalimidomethyl-piperidine

A suspension of 4,4-diethoxy-1-((S)1-phenyl-ethyl)-(S)-2-hydroxymethyl-piperidine (20 g, 65 mmol), triphenylphosphine (18.76 g, 72 mmol) and phthalimide (10.52 g, 0.072 mol) in tetrahydrofuran (200 ml) cooled to 0° C. was added diethyl azodicarboxylate over the course of 1 hour. The reaction mixture was stirred at 0° C. for another 2 hours before the solvent was removed in vacuo. The residue was dissolve in a hot mixture of heptane/toluene (3:2) (100 ml) before it was cooled on an ice bath. The precipitate was filtered off and washed with heptane. The filtrate was concentrated in vacuo and subjected to column chromatography using a mixture of toluene/ethyl acetate/heptane (3:1:3) as eluent. The solvent was evaporated in vacuo whereupon a viscous oil was obtained. Upon addition of light petrol ether (250 ml) the product crystallized to give 24 g (85%) of the title compound as a solid.

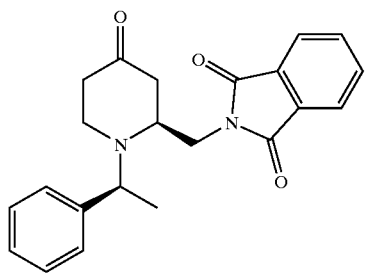

4,4-Oxo-1-((S)-1-phenyl-ethyl)-2-(S)-phthalimidomethyl-piperidine 4,4-Diethoxy-1-(1-(S)-phenyl-ethyl)-2-(S)-phthalimidomethyl-piperidine (4.0 g, 9.2 mmol) was dissolved in a mixture of trifluoroacetic acid/water (9:1) (100 ml) at 0° C. and stirred for 2 hours at this temperature. The mixture was basified with half saturated aqueous sodium carbonate, extracted with ethyl acetate and dried (MgSO$_4$) for 2 hours and filtered. The solvent was removed in vacuo and the residue was left in a vacuum own at 40° C. for two days, which afforded 3.23 g (98%) of 4-oxo-1-((S)-1-phenyl-ethyl)-2-(S)-phthalimidomethyl-piperidine as a solid.

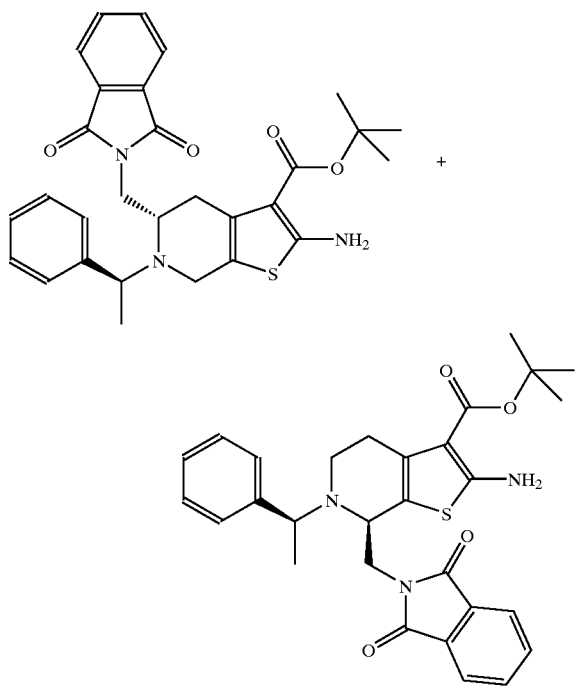

2-Amino-5-(S)-(1,3-dioxo-1,3-dihydro-isoindol-2-ylmethyl)-6-(1-(S)-phenyl-ethyl)-4,5,6,7-tetrahydrothieno[2,3-c]pyridine-3-carboxylic acid tert-butyl ester
and
2-Amino-7-(R)-(1,3-dioxo-1,3-dihydro-isoindol-2-ylmethyl)-6-(1-(S)-phenyl-ethyl)-4,5,6,7-tetrahydrothieno[2,3-c]pyridine-3-carboxylic acid tert-butyl ester A mixture of 4-oxo-1-(1-(R)-phenyl-ethyl)-2-phthalimidomethyl-piperidine (17.28 g, 47.73 mmol), tert-butylcyanoacetat (7.41 g, 52.17 mmol), sulphur (1.71 g, 52.17 mmol) and morpholine (8.31 g, 95.46 mmol) in ethanol (150 ml) was heated under an atmosphere of nitrogen at 50° C. The volatiles were removed in vacuo and the residue was subjected to column chromatography on silica gel using a mixture of heptane/ethyl acetate (5:1) as eluent. The band consisting of a mixture of 5- and 7-isomer was collected and purified on a reverse phase ($C_{18}$) column using a Flash 40 system. The residue was applied in a minimum volume of acetonitrile with 40% acetonitrile in water containing 0.1% trifluoroacetic acid. When the first isomer (the 5-isomer) was collected the eluent was changed to 50% acetonitrile in water with 0.1% trifluoroacetic acid and the 7-isomer was collected. Yield of: 2-amino-5-(S)-(1,3-dioxo-1,3-dihydro-isoindol-2-ylmethyl)-6-(1-(S)-phenyl-ethyl)-4,5,6,7-tetrahydrothieno[2,3-c]pyridine-3-carboxylic acid tert-butyl ester was 7.96 g.

Yield of: 2-Amino-7-(R)-(1,3-dioxo-1,3-dihydro-isoindol-2-ylmethyl)-6-(1-(S)-phenyl-ethyl)-4,5,6,7-tetrahydrothieno[2,3-c]pyridine-3-carboxylic acid tert-butyl ester was 3.72 g (47% total of 5- and 7-isomer).

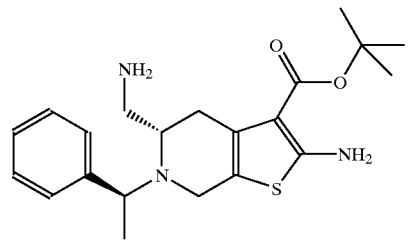

2-Amino-5-(S)-aminomethyl-6-(1-(S)-phenyl-ethyl)-4,5,6,7-tetrahydrothieno[2,3-c]pyridine-3-carboxylic acid tert-butyl ester 2-Amino-5-(S)-(1,3-dioxo-1,3-dihydro-isoindol-2-ylmethyl)-6-(1 -(S)-phenyl-ethyl)-4,5,6,7-tetrahydrothieno[2,3-c]pyridine-3-carboxylic acid tert-butyl ester (7.96 g, 15.4 mmol) and hydrazine hydrate (3.85 g, 77.0 mmol) in ethanol (250 ml) was stirred for 16 hours at room temperature. The solvent was removed in vacuo and the white material obtained was extracted with diethyl ether (3×200 ml), the fractions were combined and the solvent was removed in vacuo to give 5.9 g (100%) of the title compound as a solid.

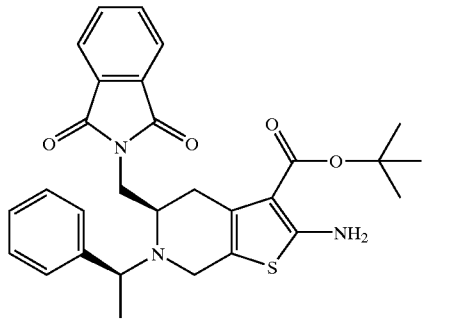

+

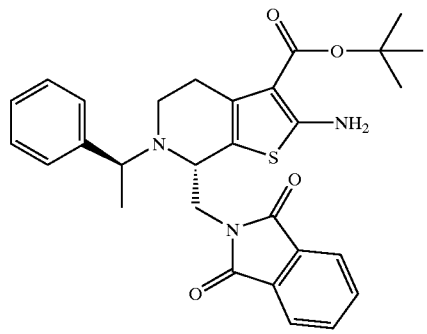

2-Amino-5-(R)-(1,3-dioxo-1,3-dihydro-isoindol-2-ylmethyl)-6-(1-(S)-phenyl-ethyl)-4,5,6,7-tetrahydrothieno[2,3-c]pyridine-3-carboxylic acid tert-butyl ester
and
2-Amino-7-(S)-(1,3-dioxo-1,3-dihydro-isoindol-2-ylmethyl)-6-(1-(S)-phenyl-ethyl)-4,5,6,7-tetrahydrothieno[2,3-c]pyridine-3-carboxylic acid tert-butyl ester A mixture of 4-oxo-1-(1-(S)-phenyl-ethyl)-2-phthalimidomethyl-piperidine (55.3 g, 0.152 mol), tert-butylcyanoacetat (23.7 g, 0.168 mol), sulphur (5.4 g, 0.168 mol) and morpholine (26.6 g, 0.305 mol) in ethanol (150 ml) was heated under an atmosphere of nitrogen at 50° C. The volatiles were removed in vacuo and the residue was subjected to column chromatography on silica gel using a mixture of heptane/ethyl acetate (5:1) as eluent. The band consisting of a mixture of 5- and 7-isomers was collected affording 63 g (80%).

The batch was divided in two portions and purified on a reverse phase ($C_{18}$) column using a Flash 75 system. The residue was applied in a minimum volume of acetonitrile and eluted with 35% acetonitrile in water containing 0.1% trifluoroacetic acid. When the first band consisting of the 5-isomer was collected the eluent was changed to 40% acetonitrile in water with 0.1% trifluoroacetic acid and the second band containing the 7-isomer was collected.

Yield of: 2-Amino-5-(R)-(1,3-dioxo-1,3-dihydro-isoindol-2-ylmethyl)-6-(1-(S)-phenyl-ethyl)-4,5,6,7-tetrahydrothieno[2,3-c]pyridine-3-carboxylic acid tert-butyl ester was 44.56 g (57%).

Yield of: 2-Amino-7-(S)-(1,3-dioxo-1,3-dihydro-isoindol-2-ylmethyl)-6-(1-(S)-phenyl-ethyl)-4,5,6,7-tetrahydrothieno[2,3-c]pyridine-3-carboxylic acid tert-butyl ester was 12.9 g (16%).

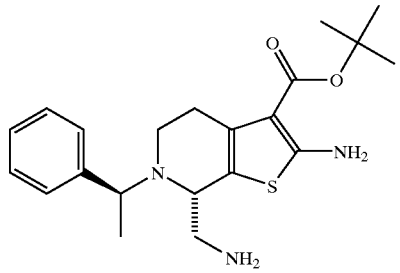

2-Amino-7-(S)-aminomethyl-6-(1-(S)-phenyl-ethyl)-4,5,6,7-tetrahydrothieno[2,3-c]pyridine-3-carboxylic acid tert-butyl ester 2-Amino-7-(S)-(1,3-dioxo-1,3-dihydro-isoindol-2-ylmethyl)-6-(1-(S)-phenyl-ethyl)-4,5,6,7-tetrahydrothieno[2,3-c]pyridine-3-carboxylic acid tert-butyl ester (10.9 g, 21.0 mmol) and hydrazine hydrate (5.2 g, 105 mmol) in ethanol (400 ml) was stirred for 16 hours at room temperature. The solvent was removed in vacuo and the solid residue obtained was extracted with diethyl ether (2×250 ml), the fractions were combined and the solvent removed in vacuo to give 7.64 g (94%) of the title compound.

Method A

General Procedure for Amide Formation

To a solution of a relevant carboxylic acid (0.71 mmol) in N,N-dimethylformamide (5.0 ml) was added 1-(3-dimethylaminopropyl)-3-ethylcarbodiimide hydrochloride (136 mg, 0.71 mmol) and [1,2,3]triazolo[4,5-b]pyridin-3-ol (96 mg, 0.71 mmol) and the mixture was stirred for 5 minutes at room temperature before a solution of diisopropylethylamine (121 µl, 0.71 mmol) and 2-amino-7-(S)-aminomethyl-6-(1-(S)-phenyl-ethyl)-4,5,6,7-tetrahydrothieno[2,3-c]pyridine-3-carboxylic acid tert-butyl ester (250 mg, 0.645 mmol) in N,N-dimethylformamide (5 ml) was added. The reaction was stirred 2 hours at room temperature before the solvent was removed in vacuo and the residue partitioned between ethyl acetate and water. The aqueous phase was extracted with ethyl acetate and the combined organic phases were dried (MgSO$_4$), filtered and the solvent evaporated in vacuo. The residue was purified by column chromatography using a mixture of ethyl acetate and petroleum ether as eluent, which afforded pure amide derivatives.

Method B

General Procedure for Formation of Oxalamic Acid Tert-butyl Ester

To a solution of the fused 2-amino-thiophene in dichloromethane was added imidazol-1-yl-oxo-acetic acid tert-butyl ester (3 eq.) and triethylamine (3 eq.) and the reaction mixture was stirred 16 hours before it was transferred to a separation funnel and washed with aqueous sodium hydrogencarbonate. After drying (MgSO$_4$) the solvent was removed in vacuo and the crude product was purified by column chromatography using a mixture of ethyl acetate and petroleum ether as eluent.

Method C

General Procedure for Hydrogenolysis of the N-α-methyl Benzyl Protection Group

Method Ca

The α-methyl benzyl protected amine was dissolved in a mixture of methanol/formic acid (9:1) (app. 10 ml/100 mg α-methyl benzyl protected amine). The solution was degassed by purging with nitrogen for 1 minute before 10% Pd/C (50% H$_2$O content) was added. The reaction mixture was stirred at room temperature until TLC showed that all the starting material was consumed (typical 1–4 days). The Pd/C was filtered off using Celite and the filter cage was washed with plenty of methanol. The filtrate was concentrated in vacuo and the residue partitioned between ethyl acetate and water. The organic phase was separated, dried (MgSO$_4$) and filtered. The solvent was removed in vacuo and the crude product was purified using column chromatography (SiO$_2$, and a mixture of ethyl acetate/methanol as eluent).

Method Cb

The α-methyl benzyl protected amine was dissolved in a mixture of isopropyl alcohol/formic acid (9:1) (app. 10 ml/100 mg α-methyl benzyl protected amine). The solution was degassed by purging with nitrogen for 1 minute before 10% Pd/C (dry) was added. The reaction mixture was stirred at room temperature until TLC showed that all the starting material was consumed (typical 1–4 days). The Pd/C was filtered off using Celite and the filter cage was washed with plenty of methanol. The filtrate was concentrated in vacuo and partitioned between ethyl acetate and water. The organic phase was separated, dried (MgSO$_4$) and filtered. The solvent was removed in vacuo and the crude product was purified using column chromatography (SiO$_2$, and a mixture of ethyl acetate/methanol as eluent)

Method D

General Procedure for Deprotection of Carboxylic Acid Tert-butyl Esters

The carboxylic acid tert-butyl ester was dissolved in a mixture of trifluoroacetic acid/dichloromethane (1:1) (app. 1 ml/100 mg carboxylic acid tert-butyl ester). The reaction mixture was stirred for 16 hours at room temperature before diethyl ether (2×the reaction volume) was added dropwise. The precipitate was filtered off/spun down on a centrifuge and washed with diethyl ether to give analytical pure title compound.

Example 16

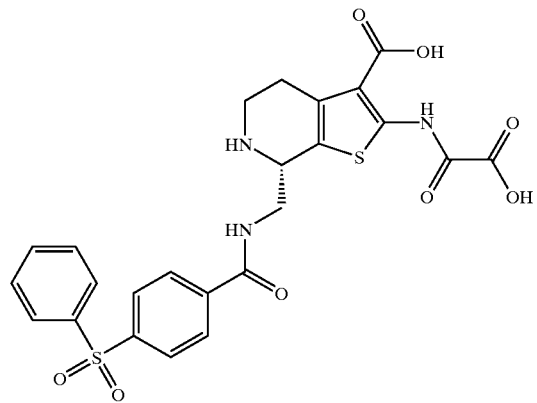

7-(S)-((4-Benzenesulfonyl-benzoylamino)-methyl)-2-(oxalyl-amino)-4,5,6,7-tetrahydro-thieno[2,3-c]pyridine-3-carboxylic acid The title compound was prepared using 4-benzenesulfonyl-benzoic acid and 2-amino-7-(S)-aminomethyl-6-(1-(S)-phenyl-ethyl)-4,5,6,7-tetrahydro-thieno[2,3-c]pyridine-3-carboxylic acid tert-butyl ester as the starting material and Method A, B, C and D as described above.

LC-MS; R$_t$=2.07 min, m/z: 544 [M+H]$^+$

Calculated for $C_{24}H_{21}N_3O_8S_2 \cdot 2/3 \times C_2HF_3O_2 \cdot 2/3 \times H_2O$;

C, 48.18; H, 3.67; N, 6.65; Found:

C, 48.02; H, 3.97; N, 6.54

Example 17

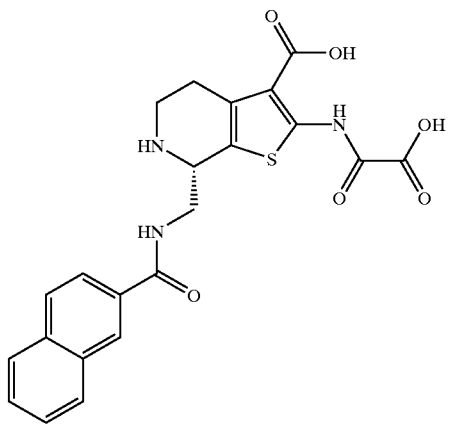

7-(S)-(((Naphthalene-2-carbonyl)amino)methyl)-2-(oxalyl-amino)
4,5,6,7-tetrahydro-thieno[2,3-c]pyridine-3-carboxylic acid The title compound was prepared using naphthalene-2-carboxylic acid and 2-amino-7-(S)-aminomethyl-6-(1-(S)-phenyl-ethyl)-4,5,6,7-tetrahydro-thieno[2,3-c]pyridine-3-carboxylic acid tert-butyl ester as the starting material and Method A, B, C and D as described above.

LC-MS; $R_t$=2.08 min, m/z: 454 [M+H]$^+$

Calculated for $C_{22}H_{19}N_3O_6S$, $1 \times C_2HF_3O_2$, $2 \times H_2O$;

C, 47.76; H, 4.01; N, 6.96; Found:

C, 47.96; H, 3.70; N, 6.75

Example 18

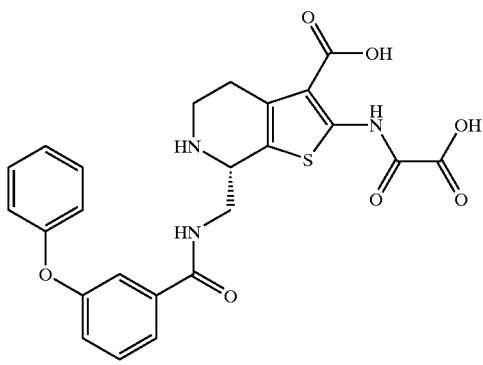

2-(Oxalyl-amino)-7-(S)-((3-phenoxy-benzoylamino)methyl)-4,5,6,7-
tetrahydro-thieno[2,3-c]pyridine-3-carboxylic acid The title compound was prepared using 3-phenoxy-benzoic acid and 2-amino-7-(S)-aminomethyl-6-(1-(S)-phenyl-ethyl)-4,5,6,7-tetrahydro-thieno[2,3-c]pyridine-3-carboxylic acid tert-butyl ester as the starting material and Method A, B, C and D as described above.

LC-MS; $R_t$=2.46 min, m/z: 496 [M+H]$^+$

Calculated for $C_{24}H_{21}N_3O_7S$. $1 \times C_2HF_3O_2$, $2 \times H_2O$;

C, 48.37; H, 4.06; N, 6.51; Found:

C, 48.58; H, 3.75; N, 6.54

Example 19

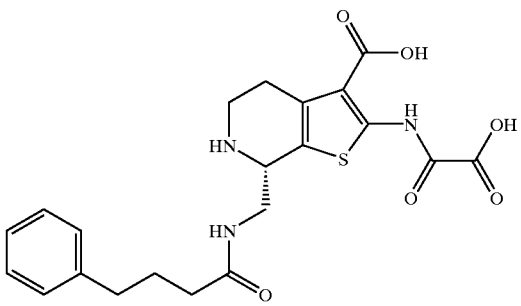

2-(Oxalyl-amino)-7-(S)-((4-phenyl-butyrylamino)methyl)-
4,5,6,7-tetrahydro-thieno[2,3-c]pyridine-3-carboxylic acid The title compound was prepared using 4-phenyl-butyric acid and 2-amino-7-(S)-aminomethyl-6-(1-(S)-phenyl-ethyl)-4,5,6,7-tetrahydro-thieno[2,3-c]pyridine-3-carboxylic acid tert-butyl ester as the starting material and Method A, B, C and D as described above.

LC-MS; RT=1.84 min, m/z: 446 [M+H]$^+$

Calculated for $C_{21}H_{23}N_3O_6S$, $1 \times C_2HF_3O_2$, $0.5 \times H_2O$;

C, 48.59; H, 4.43; N, 7.39; Found:

C, 48.50; H, 4.51; N, 7.50

Example 20

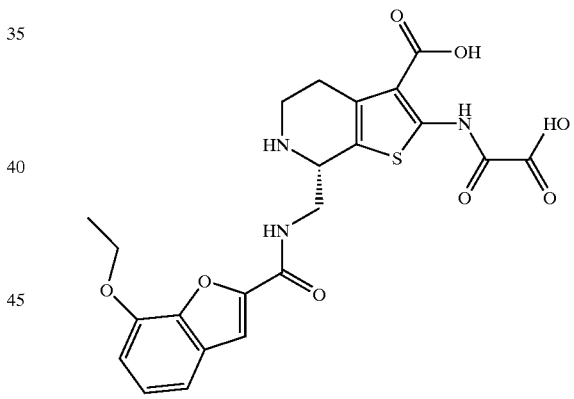

7-(S)-(((7-Ethoxy-benzofuran-2-carbonyl)-amino)-methyl)-2-
(oxalyl-amino)-4,5,6,7-tetrahydro-thieno[2,3-c]pyridine-
3-carboxylic acid The title compound was prepared using 7-ethoxy-benzofuran-2-carboxylic acid and 2-amino-7-(S)-aminomethyl-6-(1-(S)-phenyl-ethyl)-4,5,6,7-tetrahydro-thieno[2,3-c]pyridine-3-carboxylic acid tert-butyl ester as the starting material and Method A, B, C and D as described above.

LC-MS; $R_t$=2.14 min, m/z: 488 [M+H]$^+$

Calculated for $C_{22}H_{21}N_3O_8S$, $1 \times C_2HF_3O_2$, $1 \times H_2O$;

C, 46.53; H, 3.90; N, 6.78; Found:

C, 46.42; H, 3.99; N, 6.89

Example 21

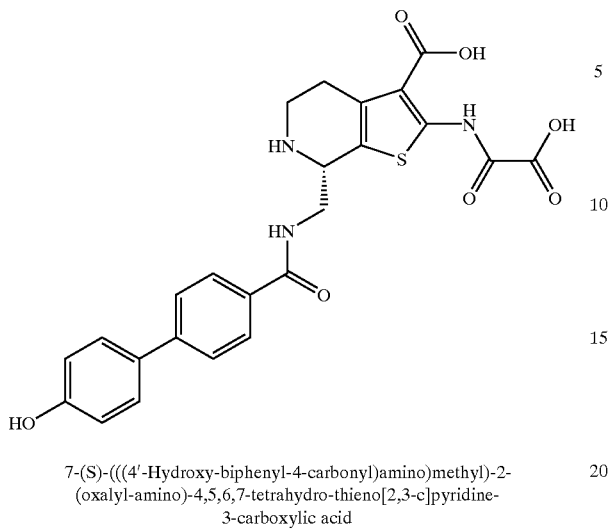

7-(S)-(((4'-Hydroxy-biphenyl-4-carbonyl)amino)methyl)-2-
(oxalyl-amino)-4,5,6,7-tetrahydro-thieno[2,3-c]pyridine-
3-carboxylic acid The title compound was prepared using 4'-hydroxy-biphenyl-4-carboxylic acid and 2-amino-7-(S)-aminomethyl-6-(1-(S)-phenyl-ethyl)-4,5,6,7-tetrahydro-thieno[2,3-c]pyridine-3-carboxylic acid tert-butyl ester as the starting material and Method A, B, C and D as described above.

LC-MS; $R_t$=1.91 min, m/z: 496 [M+H]$^+$
Calculated for $C_{24}H_{21}N_3O_7S$, 1.5×$C_2HF_3O_2$, 1.5×$H_2O$;
C, 46.76; H, 3.71; N, 6.06; Found:
C, 46.76; H, 3.72; N, 6.03

Example 22

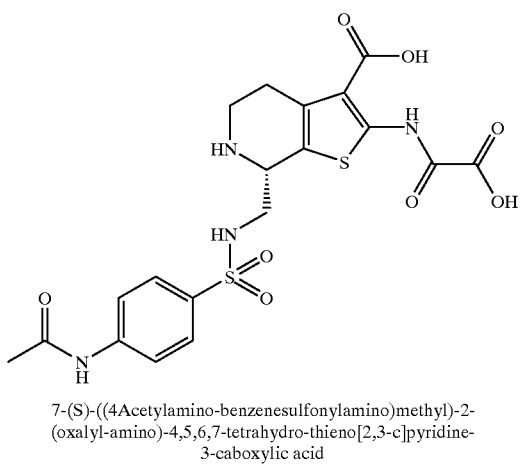

7-(S)-((4Acetylamino-benzenesulfonylamino)methyl)-2-
(oxalyl-amino)-4,5,6,7-tetrahydro-thieno[2,3-c]pyridine-
3-caboxylic acid The title compound was prepared using 4-acetylamino-benzenesulfonyl chloride and 2-amino-7-(S)-aminomethyl-6-(1-(S)-phenyl-ethyl)-4,5,6,7-tetrahydro-thieno[2,3-c]pyridine-3-carboxylic acid tert-butyl ester as the starting material. Formation of the sulpfonamide was performed in pyridine at room temperature using a slight excess of the sulfonyl chloride followed by Method B, C and D as described above.

LC-MS; $R_t$=0.97 min, m/z: 497 [M+H]$^+$

Example 23

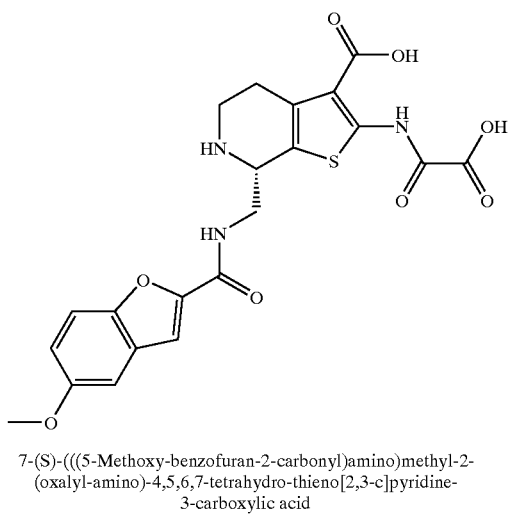

7-(S)-(((5-Methoxy-benzofuran-2-carbonyl)amino)methyl-2-
(oxalyl-amino)-4,5,6,7-tetrahydro-thieno[2,3-c]pyridine-
3-carboxylic acid The title compound was prepared using 5-methoxy-benzofuran-2-carboxylic acid and 2-amino-7-(S)-aminomethyl-6-(1-(S)-phenyl-ethyl)-4,5,6,7-tetrahydro-thieno[2,3-c]pyridine-3-carboxylic acid tert-butyl ester as the starting material and Method A, B, C and D as described above.

LC-MS; $R_t$=1.78 min, m/z: 473 [M+H]$^+$
Calculated for $C_{21}H_{19}N_3O_8S$, 1×$C_2HF_3O_2$, 0.5×$H_2O$;
C, 46.31; H, 3.55; N, 7.04; Found:
C, 46.41; H, 3.83; N, 7.01

Example 24

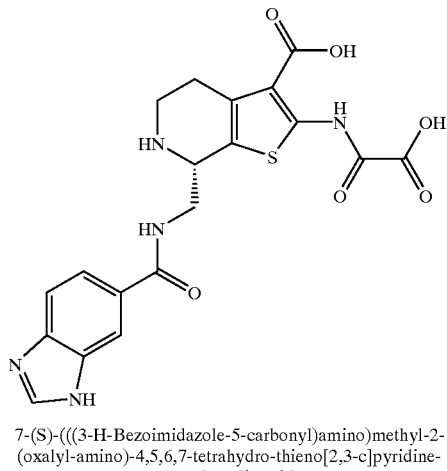

7-(S)-(((3-H-Bezoimidazole-5-carbonyl)amino)methyl)-2-
(oxalyl-amino)-4,5,6,7-tetrahydro-thieno[2,3-c]pyridine-
3-carboxylic acid The title compound was prepared using 3H-benzoimidazole-5-carboxylic acid and 2-amino-7-(S)-aminomethyl-6-(1-(S)-phenyl-ethyl)-4,5,6,7-tetrahydro-thieno[2,3-c]pyridine-3-carboxylic acid tert-butyl ester as the starting material and Method A, B, C and D as described above.

LC-MS; $R_t$=2.28 min, m/z: 444 [M+H]$^+$
Calculated for $C_{19}H_{17}N_5O_6S$. 2×$C_2HF_3O_2$, 2×$H_2O$;
C, 39.05; H, 3.28; N, 9.90; Found:
C, 39.58; H, 3.30; N, 9.80

Example 25

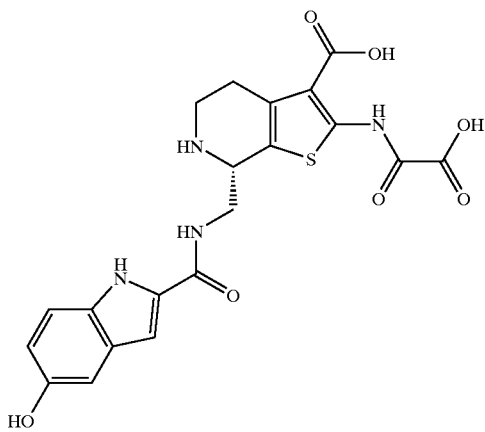

7-(S)-(((5-Hydroxy-1H-indole-2-carbonyl)amino)methyl)-2-(oxalyl-amino)-4,5,6,7-tetrahydro-thieno[2,3-c]pyridine-3-carboxylic acid The title compound was prepared using 5-hydroxy-1H-indole-2-carboxylic acid and 2-amino-7-(S)-aminomethyl-6-(1-(S)-phenyl-ethyl)-4,5,6,7-tetrahydro-thieno[2,3-c]pyridine-3-carboxylic acid tert-butyl ester as the starting material and Method A, B, C and D as described above.

Calculated for $C_{20}H_{18}N_4O_7S$, $1 \times C_2HF_3O_2$, $3 \times H_2O$;

C, 42,18; H, 4,02; N 8,94; Found:

C, 42,25; H, 3,62; N 8,58.

Example 26

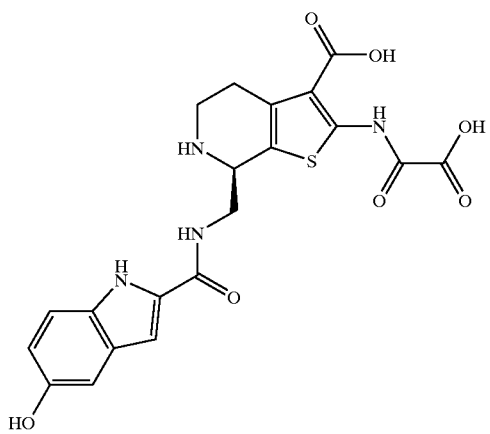

7-(R)-(((5-Hydroxy-1H-indole-2-carbonyl)amino)methyl)-2-(oxalyl -amino)-4,5,6,7-tetrahydro-thieno[2,3-c]pyridine-3-carboxylic acid The title compound was prepared using 5-hydroxy-1H-indole-2-carboxylic acid and 2-amino-7-(R)-aminomethyl-6-(I-(R)-phenyl-ethyl)-4,5,6,7-tetrahydro-thieno[2,3-c]pyridine-3-carboxylic acid tert-butyl ester as the starting material and Method A, B, C and D as described above.

HPLC (A1): $R_t$=12,44 min;

LC-MS; m/z: 459 [M+H]$^+$

Example 27

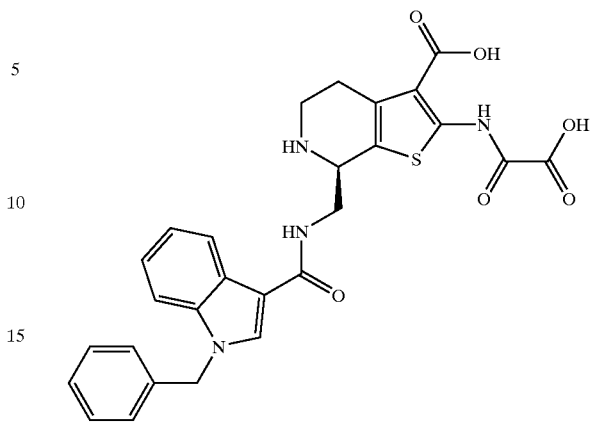

7-(R)-(((1-Benzyl-1H-indole-2-carbonyl)amino)methyl)-2-(oxalyl-amino)-4,5,6,7-tetrahydro-thieno[2,3-c]pyridine-3-carboxylic acid The title compound was prepared using 1-benzyl-1H-indole-3-carboxylic acid and 2-amino-7-(R)-aminomethyl-6-(1-(S)-phenyl-ethyl)-4,5,6,7-tetrahydro-thieno[2,3-c] pyridine-3-carboxylic acid tert-butyl ester as the starting material and Method A, B, C and D as described above.

LC-MS; Rt=1.94 min, m/z: 483 [M+H]$^+$

Example 28

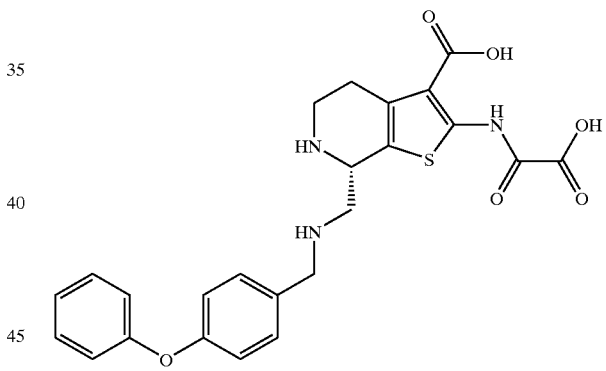

2-(Oxalyl-amino)-7-(S)-((4-phenoxy-benzylamino)methyl)-4,5,6,7-tetrahydro-thieno[2,3-c]pyridine-3-carboxylic acid 2-Amino-7-(S)-aminomethyl-6-(1-(S)-phenyl-ethyl)-4,5,6,7-tetrahydro-thieno[2,3-c]pyridine-3-carboxylic acid tert-butyl ester (500 mg, 1.29 mmol) and 4-phenoxybenzaldehyd (256 mg, 1.29 mmol) was heated to 50° C. in ethanol (30 ml) containing 4A mol sieves (5 ml) for 2 hours. The mixture was cooled to 0° C. on an ice bath before sodium borohydride (98 mg, 1.29 mmol) was added in 3 portions over 45 minutes. The cooling bath was removed and the mixture was stirred for 0.5 hour. The insoluble material was filtered off and washed with dichloromethane. The filtrate was concentrated in vacuo and the residue dissolved in ethyl acetate and washed with aqueous sodium hydrogencarbonate. After drying (MgSO$_4$) the solvent was removed in vacuo. The residue was dissolved in a mixture of acetonitrile (20 ml), triethylamine (130 mg, 1.29 mmol), di-tert-butyl-dicarbonate (282 mg, 1.29 mg) followed by addition of a catalytic amount of 4-N,N-dimethylaminopyridine (5 mg). The reaction mixture was stirred for 16 hours at room temperature and the solvent removed in vacuo. The residue was partitioned between ethyl acetate and water and the organic phase was dried (MgSO₄). After filtration the solvent was removed in vacuo and the residue was re-dissolved in dichloromethane (20 ml). Triethylamine (390 mg, 3.87 mmol) and imidazol-1-yl-oxo-acetic acid tert-butyl ester (760 mg, 3.87 mmol) were added and the solution was left overnight at room temperature, before it was washed with aqueous sodium hydrogencarbonate, dried (MgSO₄), filtered and the solvent evaporated in vacuo. The residue was purified using column chromatography (SiO₂, Flash 40, petrol ether-ethyl acetate 8:1), which afforded 411 mg (40% overall) of 7-((tert-butoxycarbonyl-(4-phenoxy-benzyl)-amino]-methyl}-2-(tert-butoxyoxalyl-amino)-6-(1-phenyl-ethyl)-4,5,6,7-tetrahydro-thieno[2,3-c]pyridine-3-carboxylic acid tert-butyl ester as an oil.

The title compound was obtained using Method C and D as described above.

LC-MS; Rt=2.14 min, m/z: 481 [M+H]$^+$

Calculated for $C_{24}H_{23}N_3O_6S$, 1.5×$C_2HF_3O_2$, 1.5×$H_2O$; C, 47.72; H, 4.08; N, 6.18; Found:

C, 47.94; H, 3.83; N, 6.03.

Example 29

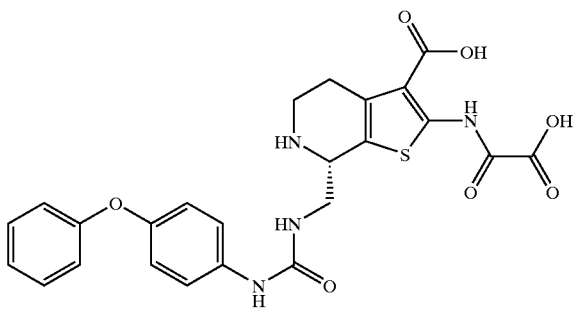

2-(Oxalyl-amino)-7-(S)-(3-(4-phenoxy-phenyl)ureidomethyl)-4,5,6,7-tetrahydro-thieno[2,3-c]pyridine-3-carboxylic acid A solution of 2-amino-7-(S)-aminomethyl-6-(1-(S)-phenyl-ethyl)-4,5,6,7-tetrahydrothieno-[2,3-c]pyridine-3-carboxylic acid tert-butyl ester (250 mg, 0.645 mmol) in dichloromethane (10 ml) was added 4-phenoxyphenyl isocyanate (136 mg, 0.645 mmol) and the reaction mixture was stirred 16 hours at room temperature, before the solvent was removed in vacuo which afforded 386 mg (100%) of 2-amino-7-(S)-(3-(4-phenoxy-phenyl)-ureidomethyl)-6-(1-(S)-phenyl-ethyl)-4,5,6,7-tetrahydro-thieno[2,3-c]pyridine-3-carboxylic acid tert-butyl ester as an oil.

The product was pure for further reaction without purification.

The title compound was obtained using Method B, C and D.

LC-MS; Rt=2.65 min, MS m/z: 511 [M+H]$^+$

Calculated for $C_{24}H_{22}N_4O_7S$, 1×$C_2HF_3O_2$, 1×$H_2O$;

C, 48.60; H, 3.92; N, 8.72; Found:

C, 48.96; H, 3.90; N, 9.10

Example 30

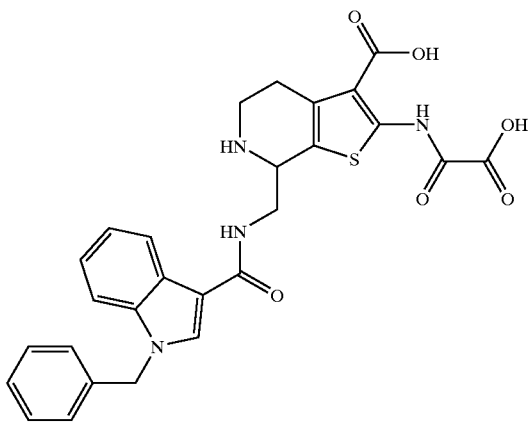

7-(((1Benzyl-1H-indole-3-carbonyl)amino)methyl)-2-(oxalyl-amino)-4,5,6,7-tetrahydro-thieno[2,3-c]pyridine-3-carboxylic acid Diisopropylethylamine (1.8 ml, 10.3 mmol) and 1-(3-dimethylaminopropyl)-3-ethylcarbodiimide hydrochloride (760 mg, 4.0 mmol) were added to a mixture of 1-benzyl-1H-indole-3-carboxylic acid (902 mg, 3.6 mmol) in tetrahydrofuran (50 ml). After stirring for 1 hour, the solution was cooled to 0° C. and a solution of 2-amino-7-aminomethyl-6-(4-methoxy-benzyl)-4,5,6,7-tetrahydro-thieno[2,3-c]pyridine-3-carboxylic acid tert-butyl ester (700 mg, 1.7 mmol) in tetrahydrofuran (7 ml) was added dropwise. The reaction was allowed to slowly warm to room temperature. After 8 hours of stirring the solution was concentrated in vacuo and the residue dissolved in ethyl acetate (40 ml), washed with saturated aqueous sodium bicarbonate (2×30 ml), brine (1×30 ml), dried (MgSO₄), filtered, and the solvent evaporated in vacuo. The residue was purified by silica gel chromatography using a mixture of hexane/ethyl acetate/triethylamine, (50:50:1) as eluent, which afforded 560 mg (51%) of 2-amino-7-(((1-benzyl-1H-indole-3-carbonyl)amino)methyl)-6-(4-methoxy-benzyl)-4,5,6,7-tetrahydro-thieno[2,3-c]pyridine-3-carboxylic acid tert-butyl ester as a solid.

$^1$H-NMR (300 MHz, CDCl₃): δ 8.13 (dd, 1H, J=5 Hz, J=3 Hz), 7.87 (s, 1H), 7.66-7.32 (m, 8H), 6.91 (d, 2H, J=9 Hz), 6.81 (m, 1H), 6.55-6.42 (m, 2H), 6.25-6.18 (m, 2H), 5.67-5.49 (m, 4H), 4.64-2.79 (m, 12H), 1.79 (s, 9H).

To a solution of 2-amino-7-(((1-benzyl-1H-indole-3-carbonyl)-amino)-methyl)-6-(4-methoxy-benzyl)-4,5,6,7-tetrahydro-thieno[2,3-c]pyridine-3-carboxylic acid tert-butyl ester (560 mg, 0.88 mmol) in dichloromethane (20 ml) was added midazol-1-yl-oxo-acetic acid tert-butyl ester (565 mg, 2.9 mmol). After stirring for 18 hours at room temperature, the reaction mixture was washed with saturated aqueous sodium bicarbonate (2×20 ml) and brine (1×20 ml). The organic phase was dried (MgSO₄), filtered, and the solvent evaporated in vacuo. The residue was purified by silica gel chromatography using a mixture of hexane/ethyl acetate/triethylamine (50:50:1) as eluent, which afforded 592 mg (88%) of 7-(((1-benzyl-1H-indole-3-carbonyl)-amino)-methyl)-2-(tert-butoxyoxalyl-amino)-6-(4methoxy-benzyl)-4,5,6,7-tetrahydro-thieno[2,3-c]pyridine-3-carboxylic acid tert-butyl ester as a solid.

$^1$H-NMR (300 MHz, CDCl₃): δ 12.56 (s, 1H), 7.92 (dd, 1H, J=6 Hz and J=3 Hz), 7.68 (s, 1H), 7.43-7.14 (m, 8H), 6.71 (d, 2H, J=9 Hz), 6.55 (d, 1H, J=6 Hz), 5.37 (s, 2H), 4.08-2.70 (m, 12H), 1.63 (s, 18H).

10% Pd/C (612 mg) and ammonium formate (614 mg) was added to a mixture of 7-(((1-benzyl-1H-indole-3-carbonyl)-amino)-methyl)-2-(tert-butoxyoxalyl-amino)-6-(4-methoxy-benzyl)-4,5,6,7-tetrahydro-thieno[2,3-c]pyridine-3-carboxylic acid tert-butyl ester (592 mg, 0.77 mmol) in 10% formic acid in methanol (10 ml). After stirring at 40° C. for 48 hours, the catalyst was filtered off through celite and washed with methanol. The volatiles were evaporated in vacuo and the residue was dissolved in dichloromethane (30 ml), washed with saturated aqueous sodium bicarbonate (2×20 ml) and brine (1×20 ml). The organic phase was dried (MgSO$_4$), filtered, and concentrated in vacuo. The residue was purified by chromatotron (ethyl acetate:triethylamine, 99:1), which afforded 22 mg (4%) of 7-(((1-benzyl-1H-indole-3-carbonyl)-amino)-methyl)-2-(tert-butoxyoxalyl-amino)-4,5,6,7-tetrahydro-thieno[2,3-c]pyridine-3-carboxylic acid tert-butyl ester (A) and 40 mg (8%) of 7-(((1-benzyl-1H-indole-3-carbonyl)-amino)-methyl)-2-(tert-butoxyoxalyl-amino)-6-methyl-4,5,6,7-tetrahydro-thieno[2,3-c]pyridine-3-carboxylic acid tert-butyl ester (B).

(A): $^1$H-NMR (300 MHz, CDCl$_3$): δ 12.54 (s, 1H), 7.97-7.91 (m, 1H), 7.78 (s, 1H), 7.39-7.10 (s, 7H), 6.66 (m, 1H), 5.30 (s, 2H), 4.29-4.21 (m, 1H), 4.03-3.92 (m, 1H), 3.60-3.48 (m, 1H), 3.31-3.17 (m, 1H), 3.08-2.96 (m, 1H), 2.92-2.76 (m, 2H), 1.60 (s, 9H), 1.59 (s, 9H).

(B): $^1$H-NMR (300 MHz, CDCl$_3$): δ 12.49 (s, 1H), 7.77 (m, 2H), 7.35-7.09 (m, 7H), 6.63 (m,1H), 5.31 (s, 2H), 3.98 (dt, 1H, J=13 Hz and J=6 Hz), 3.76-3.59 (m, 2H), 3.17-3.06 (m, 1H), 3.01-2.69 (m, 3H), 2.53 (s, 3H), 2.04 (s, 1H), 1.61 (s, 9H), 1.59 (s, 9H).

7-(((1-Benzyl-1H-indole-3-carbonyl)-amino)-methyl)-2-(tert-butoxyoxalyl-amino)-4,5,6,7-tetrahydro-thieno[2,3-c]pyridine-3-carboxylic acid tert-butyl ester (22 mg, 0.034 mmol) was dissolved in 30% trifluoroacetic acid in dichloromethane (4 ml). The solution was left open to the atmosphere without stirring. After 24 hours the precipitate was filtered off and washed with diethyl ether, affording 20 mg (90%) of the title compound as a solid.

$^1$H-NMR (400 MHz, DMSO-d$_6$): δ 12.38 (s, 1H), 9.55 (s, 1H), 9.16 (s, 1H), 8.41 (s, 1H), 8.55 (s, 1H, J=6 Hz), 8.20 (s, 2H), 7.40-7.14 (m, 6H), 4.77 (s, 1H), 3.90-2.90 (m, 7H partially obscured by water).

Example 31

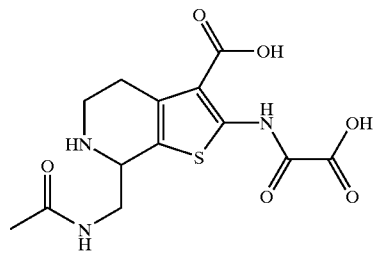

7-(Acetylamino-methyl)-2-(oxalyl-amino)-4,5,6,7-tetrahydro-thieno[2,3-c]pyridine-carboxylic acid 2-Amino-7-aminomethyl-6-(4-methoxy-benzyl)-4,5,6,7-tetrahydro-thieno[2,3-c]pyridine-3-carboxylic acid tert-butyl ester (141 mg, 0.25 mmol, prepared as described in Example 1) and diisopropypethylamine (75 μl, 0.43 mmol) were dissolved in dichloromethane (10 ml) with stirring. The flask was then flush with nitrogen and sealed with a rubber septum before being cooled to 0° C. Acetyl chloride (20 μl, 0.28 mmol) was added dropwise to the solution, which was then warmed slowly to room temperature. After 2 hours of stirring, the reaction was concentrated to dryness in vacuo. The residue was purified by silica gel chromatography using a mixture of hexane/ethyl acetate (3:1) as eluent, which afforded 95 mg (86%) of 7-(acetylamino-methyl)-2-amino-6-(4-methoxy-benzyl)-4,5,6,7-tetrahydro-thieno[2,3-c]pyridine-3-carboxylic acid tert-butyl ester as a solid.

$^1$H-NMR (300 MHz, CDCl$_3$): δ 7.23 (d, 2H, J=9 Hz), 6.88 (d, 2H, J=9 Hz), 6.08 (s, 2H), 5.93 (bs, 1H), 3.81 (s, 3H), 3.73-3.59 (m, 3H), 3.46 (dd, 1H, J=9 Hz, J=4 Hz), 3.18-3.00 (m, 2H), 2.93-2.73 (m, 2H), 2.70-2.59 (m, 1H), 1.86 (s, 3H).

To a solution of 7-(acetylamino-methyl)-2-amino-6-(4-methoxy-benzyl)-4,5,6,7-tetrahydro-thieno[2,3-c]pyridine-3-carboxylic acid tert-butyl ester (95 mg, 0.21 mmol) in dichloromethane (10 ml) was added midazol-1-yl-oxo-acetic acid tert-butyl ester (110 mg, 0.56 mmol). After stirring for 18 hours at room temperature, the reaction solution was concentrated to dryness in vacuo. The residue was purified by silica gel chromatography using a mixture of hexane/ethyl acetate (3:1), which afforded 96 mg (80%) of 7-(acetylamino-methyl)-2-(tert-butoxyoxalyl-amino)-6-(4-methoxy-benzyl)-4,5,6,7-tetrahydro-thieno[2,3-c]pyridine-3-carboxylic acid tert-butyl ester as a solid.

$^1$H-NMR (300 MHz, CDCl$_3$): δ 12.53 (s, 1H), 7.22 (d, 2H, J=11 Hz), 6.88 (d, 2H, J=9 Hz), 5.88 (bs, 1H), 3.81 (s, 3H), 3.74-3.63 (m, 4H), 3.23-3.11 (m, 2H), 2.99-2.83 (m, 2H), 2.77-2.69 (m,1H), 1.89 (s, 3H), 1.61 (s, 18H).

10% Pd/C (101 mg) was added to 7-(acetylamino-methyl)-2-(tert-butoxyoxalyl-amino)-6-(4-methoxy-benzyl)-4,5,6,7-tetrahydro-thieno[2,3-c]pyridine-3-carboxylic acid tert-butyl ester (96 mg, 0.17 mmol) dissolved in 10% formic acid in methanol (10 ml). After stirring at room temperature for 48 hours, the catalyst was filtered off through celite and wash with methanol. The solvent was evaporated in vacuo and the residue purified by chromatotron (ethyl acetate/triethylamine, 99:1), which afforded 50 mg (65%) of 7-(acetylamino-methyl)-2-(tert-butoxyoxalyl-amino)-4,5,6,7-tetrahydro-thieno[2,3-c]pyridine-3-carboxylic acid tert-butyl ester.

$^1$H-NMR (300 MHz, CDCl$_3$): δ 12.55 (s, 1H), 4.77 (s, 1H), 3.96 (d, 1H, J=10 Hz), 3.65 (s, 2H), 3.34-3.11 (m, 3H), 2.01 (s, 3H), 1.62 (s, 9H), 1.60 (s, 9H).

7-(Acetylamino-methyl)-2-(tert-butoxyoxalyl-amino)-4,5,6,7-tetrahydro-thieno[2,3-c]pyridine-3-carboxylic acid tert-butyl ester (50 mg, 0.11 mmol) was dissolved in 30% trifluoroacetic acid in dichloromethane (4 ml). The solution was left open to the atmosphere without stirring. After 24 hours the precipitate was filtered off and washed with diethyl ether, affording 45 mg (90%) of the title compound as a solid.

$^1$H-NMR (400 MHz, DMSO-d$_6$): δ 12.37 (s, 1H), 9.50 (s, 1H), 8.97 (s, 1H), 8.36 (s, 1H), 4.61 (s, 1H), 3.70-2.95 (m, 7H partially obscured by water), 1.88 (s, 3H).

LC-MS (APCI+): m/z: 342 [M+H]$^+$; Rt=0.97 min.

Example 32

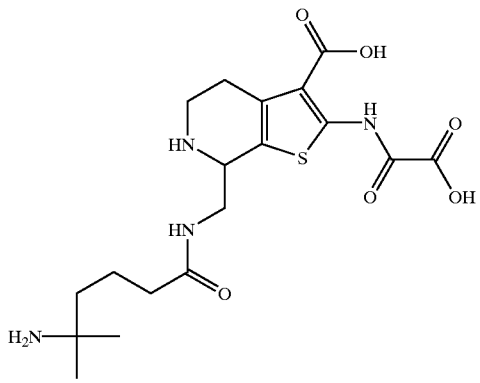

7-((5-Amino-5-methyl-hexanoylamino)methyl)-2-(oxalyl-amino)-
4,5,6,7-tetrahydro-thieno[2,3-c]pyridine-3-carboxylic acid The title compound was made in a similar way as described in Example 43 using 5-tert-butoxycarbonylamino-5-methyl-hexanoic acid and 2-amino-7-aminomethyl-6-(4-methoxy-benzyl)-4,5,6,7-tetrahydro-thieno[2,3-c]pyridine-3-carboxylic acid tert-butyl ester as starting material.

LC-MS; Rt=0,85 min, m/z: 427 [M+H]$^+$

Example 33 (52-1261-1A)

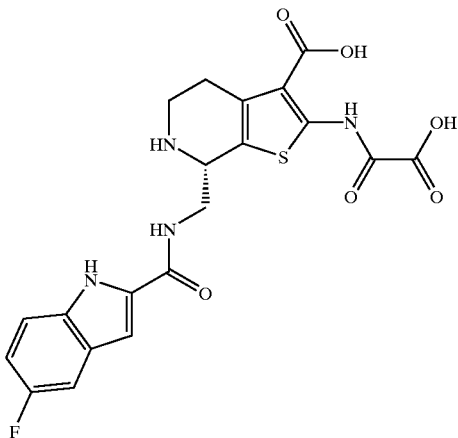

7-(S)-(((5-Fluoro-1H-indole-2-carbonyl)amino)methyl)-2-
(oxalyl-amino)-4,5,6,7-tetrahydro-thieno[2,3-c]pyridine-
3-carboxylic acid The title compound was prepared using 5-fluoro-1H-indole-2-carboxylic acid and 2-amino-7-(S)-aminomethyl-6-(1-(S)-phenyl-ethyl)-4,5,6,7-tetrahydro-thieno[2,3-c]pyridine-3-carboxylic acid tert-butyl ester as the starting material and Method A, B, C and D as described above.

Calculated for $C_{20}H_{17}FN_4O_6S$ 4/3×$C_2HF_3O_2$, 2/3×$H_2O$

C, 43.60; H, 3.17; N, 8.97; Found

C, 43.59; H, 3.24; N, 8.78

LC-MS: m/z: 461 [M+H]$^+$

Example 34 (52-1269-1A)

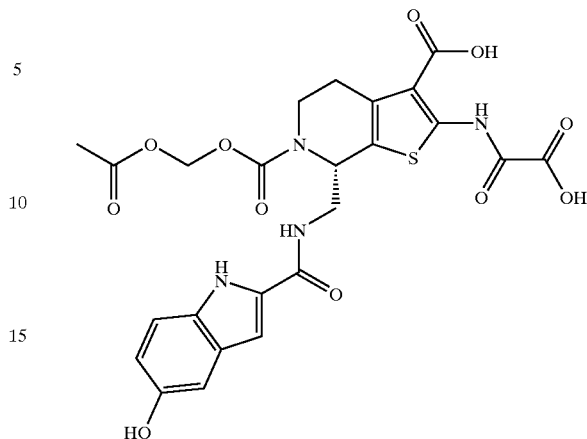

7-(S)-(((5-Hydroxy-1H-indole-2-carbonyl)amino)methyl)-2-
(oxalyl-amino)-4,7-dihydro-5H-thieno[2,3-c]pyridine-3,
6-dicarboxylic acid 6-acetoxymethyl ester 2-(tert-Butoxyoxalyl-amino)-7-(S)-(((5-hydroxy-1H-indole-2-carbonyl)amino)-methyl)-4,5,6,7-tetrahydro-thieno[2,3-c]pyridine-3-carboxylic acid tert-butyl ester was produced using 5-benzyloxy-1H-indole-2-carboxylic acid and 2-amino-7-(S)-aminomethyl-6-(1-(S)-phenyl-ethyl)-4,5,6,7-tetrahydro-thieno[2,3-c]pyridine-3-carboxylic acid tert-butyl ester as the starting material and Method A, B, and C as described above.

A solution of (S)-2-(tert-butoxyoxalyl-amino)-7-(S)-(((5-hydroxy-1H-indole-2-carbonyl)amino)methyl)-4,5,6,7-tetrahydro-thieno[2,3-c]pyridine-3-carboxylic acid tert-butyl ester (233 mg, 0.41 mmol), acetic acid 4-nitro-phenoxycarbonyl-oxymethyl ester (104 mg, 0.41 mmol) and N,N-diisopropylethylamine (53 mg, 0.41 mmol) was heated to 50° C. in acetonitrile (30 mL) for 4 hours. The solvent was removed in vacuo and the residue was redissolved in ethyl acetate (50 mL), washed with sodium bicarbonate (50 mL) and dried (MgSO$_4$). The crude products were purified by flash column chromatography (petrol ether-ethyl acetate (1:1). A mixture of mono- and di-acylated products were obtained, yield 45 mg (16%).

A solution of 2-(tert-butoxyoxalyl-amino)-7-(S)-(((5-hydroxy-1H-indole-2-carbonyl)amino)methyl)-4,7-dihydro-5H-thieno[2,3-c]pyridine-3,6-dicarboxylic acid 6-acetoxymethyl ester 3-tert-butyl ester and 7-(S)-(((5-acetoxymethoxy-carbonyloxy-1H-indole-2-carbonyl)amino)methyl)-2-(tert-butoxyoxalyl-amino)-4,7-dihydro-5H-thieno[2,3-c]pyridine-3,6-dicarboxylic acid 6-acetoxymethyl ester 3-tert-butyl ester (45 mg, 0.07 mmol) was stirred in trifluoroacetic acid:dichloromethane (2 mL, 1:1, v/v) for 16 hours. Diethyl ether (2 mL) was added and the mixture was centrifuged at 4000 rpm for 3 minutes. The liquors were decanted from the precipitate and the crude products were purified by reverse phase HPLC [Xterra MS C-18 column, 25 mL/min flow rate, 10% acetonitril/water-100% acetonitril (0.01% TFA) gradient over 11 minutes]. Absorbance was measured at 210 nm.

This afforded 13 mg of the title compound.

Calculated for $C_{24}H_{22}N_4O_{11}S$, 0.5×$C_2HF_3O_2$, 0.5×$H_2O$

C, 46.88; H, 3.70; N, 8.75; Found

C, 46.84; H, 3.98; N, 8.91

LC-MS: m/z: 575 [M+H]$^+$

Example 35 (52-1270-1A)

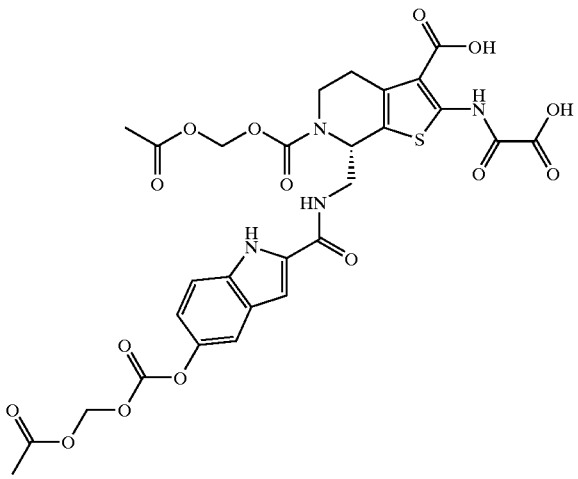

7-(S)-(((5-Acetoxymethoxycarbonyloxy-1H-indole-2-carbonyl)amino)methyl)-2-(oxalyl-amino)-4,7-dihydro-5H-thieno[2,3-c]pyridine-3,6-dicarboxylic acid 6-acetoxymethyl ester As the second eluting compound in Example 34, 13 mg of the title compound was isolated.

Calculated for $C_{28}H_{26}N_4O_{15}S$, $0.5 \times C_2HF_3O_2$
C, 46.59; H, 3.57; N, 7.49; Found
C, 46.27; H, 3.41; N, 7.43
LC-MS: m/z: 691 [M+H]$^+$

Example 36 (52-1280-1A)

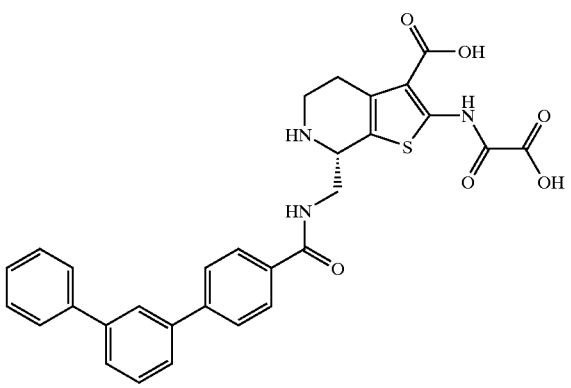

2-(Oxalyl-amino)-7-(S)-((([1,1';3',1"]terphenyl-4-carbonyl)aminomethyl)-4,5,6,7-tetrahydro-thieno[2,3-c]pyridine-3-carboxylic acid The title compound was prepared using [1,1';3',1"]Terphenyl-4"-carboxylic acid and 2-amino-7-(S)-aminomethyl-6-(1-(S)-phenyl-ethyl)-4,5,6,7-tetrahydro-thieno[2,3-c]pyridine-3-carboxylic acid tert-butyl ester as the starting material and Method A, B, C and D as described above.

Calculated for $C_{30}H_{25}N_3O_6S$, $4/3 \times C_2HF_3O_2$, $8/3 \times H_2O$
C, 51.92; H, 4.22; N, 5.56; Found
C, 52.42; H, 4.41; N, 5.08
LC-MS: Rt: 5.21 min., m/z: 556.1 [M+H]$^+$

Example 37 (52-1281-1A)

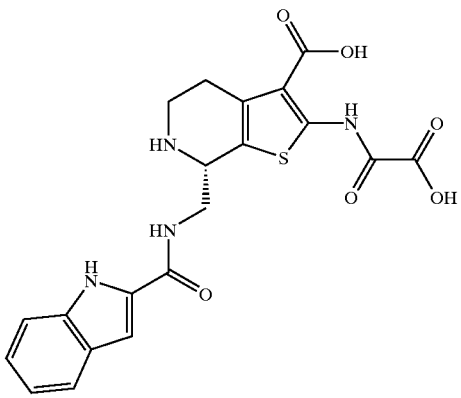

7-(S)-(((1H-Indole-2-carbonyl)amino)methyl)-2-(oxalyl-amino)-4,5,6,7-tetrahydro-thieno[2,3-c]pyridine-3-carboxylic acid The title compound was prepared using 1H-indole-2-carboxylic acid and 2-amino-7-(S)-aminomethyl-6-(1-(S)-phenyl-ethyl)-4,5,6,7-tetrahydro-thieno[2,3-c]pyridine-3-carboxylic acid tert-butyl ester as the starting material and Method A, B, C and D as described above.

LC-MS: m/z: 443 [M+H]$^+$

Example 38 (OC 297963)

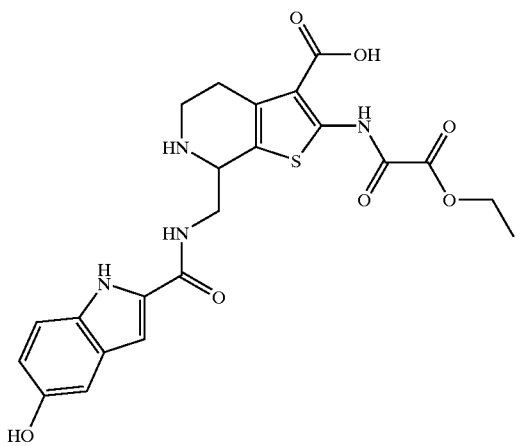

2-(Ethoxyoxalyl-amino)-7-(((5-hydroxy-1H-indole-2-carbonyl)amino)methyl)-4,5,6,7-tetrahydro-thieno[2,3-c]pyridine-3-carboxylic acid 2-Amino-7-(((5-benzyloxy-1H-indole-2-carbonyl)amino)methyl)-6-(4-methoxy-benzyl)-4,5,6,7-tetrahydro[2,3-c]pyridine-3-carboxylic acid tert-butyl ester (157 mg, 0.24 mmol) and imidazol-1-yl-oxo-acetic acid ethyl ester (1.2 mmol, 5 eq.) were added to dichloromethane (3 mL), and the reaction was stirred at room temperature under $N_2$ for 8 hours. The reaction mixture was added to ethyl acetate (100 mL), washed with $H_2O$ (100 mL) and brine (100 mL), dried (MgSO$_4$), filtered, and concentrated in vacuo. To the crude residue was added dichloromethane (1 mL) and the solution was flushed through a short plug of silica gel affording 177 mg (98%) of 2-(ethoxyoxalyl-amino)-7-(((5-benzyloxy-1H-indole-2-carbonyl)amino)methyl)-6-(4-methoxy-benzyl)-4, 5,6,7-tetrahydro[2,3-c]pyridine-3-carboxylic acid ethyl ester which was not purified further.

To 2-(ethoxyoxalyl-amino)-7-(((5-benzyloxy-1H-indole-2-carbonyl)amino)-methyl)-4,5,6,7-tetrahydro[2,3-c] pyridine-3-carboxylic acid tert-butyl ester (34 mg) was added trifluoroacetic acid (50% in dichloromethane) at 0° C. The reaction mixture was allowed to warm to room temperature and stirred for 1.5 hours. The crude solution was concentrated in vacuo and further dried under high vacuum to provide 28 mg (90%) of the title compound.

2-((Ethoxyoxyoxalyl)amino)-7-(((5-benzyloxy-1H-indole-2-carbonyl)amino)-methyl)-6-(4-methoxy-benzyl)-4,5,6,7-tetrahydro[2,3-c]pyridine-3-carboxylic acid (100 mg) was added to test tubes (18×150mm) using ethyl acetate (3 mL) and ethanol (3 mL). To the solutions was added Pearlman's catalyst (60 mg), Degussa Pd/C (E101 NE/W, 40 mg), and trifluoroacetic acid (0.6 mL). The reaction mixtures (in test tubes) were added to a Parr jar and hydrogenated at 50 psi for 36 hours. The reaction mixtures were then filtered through a plug of celite using acetonitrile and concentrated in vacuo. The crude material was purified by preparative chromatography using a mixture of dichloromethane/ methanol (10:1) as eluent, which afforded 18 mg of the title compound as an oil.

$^1$H-NMR (300 MHz, CD$_3$OD): δ 8.17 (bs, 1H), 7.21 (s, 1H), 6.97 (d, 1H, J=13), 6.88 (d, 1H, J=12), 6.82 (dd, 1H, J$_1$=9, and J$_2$=2.5), 4.38 (q, 2H, J=6.9), 4.19 (m, 1H), 3.89 (m, 2H), 3.64 (m, 2H), 1.38 (t, 3H, J=7.2).

LC-MS: m/z: 487.16 [M+H]$^+$

Example 39 (OC 297983)

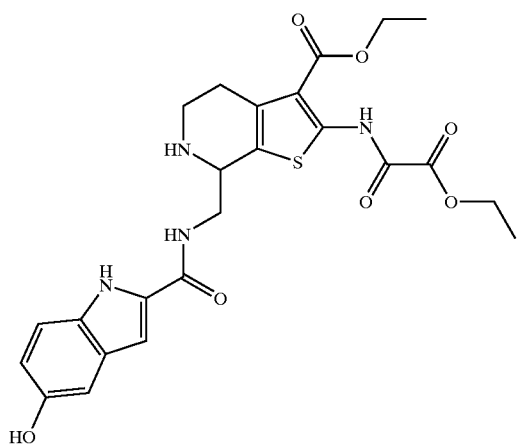

2-(Ethoxyoxalyl-amino)-7-(((5-hydroxy-1H-indole-2-carbonyl)amino)methyl)-4,5,6,7-tetrahydro-thieno[2,3-c]pyridine-3-carboxylic acid ethyl ester 2-Amino-7-aminomethyl-6-(4-methoxy-benzyl)-4,5,6,7-tetrahydro-thieno[2,3-c]pyridine-3-carboxylic acid ethyl ester (350 mg, 0.92 mmol), 5-benzyloxy-1H-indole-2-carboxylic acid (300 mg, 1.1 mmol), 1-(3-(dimethyl-amino) propyl)-3-ethylcarbodiimide hydrochloride (270 mg, 1.4 mmol), and 1-hydroxy-benzotriazole (190 mg, 1.4 mmol) in N,N-dimethylformamide (10 mL) was stirred under N$_2$ at room temperature for 12 hours. The reaction mixture was added to dichloromethane (100 mL) and washed with water (100 mL). The aqueous layer was back extracted with dichloromethane (50 mL). The combined organic phases were washed with brine (150 mL), dried MgSO$_4$), filtered, and concentrated in vacuo. The crude residue was chromatographed on silica gel column using a mixture of dichloromethane/ ethyl acetate (5:1) as eluent, which provided 452 mg (78%) of 2-amino-7-(((5-benzyloxy-1H-indole-2-carbonyl)-amino)methyl)-6-(4-methoxy-benzyl)-4,5,6,7-tetrahydro[2,3-c]pyridine-3-carboxylic acid ethyl ester as a solid.

$^1$H-NMR (300 MHz, CDCl$_3$): δ 9.97 (bs, 1H), 8.82 (bs, 1H), 7.45 (m, 2H), 7.39 (m, 3H), 7.32 (m, 4H), 7.08 (d, 2H, J=7.8), 6.99 (dd, 1H, J$_1$=8.7, J$_2$=2.1), 6.59 (bs, 2H), 6.47 (d, 2H, J=8.4), 5.05 (s, 3H), 4.27 (q, 2H, J=6.9), 4.21 (m, 2H), 3.96 (m, 2H), 3.78 (m, 1H), 3.52 (m, 3H), 3.28 (s, 3H), 1.34 (t, 3H, J=7.2).

LC-MS: m/z: 625.41 [M+H]$^+$

2-Amino-7-(((5-benzyloxy-1H-indole-2-carbonyl)amino) methyl)-6-(4-methoxy-benzyl)-4,5,6,7-tetrahydro[2,3-c] pyridine-3-carboxylic acid ethyl ester (150 mg, 0.24 mmol) and imidazol-1-yl-oxo-acetic acid ethyl ester (1.2 mmol, 5 eq.) were added to dichloromethane (3 mL), and the reaction was stirred at room temperature under N$_2$ for 8 hours. The reaction mixture was added to ethyl acetate (100 mL), washed with H$_2$O (100 mL) and brine (100 mL), dried (MgSO$_4$), filtered, and concentrated in vacuo. To the crude residue was added dichloromethane (1 mL) and the solution was flushed through a short plug of silica gel affording 170 mg (98%) of 2-((2,2-dimethyl-propoxyoxalyl)amino)-7-(((5-benzyloxy-1H-indole-2-carbonyl)amino)methyl)-6-(4-methoxy-benzyl)-4,5,6,7-tetrahydro[2,3-c]pyridine-3-carboxylic acid ethyl ester which was not purified further.

LC-MS: m/z: 725.21 [M+H]$^+$ 2-((Ethoxyoxyoxalyl)amino)-7-(((5-benzyloxy-1H-indole-2-carbonyl)amino)-methyl)-6-(4-methoxy-benzyl)-4,5,6,7-tetrahydro[2,3-c]pyridine-3-carboxylic acid ethyl ester (100 mg) was added to test tubes (18×150 mm) using ethyl acetate (3 mL) and ethanol (3 mL). To the solutions was added Pearlman's catalyst (60 mg), Degussa Pd/C (E101 NE/W, 40 mg), and trifluoroacetic acid (0.6 mL). The reaction mixtures (in test tubes) were added to a Parr jar and hydrogenated at 50 psi for 36 hours. The reaction mixtures were then filtered through a plug of celite using acetonitrile and concentrated in vacuo. The crude material was purified by preparative chromatography using a mixture of dichloromethane/methanol (10:1) as eluent, which afforded 10 mg of the title compound as an oil.

$^1$H-NMR (300 MHz, CD$_3$OD): δ 8.4 (bs, 1H), 7.16 (d, 1H, J=9.0), 6.89 (d, 1H, J=2.1), 6.82 (s, 1H), 6.76 (dd,1H, J$_1$=8.7, and J$_2$=2.4), 4.35 (q, 2H, J=7.2), 4.29 (q, 2H, J=7.2), 3.81 (dd, 1H, J$_1$=14.1, and J$_2$=4.2), 3.69 (m, 1H), 3.55 (m, 1H), 3.45 (dd, 1H, J$_1$=13.8, and J$_2$=8.7), 3.24 (m,1H, eclipsed by solvent), 3.94 (m, 1H), 3.84 (bm, 2H), 1.33 (t, 3H, J=7.2), 1.32 (t, 3H, J=7.0).

LC-MS: m/z: 515.5 [M+H]$^+$

Example 40 (OC 297965)

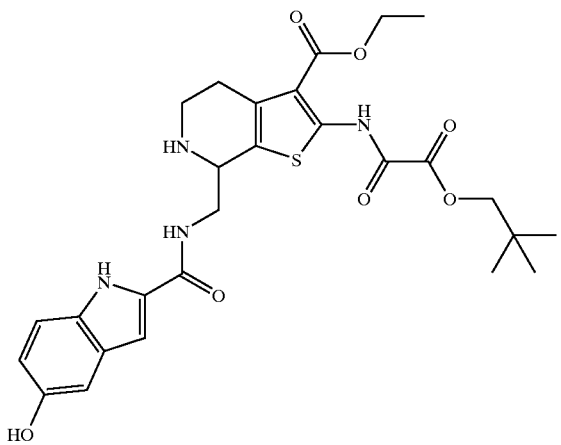

2-((2,2-Dimethyl-propoxyoxalyl)amino)-7-(((5-hydroxy-1H-indole-2-carbonyl)-amino)methyl)-4,5,6,7-tetrahydro-thieno[2,3-c]pyridine-3-carboxylic acid ethyl ester 2-Amino-7-aminomethyl-6-(4-methoxy-benzyl)-4,5,6,7-tetrahydro-thieno[2,3-c]pyridine-3-carboxylic acid tert-butyl ester (350 mg, 0.92 mmol), 5-benzyloxy-1H-indole-2-carboxylic acid (300 mg, 1.1 mmol), 1-(3-(dimethylamino)propyl)-3-ethylcarbodiimide hydrochloride (270 mg, 1.4 mmol), and 1-hydroxy-benzotriazole (190 mg, 1.4 mmol) in N,N-dimethylformamide (10 mL) was stirred under $N_2$ at room temperature for 12 hours. The reaction mixture was added to dichloromethane (100 mL) and washed with water (100 mL). The aqueous layer was back extracted with dichloromethane (50 mL). The combined organic phases were washed with brine (150 mL), dried $MgSO_4$), filtered, and concentrated in vacuo. The crude residue was chromatographed on silica gel column using a mixture of dichloromethane/ ethyl acetate (5:1) as eluent, which provided 452 mg (78%) of 2-amino-7-(((5-benzyloxy-1H-indole-2-carbonyl)-amino)methyl)-6-(4-methoxy-benzyl)-4,5,6,7-tetrahydro[2,3-c]pyridine-3-carboxylic acid ethyl ester as a solid.

$^1$H-NMR (300 MHz, $CDCl_3$): δ 9.97 (bs, 1H), 8.82 (bs, 1H), 7.45 (m, 2H), 7.39 (m, 3H), 7.32 (m, 4H), 7.08 (d, 2H, J=7.8), 6.99 (dd, 1H, $J_1$=8.7, $J_2$=2.1), 6.59 (bs, 2H), 6.47 (d, 2H, J=8.4), 5.05 (s, 3H), 4.27 (q, 2H, J=6.9), 4.21 (m, 2H), 3.96 (m, 2H), 3.78 (m, 1H), 3.52 (m, 3H), 3.28 (s, 3H), 1.34 (t, 3H, J=7.2).

LC-MS: m/z: 625.41 [M+H]$^+$

2-Amino-7-(((5-benzyloxy-1H-indole-2-carbonyl)amino)methyl)-6-(4-methoxy-benzyl)-4,5,6,7-tetrahydro[2,3-c]pyridine-3-carboxylic acid ethyl ester (150 mg, 0.24 mmol) and imidazol-1-yl-oxo-acetic acid 2,2-dimethyl-propyl ester (1.2 mmol, 5 eq.) were added to dichloromethane (3 mL), and the reaction was stirred at room temperature under $N_2$ for 8 hours. The reaction mixture was added to ethyl acetate (100 mL), washed with $H_2O$ (100 mL) and brine (100 mL), dried ($MgSO_4$), filtered, and concentrated in vacuo. To the crude residue was added dichloromethane (1 mL) and the solution was flushed through a short plug of silica gel affording 180 mg (98%) of 2-((2,2-dimethyl-propoxyoxalyl)-amino)-7-(((5-benzyloxy-1H-indole-2-carbonyl)amino)methyl)-6-(4-methoxy-benzyl) -4,5,6,7-tetrahydro[2,3-c]pyridine-3-carboxylic acid ethyl ester which was not purified further.

LC-MS: m/z: 767.23 [M+H]$^+$ 2-((2,2-Dimethyl-propoxyoxalyl)amino)-7-(((5-benzyloxy-1H-indole-2-carbonyl)amino)methyl)-6-(4-methoxy-benzyl)-4,5,6,7-tetrahydro[2,3-c]pyridine-3–10 carboxylic acid ethyl ester (100 mg) was added to test tubes (18×50 mm) using ethyl acetate (3 mL) and ethanol (3 mL). To the solutions was added Pearlman's catalyst (60 mg), Degussa Pd/C (E101 NE/W, 40 mg), and trifluoroacetic acid (0.6 mL). The reaction mixtures (in test tubes) were added to a Parr jar and hydrogenated at 50 psi for 36 hours. The reaction mixtures were then filtered through a plug of celite using acetonitrile and concentrated in vacuo. The crude material was purified by preparative chromatography using a mixture of dichloromethane/methanol (10:1) as eluent, which afforded 10 mg of the title compound as an oil.

$^1$H-NMR (300 MHz, $CD_3OD$): δ 7.25 (d, 1H, J=8.7), 6.95 (d, 1H, J=0.9), 6.93 (d, 1H, J=2.1), 6.78 (dd, 1H, $J_1$=9.0, and $J_2$=2.7), 4.37 (q, 2H, J=7.2), 4.03 (s, 2H), 3.79-3.60 (m, 3H), 3.35 (m, 1H), 3.22 (m, 1H), 3.04 (dd, 1H, $J_1$=13.8, and $J_2$=6.6), 2.94 (m, 2H), 1.38 (t, 3H, J=7.2), 1.03 (bs, 7H).

LC-MS: m/z: 557.16 [M+H]$^+$

Example 41 (OC 297964)

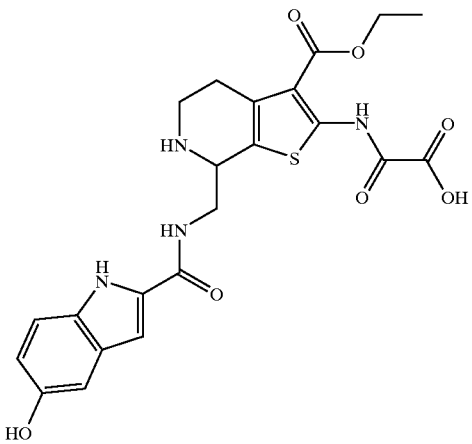

7-(((5-Hydroxy-1H-indole-2-carbonyl)amino)methyl)-2-(oxalyl-amino)
4,7-dihydro-5H-thieno[2,3-c]pyridine-3-carboxylic acid ethyl ester 2-Amino-7-aminomethyl-6-(4-methoxy-benzyl)-4,5,6,7-tetrahydro-thieno[2,3-c]pyridine-3-carboxylic acid tert-butyl ester (350 mg, 0.92 mmol), 5-benzyloxy -1H-indole-2-carboxylic acid (300 mg, 1.1 mmol), 1-(3-(dimethylamino)propyl)-3-ethylcarbodiimide hydrochloride (270 mg, 1.4 mmol), and 1-hydroxy-benzotriazole (190 mg, 1.4 mmol) in N,N-dimethylformamide (10 mL) was stirred under $N_2$ at room temperature for 12 hours. The reaction mixture was added to dichloromethane (100 mL) and washed with water (100 mL). The aqueous layer was back extracted with dichloromethane (50 mL). The combined organic phases were washed with brine (150 mL), dried $MgSO_4$), filtered, and concentrated in vacuo. The crude residue was chromatographed on silica gel column using a mixture of dichloromethane/ ethyl acetate (5:1) as eluent, which provided 452 mg (78%) of 2-amino-7-(((5-benzyloxy-1H-indole-2-carbonyl)-amino)methyl)-6-(4-methoxy-benzyl)-4,5,6,7-tetrahydro[2,3-c]pyridine-3-carboxylic acid ethyl ester as a solid.

$^1$H-NMR (300 MHz, $CDCl_3$): δ 9.97 (bs, 1H), 8.82 (bs, 1H), 7.45 (m, 2H), 7.39 (m, 3H), 7.32 (m, 4H), 7.08 (d, 2H, J=7.8), 6.99 (dd,1H, $J_1$=8.7, $J_2$=2.1), 6.59 (bs, 2H), 6.47 (d,

2H, J=8.4), 5.05 (s, 3H), 4.27 (q, 2H, J=6.9), 4.21 (m, 2), 3.96 (m, 2H), 3.78 (m, 1H), 3.52 (m, 3H), 3.28 (s, 3H), 1.34 (t, 3H, J=7.2).

LC-MS: m/z: 625.41 [M+H]+

2-Amino-7-(((5-benzyloxy-1H-indole-2-carbonyl)amino) methyl)-6-(4-methoxy-benzyl)-4,5,6,7-tetrahydro[2,3-c] pyridine-3-carboxylic acid ethyl ester (150 mg, 0.24 mmol) and imidazol-1-yl-oxo-acetic acid tert-butyl ester (1.2 mmol, 5 eq.) were added to dichloromethane (3 mL), and the reaction was stirred at room temperature under $N_2$ for 8 hours. The reaction mixture was added to ethyl acetate (100 mL), washed with $H_2O$ (100 mL) and brine (100 mL), dried ($MgSO_4$), filtered, and concentrated in vacuo. To the crude residue was added dichloromethane (1 mL) and the solution was flushed through a short plug of silica gel affording 170 mg (98%) of 2-(tert-butoxyoxalyl-amino)-7-(((5-benzyloxy-1H-indole-2-carbonyl)amino)methyl)-6-(4-methoxy-benzyl)-4,5,6,7-tetrahydro[2,3-c]pyridine-3-carboxylic acid ethyl ester which was not purified further.

LC-MS: m/z: 725.21 [M+H]+

2-(tert-Butoxyoxalyl-amino)-7-(((5-benzyloxy-1H-indole-2-carbonyl)amino)-methyl)-6-(4-methoxy-benzyl)-4,5,6,7-tetrahydro[2,3-c]pyridine-3-carboxylic acid ethyl ester (100 mg) was added to test tubes (18×150 mm) using ethyl acetate (3 mL) and ethanol (3 mL). To the solutions was added Pearlman's catalyst (60 mg), Degussa Pd/C (E101 NE/W, 40 mg), and trifluoroacetic acid (0.6 mL). The reaction mixtures (in test tubes) were added to a Parr jar and hydrogenated at 50 psi for 36 hours. The reaction mixtures were then filtered through a plug of celite using acetonitrile and concentrated in vacuo. The crude material was purified by preparative chromatography using a mixture of dichloromethane/methanol (10:1) as eluent, which afforded 34 mg of 2-(tert-butoxyoxalyl-amino)-7-(((5-benzyloxy-1H-indole-2-carbonyl)amino)methyl)-4,5,6,7-tetrahydro[2, 3-c]pyridine-3-carboxylic acid ethyl ester.

To 2-(tert-butoxyoxalyl-amino)-7-(((5-benzyloxy-1H-indole-2-carbonyl)amino)-methyl)-4,5,6,7-tetrahydro[2,3-c] pyridine-3-carboxylic acid ethyl ester (34 mg) was added trifluoroacetic acid (50% in dichloromethane) at 0° C. and then warmed to room temperature and stirred for 1.5 hours. The crude solution was concentrated in vacuo and further dried under high vacuum affording 28 mg (90%) of the title compound.

$^1$H-NMR (300 MHz, DMSO-$d_6$): δ 12.16 (s, 1H), 11.39 (s, 1H), 9.57 (bs, 1H), 9.39 (bs, 1H), 9.11 (m, 1H), 7.26 (m, 1H), 7.22 (m, 1H), 7.05 (m, 1H), 5.01 (bs, 1H), 4.43 (q, 2H, J=7.8), 1.35 (t, 3H, J=6.9).

LC-MS: m/z: 487.16 [M+H]+

Example 42 (OC 297923)

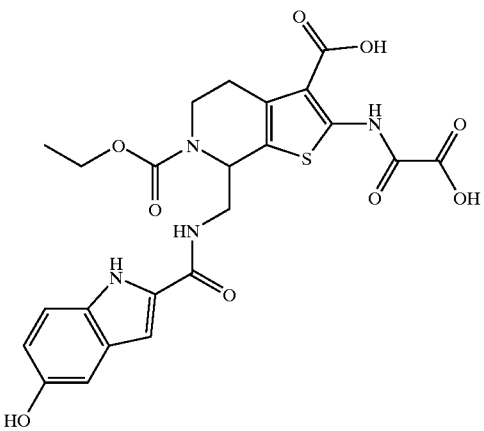

7-(((5-Hydroxy-1H-indole-2-carbonyl)amino)methyl)-2-(oxalyl-amino)-4,7-dihydro-5H-thieno[2,3-c]pyridine-3,6-dicarboxylic acid 6-ethyl ester To the solution of 2-amino-7-aminomethyl-6-(4-methoxy-benzyl)-4,5,6,7-tetrahydro-thieno[2,3-c]pyridine-3-carboxylic acid tert-butyl ester (0.23 g, 0.56 mmol), 5-tert-butyl-dimethyl-silanyloxy)-1H-indole-2-carboxylic acid (162 mg, 0.56 mmol), 1-hydroxy-benzotriazole hydrate (79 mg, 0.59 mmol) and N,N-diisopropylethylamine (290 μL, 1.8 mmol) in acetonitrile (20 mL) was added 1-(3-(dimethyl-amino)propyl)-3-ethylcarbodiimide hydrochloride (113 mg, 0.59 mmol). The mixture was stirred at room temperature for 16 hours. The solvent was removed in vacuo. The residue was taken into ethyl acetate (100 mL) and the solution was washed with saturated sodium bicarbonate (2×30 mL) and brine (30 mL) and dried over $MgSO_4$ and filtered. The solvent was removed in vacuo. The residue was chromatographed on silica gel column using a mixture of 10% ethyl acetate/chloroform as eluent, which yielded 285 mg (75%) of 2-amino-7-(((5-(tert-butyl-dimethyl-silanyloxy)-1H-indole-2-carbonyl)amino)methyl)-6-(4-methoxy-benzyl)-4,5,6,7-tetrahydro-thieno[2,3-c]pyridine-3-carboxylic acid tert-butyl ester as a solid.

$^1$H-NMR (300 MHz, $CDCl_3$): δ 8.90 (s, 1H), 7.60-7.40 (m, 4H), 7.10 (s, 1H), 6.94 (dd, 1H, J=6.6, and J=1.8 Hz), 6.82 (bs, 1H), 6.77 (s, 1H), 5.99 (s, 2H), 3.90-3.70 (m, 5H), 3.60-2.70 (m, 4H), 1.62 (s, 9H), 1.02 (s, 9H), 0.20 (s, 6H).

To a stirred solution of 2-amino-7-(((5-(tert-butyl-dimethyl-silanyloxy)-1H-indole-2-carbonyl)amino) methyl)-6-(4-methoxy-benzyl)-4,5,6,7-tetrahydro-thieno[2, 3-c]pyridine-3-carboxylic acid tert-butyl ester (280 mg, 0.414 mmol) in tetrahydrofuran (10 mL) was added imidazol-1-yl-oxo-acetic acid tert-butyl ester (243 mg, 1.24 mmol) in tetrahydrofuran (1 mL). The mixture was stirred at room temperature for 16 hours. The solvent was removed in vacuo. The residue was taken into ethyl acetate (50 mL), washed with saturated sodium bicarbonate (2×10 mL), brine (10 mL), and dried ($MgSO_4$) and filtered. The solvent was removed in vacuo. The residue was chromatographed on silica gel column using a mixture of 10% ethyl acetate/chloroform, which afforded 295 mg (89%) of 2-(tert-butoxyoxalyl-amino)-7-(((5-(tert-butyl-dimethyl-silanyloxy)-1H-indole-2-carbonyl)amino)-methyl)-6-(4-methoxy-benzyl)-4,5,6,7-tetrahydro-thieno[2,3-c]pyridine-3-carboxylic acid tert-butyl ester as a solid.

¹H-NMR (300 MHz, CDCl₃): δ 12.59 (s, 1H), 8.92 (s, 1H), 7.50-7.30 (m, 4H), 7.17 (s, 1H), 7.03 (dd, 1H, J=6.6, and J=1.8 Hz), 6.79 (bs, 1H), 6.62 (s, 1H), 3.92-3.60 (m, 5H), 3.50-2.70 (m, 4H), 1.60 (s, 18H), 1.04 (s, 9H), 0.18 (s, 6H).

To a solution of 2-(tert-butoxyoxalyl-amino)-7-(((5-(tert-butyl-dimethyl-silanyloxy)-1H-indole-2-carbonyl)amino)-methyl)-6-(4-methoxy-benzyl)-4,5,6,7-tetrahydro-thieno[2,3-c]pyridine-3-carboxylic acid tert-butyl ester (290 mg, 0.36 mmol) and 9-fluorenylmethyl chloroformate (466 mg, 1.8 mmol) in 1,2-dichloroethane (10 mL) was added NaHCO₃ (302 mg, 3.6 mmol). The mixture was stirred at refluxed for 72 hours. The solid was filtered off. The solvent of the filtrate was removed in vacuo and the residue was chromatographed on silica gel chromatotron using a mixture of 10% ethyl acetate/chloroform, which afforded 125 mg (38%) of 2-(tert-butoxyoxalyl-amino)-7-(((5-(tert-butyl-dimethyl-silanyloxy)-1H-indole-2-carbonyl)amino)-methyl)-4,5,6,7-tetrahydro-thieno[2,3-c]pyridine-3,6-dicarboxylic acid 3-tert-butyl ester 6-(9H-fluoren-9-ylmethyl) ester as a solid.

¹H-NMR (300 MHz, CDCl₃): δ 12.63-12.54 (bs, 1H), 8.92 (s, 1H), 7.80-7.40 (m, 8H), 7.25-6.78 (m, 3H), 6.72-6.38 (bs, 1H), 6.13 (s, 1H), 4.91-4.67 (s, 1H), 4.47 (d, 1H, J=8.7 Hz), 4.50-4.00 (m, 3H), 3.70-3.60 (m, 1H), 3.34-2.60 (m, 4H), 1.62 (s, 18H), 1.02-0.99 (s, 9H), 0.21-0.16 (s, 6H).

To a solution of piperidine in tetrahydrofuran (5%) was added 2-(tert-butoxyoxalyl-amino)-7-(((5-(tert-butyl-dimethyl-silanyloxy)-1H-indole-2-carbonyl)amino)-methyl)-4,5,6,7-tetrahydro-thieno[2,3-c]pyridine-3,6-dicarboxylic acid 3-tert-butyl ester 6-(9H-fluoren-9-ylmethyl) ester (120 mg, 0.132 mmol). The solution was stirred for 30 min. The solvent was removed and the residue was washed with diethyl ether to provide 92 mg (100%) of 2-(tert-butoxyoxalyl-amino)-7-(((5-(tert-butyl-dimethyl-silanyloxy)-1H-indole-2-carbonyl)amino)methyl)-4,5,6,7-tetrahydro-thieno[2,3-c]pyridine-3-carboxylic acid tert-butyl ester.

¹H-NMR (300 MHz, CDCl₃): δ 12.56 (s, 1H), 9.10 (s, 1H), 7.06 (d, 1H, J=11.4 Hz), 7.01 (d, 1H, J=11.4 Hz), 6.85 (dd, 1H, J=6.6, 2.0 Hz), 6.92-6.68 (m, 2H), 5.60 (bs, 1H), 4.90 (s, 1H), 4.60-2.80 (m, 5H), 1.62 (s, 18H), 1.01 (s, 9H), 0.20 (s, 6H).

To a solution of 2-(tert-butoxyoxalyl-amino)-7-(((5-(tert-butyl-dimethyl-silanyloxy)-1H-indole-2-carbonyl)amino) methyl)-4,5,6,7-tetrahydro-thieno[2,3-c]pyridine-3-carboxylic acid tert-butyl ester (90 mg, 0.13 mmol) in acetonitrile (5 mL) was added N,N-diisopropylethylamine (23 µL, 0.14 mmol) and ethyl chloroformate (15 µL, 0.14 mmol). The solution was stirred for 1 hour and then taken into ethyl acetate (50 mL). The solution was washed with saturated sodium bicarbonate (2×10 mL) and brine (10 mL), dried (MgSO₄) and filtered. The solvent was removed in vacuo. The residue was chromatographed on silica gel column using a mixture of 10% ethyl acetate/chloroformas eluent, which afforded 96 mg (96%) of 2-(tert-butoxyoxalyl-amino)-7-(((5-(tert-butyl-dimethyl-silanyloxy)-1H-indole-2-carbonyl)amino)methyl)-4,5,6,7-tetrahydro-thieno[2,3-c] pyridine-3,6-dicarboxylic acid 3-tert-butyl ester 6-ethyl ester as a solid.

¹H-NMR (300 MHz, CDCl₃): δ 12.58 (bs, 1H), 9.32 (bs, 1H), 7.32-7.28 (bd, J=6.6 Hz), 7.03 (s, 1H), 6.85 (dd, 1H, J=6.6, and J=2.0 Hz), 6.80-6.69 (s, 1H), 5.50-5.40 (m, 1H), 4.44-4-25 (m, 1H), 4.16-3.88 (m, 5H), 3.19 (t, 1H, J=10.8 Hz), 2.99 (d, 1H, J=11.4 Hz), 2.90-2.70 (m, 1H), 1.61 (s, 9H), 1.60 (s, 9H), 1.20 (t, 3H, J=5.4Hz), 0.99(s, 9H), 0.19 (s, 6H).

To a solution of trifluoro acetic acid and water (95%) was added 2-(tert-butoxyoxalyl-amino)-7-(((5-(tert-butyl-dimethyl-silanyloxy)-1H-indole-2-carbonyl)amino) methyl)-4,5,6,7-tetrahydro-thieno[2,3-c]pyridine-3,6-dicarboxylic acid 3-tert-butyl ester 6-ethyl ester (94 mg, 0.12 mmol). The solution was stirred for 24 hours. The solvent was removed in vacuo. The residue was washed with methylene chloride followed by diethyl ether affording 60 mg (93%) of the title compound as a solid.

¹H-NMR (300 MHz, DMSO-d₆): δ 12.36 (s, 1H), 11.3 (s, 1H), 8.72 (s, 1H), 7.22 (d, 1H, J=8.7 Hz), 6.90 (d, 1H, J=10.5 Hz), 6.89 (d, 1H, J=11.4 Hz), 6.72 (dd, 1H, J=8.7, 2.1Hz), 5.35 (bs, 1H), 4.26-3.64 (m, 6H), 3.20 (d, 1H, J=11.7 Hz), 2.58 (m, 1H), 0.91 (t, 3H, J=7.5 Hz).

LC-MS: m/z: 531 [M+H]⁺

What is claimed is:

1. A compound of Formula 1

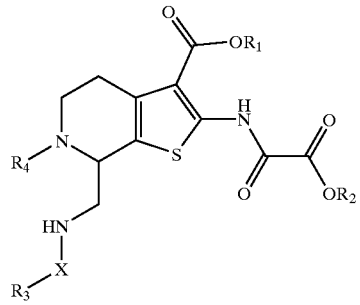

Formula 1 wherein

X is —C(O)— or S(O)₂—;

R₁ and R₂ are independently hydrogen or a functional group that can be converted to hydrogen in vivo;

R₃ is C₁–C₆alkyl, C₂–C₆alkenyl, C₂–C₆alkynyl, aryl, aryl-R₁₀-, aryl-N(R₃₅)-, aryl-R₁₁-N(R₃₆)-, N(R₃₇)(R₃₈)-R₃₉-, C₁–C₆alkyloxy or aryl-R₁₃—O- wherein aryl is phenyl, biphenyl, indenyl, naphthyl, imidazolyl, 1,2,3-triazolyl, thiophenyl, pyridyl, quinolyl, isoquinolyl, benzofuranyl, indolyl or benzimidazolyl, wherein the aryl group is optionally substituted with halogen, nitro, cyano, hydroxy, trihalomethyl, C₁–C₆alkyl, R₄₂—, R₄₂—R₁₄—, C₁–C₆alkyloxy, R₄₂—O—, R₄₂—S(O)₂—, R₄₂—R₅₀, R₄₂—N(R₁₆)—, R₁₈—C(O)—N(R₁₉), R₄₀—C(O)—O—R₄₁—O—C (O)—, R₄₂—C(O)—N(R₂₁)— or R₄₂—R₂₃—C(O)—N(R₂₄)—;

R₄ is hydrogen, R₂₇—O—C(O)—, aryl-R₂₈—O—C (O)—, R₂₉—C(O)—O—R₃₀—O—C(O)— or aryl-R₃₁—C(O)—O—R₃₂—O—C(O)— wherein aryl is phenyl, naphthyl or thiophenyl, wherein the aryl group is optionally substituted with halogen, nitro, cyano, trihalomethyl, R₄₃—, R₄₃—R₃₃—, C₁–C₆alkyloxy or R₄₃—R₃₄—O—;

and wherein R₁₀, R₁₁, R₁₃, R₁₄, R₁₅, R₂₃, R₂₈, R₃₀, R₃₁, R₃₂, R₃₃, R₃₄, R₃₉, and R₄₁ independently are C₁–C₆alkylene, wherein R₁₈, R₂₇, R₂₉, and R₄₀ independently are C₁–C₆alkyl and wherein R₁₆, R₁₉, R₂₁, R₂₄, R₃₅, R₃₆, R₃₇ and R₃₈ independently are hydrogen or C₁–C₆alkyl, wherein R₄₂ and R₄₃ are independently phenyl, naphthyl or thiophenyl;

or a salt thereof with a pharmaceutically acceptable acid or base, or any optical isomer or mixture of optical isomers, or any tautomeric form.

2. A compound according to claim 1 wherein $R^1$ and $R^2$ are independently hydrogen, $C_1$–$C_6$alkyl, aryl-$R_5$—, $R_6$—C(O)—O—$R_7$— or aryl-$R_8$—C(O)—O—$R_9$—, wherein $R_5$, $R_6$, $R_7$, $R_8$, and $R_9$ independently are $C_1$–$C_6$alkylene, wherein aryl is phenyl, naphthyl or thiophenyl, wherein the aryl group is optionally substituted with halogen, nitro, trihalomethyl, $C_1$–$C_6$alkyl or $C_1$–$C_6$alkyloxy.

3. A compound according to claim 1 wherein X is C(O).

4. A compound according to claim 1 wherein X is $S(O)_2$.

5. A compound according to claim 1 wherein $R_1$ and $R_2$ are independently hydrogen, $C_1$–$C_6$alkyl, aryl-$R_5$—, or $R_6$—C(O)—O—$R_7$—, wherein aryl is phenyl, naphthyl or thiophenyl, wherein the aryl group is optionally substituted with halogen, nitro, trihalomethyl, $C_1$–$C_6$alkyl or $C_1$–$C_6$alkyloxy.

6. A compound according to claim 5 wherein $R_1$ and $R_2$ are independently hydrogen or $C_1$–$C_6$alkyl.

7. A compound according to claim 6 wherein $R_1$ and $R_2$ are hydrogen.

8. A compound according to claim 1 wherein $R_3$ is $C_1$–$C_6$alkyl, $C_2$–$C_6$alkenyl, $C_2$–$C_6$alkynyl, aryl, aryl-$R_{10}$—, aryl-N($R_{35}$)—, N($R_{37}$)($R_{38}$)—$R_{39}$—, or $C_1$–$C_6$alkyloxy wherein aryl is phenyl, biphenyl, indenyl, naphthyl, imidazolyl, 1,2,3-triazolyl, thiophenyl, pyridyl, quinolyl, isoquinolyl, indolyl or benzimidazolyl, wherein the aryl group is optionally substituted with halogen, nitro, cyano, hydroxy, trihalomethyl, $C_1$–$C_6$alkyl, $R_{42}$—, $R_{42}$—$R_{14}$—, $C_1$–$C_6$alkyloxy, $R_{42}$—O—, $R_{42}$—$S(O)_2$—, $R_{42}$—$R_{15}$—O—, $R_{42}$—N($R_{16}$)—, $R_{18}$—C(O)—N($R_{19}$)—, $R_{40}$—C(O)—O—$R_{41}$—O—C(O)—, $R_{42}$—C(O)—N($R_{21}$)— or $R_{42}$—$R_{23}$—C(O)—N($R_{24}$)—.

9. A compound according to claim 8 wherein $R_3$ is $C_1$–$C_6$alkyl, aryl, aryl-$R_{10}$—, aryl-N($R_{35}$)—, or N($R_{37}$)($R_{38}$)—$R_{39}$—, wherein aryl is phenyl, biphenyl, indenyl, naphthyl, imidazolyl, 1,2,3-triazolyl, thiophenyl, pyridyl, quinolyl, isoquinolyl, indolyl or benzimidazolyl, wherein the aryl group is optionally substituted with halogen, nitro, cyano, hydroxy, trihalomethyl, $C_1$–$C_6$alkyl, $R_{42}$—, $R_{42}$—$R_{14}$—, $C_1$–$C_6$alkyloxy, $R_{42}$—O—, $R_{42}$—$S(O)_2$—, $R_{42}$—$R_{15}$—O—, $R_{42}$—N($R_{16}$)—, $R_{18}$—C(O)—N($R_{19}$)—, $R_{40}$—C(O)—O—$R_{41}$—O—C(O)—, $R_{42}$—C(O)—N($R_{21}$)— or $R_{42}$—$R_{23}$—C(O)—N($R_{24}$)—.

10. A compound according to claim 9 wherein $R_3$ is aryl, aryl-$R_{10}$—, or aryl-N($R_{35}$)—, wherein aryl is phenyl, biphenyl, indenyl, naphthyl, imidazolyl, 1,2,3-triazolyl, thiophenyl, pyridyl, quinolyl, isoquinolyl, indolyl or benzimidazolyl, wherein the aryl group is optionally substituted with halogen, nitro, cyano, hydroxy, trihalomethyl, $C_1$–$C_6$alkyl, $R_{42}$—, $R_{42}$—$R_{14}$—, $C_1$–$C_6$alkyloxy, $R_{42}$—O—, $R_{42}$—$S(O)_2$—, $R_{42}$—$R_{15}$—O—, $R_{42}$—N($R_{16}$)—, $R_{18}$—C(O)—N($R_{19}$)—, $R_{40}$—C(O)—O—$R_{41}$—C(O)—, $R_{42}$—C(O)—N($R_{21}$)— or $R_{42}$—$R_{23}$—C(O)—N($R_{24}$)—.

11. A compound according to claim 10 wherein $R_3$ is aryl, wherein aryl is phenyl, biphenyl, indenyl, naphthyl, imidazolyl, 1,2,3-triazolyl, thiophenyl, pyridyl, quinolyl, isoquinolyl, indolyl or benzimidazolyl, wherein the aryl group is optionally substituted with halogen, nitro, cyano, hydroxy, trihalomethyl, $C_1$–$C_6$alkyl, $R_{42}$—, $R_{42}$—$R_{14}$—, $C_1$–$C_6$alkyloxy, $R_{42}$—O—, $R_{42}$—$S(O)_2$—, $R_{42}$—$R_{15}$—O—, $R_{42}$—N($R_{16}$)—C(O)—N($R_{19}$)—, $R_{40}$—C(O)—O—$R_{41}$—O—C(O)—, $R_{42}$—C(O)—N($R_{21}$)— or $R_{42}$—$R_{23}$—C(O)—N($R_{24}$)—.

12. A compound according to claim 8 wherein aryl is phenyl, biphenyl, naphthyl, 1,2,3-triazolyl, indolyl or benzimidazolyl.

13. A compound according to claim 12 wherein aryl is phenyl, naphthyl, or indolyl.

14. A compound according to claim 13 wherein aryl is phenyl.

15. A compound according to claim 8 wherein the aryl group is substituted by halogen, hydroxy, $C_1$–$C_6$alkyl, $R_{42}$—, $R_{42}$—$R_{14}$—, $C_1$–$C_6$alkyloxy, $R_{42}$—O—, $R_{18}$—C(O)—N($R_{19}$)—, $R_{40}$—C(O)—O—$R_{41}$—O—C(O)—, $R_{42}$—C(O)—N($R_{21}$)— or $R_{42}$—$R_{23}$—C(O)—N($R_{24}$)—.

16. A compound according to claim 15 wherein the aryl is substituted by hydroxy, $R_{42}$—, $R_{42}$—$R_{14}$—, $C_1$–$C_6$alkyloxy, or $R_{42}$—O—.

17. A compound according to claim 8 wherein $R_{42}$ is phenyl or thiophenyl.

18. A compound according to claim 1 wherein $R_4$ is hydrogen, $R_{27}$—O—C(O)—, or $R_{29}$—C(O)—O—$R_{30}$—O—C(O)—, wherein aryl is phenyl, naphthyl or thiophenyl, wherein the aryl group is optionally substituted with halogen, nitro, cyano, trihalomethyl, $R_{43}$—, $R_{43}$—$R_{33}$—, $C_1$–$C_6$alkyloxy or $R_{43}$—$R_{34}$—O—.

19. A compound according to claim 18 wherein $R_4$ is hydrogen.

20. A compound according to claim 18 wherein aryl is phenyl.

21. A compound according to claim 18 wherein aryl is substituted by halogen, hydroxy, $R_{43}$—, or $C_1$–$C_6$alkyloxy.

\* \* \* \* \*